United States Patent
Adini et al.

(10) Patent No.: US 8,618,055 B2
(45) Date of Patent: Dec. 31, 2013

(54) PROMININ-1 PEPTIDE FRAGMENTS AND USES THEREOF

(75) Inventors: Avner Adini, Brookline, MA (US); Robert D'Amato, Lexington, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/015,376

(22) Filed: Jan. 27, 2011

(65) Prior Publication Data

US 2011/0190210 A1    Aug. 4, 2011

Related U.S. Application Data

(63) Continuation-in-part of application No. PCT/US2009/051971, filed on Jul. 28, 2009.

(60) Provisional application No. 61/084,052, filed on Jul. 28, 2008.

(51) Int. Cl.
| | |
|---|---|
| *A61K 38/00* | (2006.01) |
| *A61K 38/16* | (2006.01) |
| *A61K 38/10* | (2006.01) |
| *A61K 38/04* | (2006.01) |
| *A61K 38/12* | (2006.01) |

(52) U.S. Cl.
USPC ....... 514/13.3; 514/21.3; 514/21.4; 514/21.5; 530/326; 530/327; 530/317

(58) Field of Classification Search
None
See application file for complete search history.

(56) References Cited

U.S. PATENT DOCUMENTS

| | | |
|---|---|---|
| 6,991,901 B2 | 1/2006 | Rastelli et al. |
| 2005/0119198 A1 | 6/2005 | Carmeliet et al. |
| 2006/0003323 A1* | 1/2006 | Alsobrook et al. ............... 435/6 |
| 2006/0182724 A1 | 8/2006 | Riordan |
| 2007/0100323 A1* | 5/2007 | Ludwig et al. ............... 604/509 |

FOREIGN PATENT DOCUMENTS

| | | |
|---|---|---|
| WO | 03/066097 | 2/2003 |
| WO | 2006/087233 | 2/2006 |
| WO | 2007/062138 | 11/2006 |
| WO | 2008/054716 | 5/2008 |

OTHER PUBLICATIONS

B0AZU8, UniProtKB/TrEMBL, submitted Jan. 2008.*
Horswill et al. 2005. Cell Cycle 4:552-555.*
Bokeriya et al., Cell Technologies in Biology and Medicine, 3:141-146 (2007). "The use of angiogenesis stimulators for the treatment of chronic ischemia of lower extremities.".
Bruno et al., The American Journal of Pathology, 169(6):2223-2235 (2006). "CD133+ renal progenitor cells contribute to tumor angiogenesis.".
Corbeil et al., Blood, 91(7):2625-6 (1998). "AC133 hematopoietic stem cell antigen: human homologue of mouse kidney prominin or distinct member of a novel protein family.".
Miraglia et al., Blood, 90(12):5013-21 (1997). "A novel five-transmembrane hematopoietic stem cell antigen: isolation, characterization, and molecular cloning.".
Suuronen et al., Circulation, 114(1):I-138-I-144 (2006). "Tissue-engineered injectable collagen-based matrices for improved cell delivery and vascularization of ischemic tissue using CD133+ progenitors expanded from the peripheral blood.".
Weigmann et al., PNAS USA, 94(23):12425-30 (1997). "Prominin, a novel microvilli-specific polytopic membrane protein of the apical surface of epithelial cells, is targeted to plasmalemmal protrusions of non-epithelial cells.".
Adini et al., The novel peptide, P1P, accelerates blood vessels perfusion and improves wound healing. Presented at ICI Meeting 2010. Children's Hospital, Boston. 18 pages.
Barcelos et al., Abstract 282: human CD133+ progenitor cells promote the cicatrisation of diabetic ischemic ulcers through paracrine stimulation of reepithelization. Circulation 2006;114(18): Suppl.
Barcelos et al., Abstract 734: paracrine promotion of diabetic ischemic ulcer healing by topically applied fetal aorta-derived vascular progenitor cells: involvement of the writ signaling. Circulation 2007;116(16): Suppl.
Florek et al., Prominin-1/CD133, a neural and hematopoietic stem cell marker, is expressed in adult human differentiated cells and certain types of kidney cancer. Cell Tissue Res. Jan. 2005;319(1):15-26. Epub Nov. 19, 2004.
Mizrak et al., CD133: molecule of the moment. J Pathol. Jan. 2008;214(1):3-9.
Shmelkov et al., AC133/CD133/Prominin-1. Int J Biochem Cell Biol. Apr. 2005;37(4):715-9.

* cited by examiner

*Primary Examiner* — Shulamith H Shafer
(74) *Attorney, Agent, or Firm* — Wolf, Greenfield & Sacks, P.C.

(57) ABSTRACT

Described herein are peptide compositions of a prominin-1, which have regenerative activity. As such the peptides are useful when regeneration is needed, for example, to enhance angiogenesis, increase VEGF binding to endothelial cells, promote vasodilation, enhance cell migration, enhance cell proliferation, stimulate neuronal growth, prevent neurodegeneration, and/or promote neuroregeneration.

13 Claims, 17 Drawing Sheets

```
                  330       340       350       360       370       380       390       400
              ....|....|....|....|....|....|....|....|....|....|....|....|....|....|....|....|
zebrafish     335 LNQLALSA-NFNGLPDVEAPLANLDAVLKTDLSNIVQKGYSSFNDTPQIVREQTKGIV---SAlpKVKGLLDKSGAEII 409
Norway rat    314 ASALQLGA-DFSQMPPVDDVLHRLQGVPEANFSSMVQEENATFNNLPIIVHMQMVSVV---KD---LKKALAEQPEGVR 385
Human         314 ARTLELGA-DFSQVPSVDHVLHQLKGVPEANFSSMVQEENSTFNALPALAAMQTSSVV---QE---LKKAVAQQPEGVR 385
Human         323 LSQLNSNP-ELRQLPPVDAELDNVNNVLRTDLDGLVQQGYQSLNDIPDRVQRQTTTVV---AG---IKRVLNSIGSDID 394
house mouse   324 LSSLGSSl-NSSQLPSVDVDRELNTVTEVDKTDLESLVKRGYTTIDEIPNTIQNQTVDVI---KD---VKNTLDSISSNIK 395
nematode      316 LESLAVTQFKIDQRFLPDATETGLSEIVNANITQVLAASNNQFEQLESRIQHEID------KEtysAQNMLKQIGDDLF 388
fruit fly     379 DSSQCl---HFENLPNTKEFVEGMENIVASEYYAIPQRGLSRLKKVSDKVKTQLSFVVppmmRDltkGRTlTFREHATNVR 455

410       420       430       440       450       460       470       480
              ....|....|....|....|....|....|....|....|....|....|....|....|....|....|....|....|
zebrafish     410 GFTKMFPVEPALQNFSKFLTDSQKNIEAYYPQIDQLDFYRMIGCVLICCLVVLVLAFNFLGLLCGSCGYDKNSTPTTRGC 489
Norway rat    386 MLAQAFPGSEATSRWSQALEGLEQRSRPYLQDVQRYETYRWILGCVLCSAILLVVICNLLGLSLGIWGLFARDDPSHSET 465
Human         386 TLAEGFPGLEAASRWAQALQEVEESSRPYLQEVQRYETYRWIVGCVLCSVVLFVVLCNLLGLNLGIWGLSARDDPSHFEA 465
human         395 NVTQRLPIQDILSAFSVYVNNTESYIHRNLPTLEEYDSYWWLGGLNVICSLLTLIVIFYYLGLLCGVCGYDRHATPTTRGC 474
house mouse   396 DMSQSIPIEDMLLQVSHYLNNSNRYLNQELPKLEEYDSYWWLGGLIVCFLLTLIVTFFFLGLLCGVFGYDKHATPTRRGC 475
nematode      389 LVAETISTQLRKVTFEEALYSTVSVSVSDPKKTPTLKYMQYSWYASLVITSLFILLALIFIFGVLYGICG--RRPTYYNDDCC 467
fruit fly     456 NIVEGVLSDIHKTL-----HSTKSFEDVYERFGHDRMVVSLIVCLLILIVCLLLILILFALLCGCFG--RRRTGYGDECC 526

490       500       510       520       530       540       550       560
              ....|....|....|....|....|....|....|....|....|....|....|....|....|....|....|....|
zebrafish     490 LSNTGGNLLMASVGFSFIFSWVLMGVVVTTFIVGGNIEKLVCEPLANRQIFKIIDTPYMVHPTKknflPGMLFQDPNIDL 569
Norway rat    466 KGEAGARFLMAGVAFSFLFAAPLILLVEATPLVGGNVQTLVCRSWESGELIYEFVDTPGNLPPS---MNLSYILGLRKMI 541
Human         466 KGEAGARFLMAGVGLSFLFAAPLILLVFATPIVGGNVQTLVCQSWENGELFEFADTPGNLPPS---MNLSQLLGLRKMI 541
Human         475 VSNTGGVFLMVGVGLSFLFCWILMLIVVLTFVGANVEKLLICEPYTSKELFERVLDTPYLLNEDweyYLSGKLFNKSKMKL 554
house mouse   476 VSNTGGIFLMAGVGFGEFLFCWILMLLVVLFVVGANVEKLLCEPYENKLLQVLDTPYLLKEQwqfYLSGMLFNNPDINM 555
nematode      468 VRSTGGKFYSFGIGAFLLIFVFLAVGTSALMFAVGNFSNLVCQPMRNP------LSHPESLSlAdryiNLWKANHTPENDi 542
fruit fly     527 SKSTGATCLLLAILLIFCVFSFIALVGLFYPMLGMVTYQGACAFLRDQENNTLFRQLDASIDLnhylPPSESNKEVVQPL 606

570       580       590       600       610       620       630       640
              ....|....|....|....|....|....|....|....|....|....|....|....|....|....|....|....|
zebrafish     570 TI--------GSMYRDCYENNGLIYSALIQLETKENFNK--FLNATVFNP---EIGNIFNNVNVDLQGMLILEQGKDNLIDF 637
Norway rat    542 SV--------FQAYRQCKAGTALMKVLQLNDSYDLDK---HLDIKQYTH---KLQQELQSFKVDLKDLDILNPAARQMLEAL 609
Human         542 SI--------HQAYQQCKEGAALWTVLQLNDSYDLEE---HLDINQYTN---KLRQELQSLRAVDTQSLDLLSSAARRDLEAL 609
Human         555 TF--------EQVYSDCKKNRGTYGTLHLQNSENISE---HLNINEHTG---SISSELESLRAVNLN--IFLLGAAGRKNLQDF 621
house mouse   556 TF--------EQVYRDCKRGRGIYAAFQLENVVNVSD---HFNIDQISE---NINTELENLNVNIDSIELLDNTGRKSLEDF 623
nematode      543 EVtlqskspAEIIRACSRNETLYNFYGFDKKYHLNKlqdFEEKDAYNQlqiSLRTTMENMPEIRPLDAFISRSELRDLEKL 622
fruit fly     607 RM--------SSAIKACHANQTIFDMMRQHMIYDINDltRIKVMSHSQ---ENTDSIKVFDEDLSTVVLLTKEERDELKTA 676
```

FIG. 1 (cont.)

```
                  650         660         670         680         690         700         710         720
             ....*....|....*....|....*....|....*....|....*....|....*....|....*....|....*....|
Zebrafish    638 ANTGIGDIDYQAYLFEVNKGVTVVDLLSYANELDAQADNL---PRGALENALKGHASSIRQIHKDQVVPMEQAMSNLNQS 714
Norway rat   610 QSSGLEKIHYRDFLVQIQKPVVKTDMGQLAKELEGLAQAH---NESLRRQQLQEEARELRSLYQEKVVPQENLVAKLNPS 686
Human        610 QSSGLQRIHYPDFIVQIQRPVVKTSMEQLAQELQGLAQAQ---DNSVLGQRLQEEAQGLRNLHQEKVVPQQSLVAKLNLS 686
Human        622 AACGIDRMNYDSYLAQTGKSPAGVNLLSPAYDLEAKANSL---PPGNLRNSLKRDAQTIKTIHQQRVLPIEQSLSTLYQS 698
house mouse  624 AHSGIDTIDYSTYLKETEKSPTEVNLLTPASTLEAKANQL---PEGKPKQAFLLDVQNIRAIHQHLLPPVQQSLNTLRQS 700
nematode     623 ASVNVSKVSQQG-LNAIKHAMDELDLASKTREFEESLD----ANSGRPKAVTIVLEQIRELEIQFAKPLRSRLEALYSN 696
fruit fly    677 GESKLAKYHSSLYMPSLCTQFTPMNLNALSEQLYKLSNDLeyPAYGWAKVSFWNEGLNTKAFYRNFVPKLTSLVEKMKAN 756

730         740         750         760         770         780         790         800
             ....*....|....*....|....*....|....*....|....*....|....*....|....*....|....*....|
Zebrafish    715 IRQLEKTSR----ELPVKVTNVLNAIEAAEVLISNNASHVVKQESDKFIKKIIGYFSQYTEWVKHSLAMEVAQCKPISNI 790
Norway rat   687 IRVLESSAP----KLQVNTSDLLDIVARLKGELPAQLNHILRNATECFLTREMGYFSQYVTWVREEVTQHIATCQFFSKA 762
Human        687 VRALESSAP----NLQLETSDVLANVTYLKGELPAWAARILRNVSECFLAREMGYFSQYVAWVREEVTQRIATCQPLSGA 762
Human        699 VKILQRTGN----GLLERVTRILASLDFAQNFITNNTSSVIIEETKKYGRTIIGYFEHYLQWIEFSISERVASCKPVATA 774
house mouse  701 VWTLQQTSN----KLPEKVKKILASLDSVQHFLTNNVSLIVIGETKKFGKTILGYFEHYLHWVFYAITERMTSCKPMATA 776
nematode     697 ITSLDEKLS----QLQVPVSSLLVKLQHAQALLAENMREHFGRAAKEEFQQMVNNIDQYIVHVKSQMESEVTSCQPLTQI 772
fruit fly    757 LKKIDELISYenhDFTNMTIKLTATAINSEQFIQTRGKDYINALGGNLTNSIDQMIDDYIDMIIKEANESVSHCAPLSYI 836

810         820         830         840         850         860         870         880
             ....*....|....*....|....*....|....*....|....*....|....*....|....*....|....*....|
Zebrafish    791 VDSA-EIVACSFIVDSVNTFWFGLG------------------------- 814
Norway rat   763 LDDG-HMILCDMMGQPLECLLVLPGlvhllphpqhhlrgqdlqvlpshpetaqihqlrdtalpypgqhlpeaieptgqg 841
Norway rat   763 LDNS-RVILCDMMADPWNAFWFCLA------------------------- 786
human        775 LDTAvDVFLCSYIIDPINLFWFGIG------------------------- 799
house mouse  777 MDSAVNGILCGYVADPINLFWFGIG------------------------- 801
nematode     773 ARQT-TAAVCAYTIDPYNGTWMCML------------------------- 796
fruit fly    837 YYRG-VDLICHRIVDPINGFWVGIL------------------------- 860

890         900         910
             ....*....|....*....|....*....|
Zebrafish    815 --GCCVLLIPSIIMSVKLAkfyrrMDTEDVFDDGSENWS 851
Norway rat   842 dtWGFPPVLLPCLSLDQTTS-----VTSVFERLASSAGL 875
Human        787 --WCTFFLIPSIIFAVKTSkyfrpIRKRLSSTSSEETQL 823
Human        800 --KATVFLLPALIFAVKLAkvyrrMDSEDVDDVETIPM 836
house mouse  802 --KATVLLLPAVIIAIKLAkyyrrMDSEDVDDVETVPM 838
nematode     797 --ICLVLLIPIVIISNSLIglyskMHAFFPKYIVEPPSET 833
fruit fly    861 --LCALLFLPLFLFVAHRIMclykkIYPYLATVGAAGVVE 897
```

| Sequence Tag | Sequence |
|---|---|
| #3 | LCGNSFSGGQPS |
| #42 | PNIPVLDEIKS |
| #77 | LCGVCGYDRHAT |
| #122 | ITNNTSSVIEE |
| #237 | DRVQRQTTTVVA |
| #640 | CSFAYDLEAKANSLPPGNLRN |

| | | |
|---|---|---|
| Ala-1 | ARVQRQTTTVVA | (SEQ. ID. NO. 39) |
| Ala-2 | DAVQRQTTTVVA | (SEQ. ID. NO. 40) |
| Ala-3 | DRAQRQTTTVVA | (SEQ. ID. NO. 41) |
| Ala-4 | DRVARQTTTVVA | (SEQ. ID. NO. 42) |
| Ala-5 | DRVQAQTTTVVA | (SEQ. ID. NO. 43) |
| Ala-6 | DRVQRATTTVVA | (SEQ. ID. NO. 44) |
| Ala-7 | DRVQRQATTVVA | (SEQ. ID. NO. 45) |
| Ala-8 | DRVQRQTATVVA | (SEQ. ID. NO. 46) |
| Ala-9 | DRVQRQTTAVVA | (SEQ. ID. NO. 47) |
| Ala-10 | DRVQRQTTTAVA | (SEQ. ID. NO. 48) |
| Ala-11 | DRVQRQTTTVAA | (SEQ. ID. NO. 49) |
| Ala-12 | DRVQRQTTTVVG | (SEQ. ID. NO. 50) |

SEQUENCE LISTING

<160> NUMBER OF SEQ ID NOS: 60

<210> SEQ ID NO 1
<211> LENGTH: 106
<212> TYPE: PRT
<213> ORGANISM: Homo sapiens

<400> SEQUENCE: 1

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
                20                  25                  30

Asn Tyr Glu Leu Pro Ala Thr Asn Tyr Glu Thr Gln Asp Ser His Lys
            35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu
            100                 105

<210> SEQ ID NO 2
<211> LENGTH: 254
<212> TYPE: PRT
<213> ORGANISM: Homo sapiens

<400> SEQUENCE: 2

Asn His Gln Val Arg Thr Arg Ile Lys Arg Ser Arg Lys Leu Ala Asp
1               5                   10                  15

Ser Asn Phe Lys Asp Leu Arg Thr Leu Leu Asn Glu Thr Pro Glu Gln
                20                  25                  30

Ile Lys Tyr Ile Leu Ala Gln Tyr Asn Thr Thr Lys Asp Lys Ala Phe
            35                  40                  45

Thr Asp Leu Asn Ser Ile Asn Ser Val Leu Gly Gly Gly Ile Leu Asp
        50                  55                  60

Arg Leu Arg Pro Asn Ile Ile Pro Val Leu Asp Glu Ile Lys Ser Met
65                  70                  75                  80

Ala Thr Ala Ile Lys Glu Thr Lys Glu Ala Leu Glu Asn Met Asn Ser
                85                  90                  95

Thr Leu Lys Ser Leu His Gln Gln Ser Thr Gln Leu Ser Ser Ser Leu
            100                 105                 110

```
Thr Ser Val Lys Thr Ser Leu Arg Ser Ser Leu Asn Asp Pro Leu Cys
        115                 120                 125

Leu Val His Pro Ser Ser Glu Thr Cys Asn Ser Ile Arg Leu Ser Leu
    130                 135                 140

Ser Gln Leu Asn Ser Asn Pro Glu Leu Arg Gln Leu Pro Pro Val Asp
145                 150                 155                 160

Ala Glu Leu Asp Asn Val Asn Asn Val Leu Arg Thr Asp Leu Asp Gly
                165                 170                 175

Leu Val Gln Gln Gly Tyr Gln Ser Leu Asn Asp Ile Pro Asp Arg Val
            180                 185                 190

Gln Arg Gln Thr Thr Thr Val Val Ala Gly Ile Lys Arg Val Leu Asn
        195                 200                 205

Ser Ile Gly Ser Asp Ile Asp Asn Val Thr Gln Arg Leu Pro Ile Gln
    210                 215                 220

Asp Ile Leu Ser Ala Phe Ser Val Tyr Val Asn Asn Thr Glu Ser Tyr
225                 230                 235                 240

Ile His Arg Asn Leu Pro Thr Leu Glu Glu Tyr Asp Ser Tyr
                245                 250

<210> SEQ ID NO 3
<211> LENGTH: 287
<212> TYPE: PRT
<213> ORGANISM: Homo sapiens

<400> SEQUENCE: 3

Thr Phe Val Phe Gly Ala Asn Val Glu Lys Leu Ile Cys Glu Pro Tyr
1               5                   10                  15

Thr Ser Lys Glu Leu Phe Arg Val Leu Asp Thr Pro Tyr Leu Leu Asn
            20                  25                  30

Glu Asp Trp Glu Tyr Tyr Leu Ser Gly Lys Leu Phe Asn Lys Ser Lys
        35                  40                  45

Met Lys Leu Thr Phe Glu Gln Val Tyr Ser Asp Cys Lys Lys Asn Arg
    50                  55                  60

Gly Thr Tyr Gly Thr Leu His Leu Gln Asn Ser Phe Asn Ile Ser Glu
65                  70                  75                  80

His Leu Asn Ile Asn Glu His Thr Gly Ser Ile Ser Ser Glu Leu Glu
                85                  90                  95

Ser Leu Lys Val Asn Leu Asn Ile Phe Leu Leu Gly Ala Ala Gly Arg
            100                 105                 110

Lys Asn Leu Gln Asp Phe Ala Ala Cys Gly Ile Asp Arg Met Asn Tyr
        115                 120                 125

Asp Ser Tyr Leu Ala Gln Thr Gly Lys Ser Pro Ala Gly Val Asn Leu
    130                 135                 140

Leu Ser Phe Ala Tyr Asp Leu Glu Ala Lys Ala Asn Ser Leu Pro Pro
145                 150                 155                 160

Gly Asn Leu Arg Asn Ser Leu Lys Arg Asp Ala Gln Thr Ile Lys Thr
                165                 170                 175

Ile His Gln Gln Arg Val Leu Pro Ile Glu Gln Ser Leu Ser Thr Leu
            180                 185                 190

Tyr Gln Ser Val Lys Ile Leu Gln Arg Thr Gly Asn Gly Leu Leu Glu
        195                 200                 205

Arg Val Thr Arg Ile Leu Ala Ser Leu Asp Phe Ala Gln Asn Phe Ile
    210                 215                 220

Thr Asn Asn Thr Ser Ser Val Ile Ile Glu Glu Thr Lys Lys Tyr Gly
225                 230                 235                 240
```

```
Arg Thr Ile Ile Gly Tyr Phe Glu His Tyr Leu Gln Trp Ile Glu Phe
                245                 250                 255

Ser Ile Ser Glu Lys Val Ala Ser Cys Lys Pro Val Ala Thr Ala Leu
            260                 265                 270

Asp Thr Ala Val Asp Val Phe Leu Cys Ser Tyr Ile Ile Asp Pro
        275                 280                 285

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Cys Gly Asn Ser Phe Ser Gly Gly Gln Pro Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Asn Ile Ile Pro Val Leu Asp Glu Ile Lys Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Cys Gly Val Cys Gly Tyr Asp Arg His Ala Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Thr Asn Asn Thr Ser Ser Val Ile Ile Glu Glu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Val Gln Arg Gln Thr Thr Thr Val Val Ala
1               5                   10
```

```
<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Ser Phe Ala Tyr Asp Leu Glu Ala Lys Ala Asn Ser Leu Pro Pro
1               5                   10                  15

Gly Asn Leu Arg Asn
            20

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgtgcggca acagctttag cggcggccag ccgagc                              36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gctcggctgg ccgccgctaa agctgttgcc gcacag                              36

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Thr Thr Val Val Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Val Gln Arg Gln
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

Val Gln Arg Gln Thr Thr Thr Val
1               5

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Cys Gly Gly Asp Arg Val Gln Arg Gln Thr Thr Thr Val Val Ala
1               5                   10                  15

Gly Gly Cys

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Cys Gly Gly Asp Arg Val Gln Arg Gln Thr Thr Thr Val Val Ala
1               5                   10                  15

Gly Gly Gly Gly Gly Gly Cys
            20

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Gly Gly Gly Gly Gly Gly Asp Arg Val Gln Arg Gln Thr Thr Thr
1               5                   10                  15

Val Val Ala Gly Gly Cys Ala
            20

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(32)
<223> OTHER INFORMATION: This region may encompass 1 to 8 "Gly Gly Gly
      Ser" repeating units
<220> FEATURE:
<223> OTHER INFORMATION: see specification as filed for detailed
      description of substitutions and preferred embodiments

<400> SEQUENCE: 18

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 832
<212> TYPE: PRT
<213> ORGANISM: Danio rerio

<400> SEQUENCE: 20

Asp Arg Glu Glu His Arg Glu Ser Pro Pro Arg Thr Ala Met Leu Arg
1               5                   10                  15

Ala Pro Val Glu Thr Leu Asp Phe Gly Phe Val Pro Ser Val Val Tyr
                20                  25                  30

Glu Thr His Ala Tyr Tyr Glu Pro Gly Pro Met Gly Ile Leu Phe His
            35                  40                  45

Met Val His Ala Phe Leu Tyr Val Val Gln Pro Asn Pro Phe Pro Lys
        50                  55                  60

Asp Leu Ile Val Lys Met Val Gln Gln Asn Met Gly Gly Ile Lys Gly
65                  70                  75                  80

Asp Asp Tyr Lys Lys Pro Glu Asn Val Val Leu Leu Leu Gln Thr Ile
                85                  90                  95

Tyr Tyr Glu Leu Gly Phe Ile Val Leu Ser Val Leu Gly Val Phe Phe
            100                 105                 110

Val Leu Leu Met Pro Ile Val Gly Leu Cys Phe Cys Val Cys Arg Cys
        115                 120                 125

Cys Glu Asn Cys Gly Gly Glu Met His Gln Arg Gln Lys Lys Asn Gly
130                 135                 140

Asp Cys Leu Arg Gly Phe Tyr Met Ala Thr Leu Ile Ala Thr Ser Val
145                 150                 155                 160

Phe Leu Ala Val Gly Val Thr Val Ala Tyr Val Ala Asn Gln Asn Ile
                165                 170                 175

Thr Ser Gln Ile Lys Ser Thr Arg Arg Leu Val Ser Thr Asn Ile Arg
            180                 185                 190

Asp Leu Lys Ala Phe Ala Asn Tyr Thr Pro Ala Gln Ile Asp Tyr Leu
        195                 200                 205

Thr Ala Gln Tyr Thr Thr Ala Lys Asn Lys Val Leu Ser Asp Leu Asp
210                 215                 220

Asn Ile Gly Thr Leu Leu Gly Gly Gln Ile His Asn Lys Leu Glu Ser
225                 230                 235                 240

Glu Val Val Pro Ala Leu Asp His Ala Leu Arg Met Thr Ala Ala Met
                245                 250                 255

Arg Glu Thr Lys Glu Ser Leu Glu Ser Val Ser Thr Ser Leu Glu Thr
            260                 265                 270

Leu Gln Glu Gly Thr Gly Arg Leu Gln Val Ser Leu Gln Ser Glu Arg
        275                 280                 285

Ala Ser Leu Ser Asn Thr Leu Asn Asp Trp Ala Cys Ser Asn Glu Asp
290                 295                 300

Val Thr His Thr Cys Asn Ser Ile Arg Gly Thr Leu Asn Gln Leu Ala
305                 310                 315                 320
```

```
Leu Ser Ala Asn Phe Asn Gly Leu Pro Asp Val Glu Ala Pro Leu Ala
                325                 330                 335

Asn Leu Asp Ala Val Leu Lys Thr Asp Leu Ser Asn Ile Val Gln Lys
            340                 345                 350

Gly Tyr Ser Ser Phe Asn Asp Thr Pro Gln Leu Val Arg Glu Gln Thr
        355                 360                 365

Lys Gly Ile Val Ser Ala Leu Pro Lys Val Lys Gly Leu Leu Asp Lys
    370                 375                 380

Ser Gly Ala Glu Ile Ile Gly Phe Thr Lys Met Phe Pro Val Glu Pro
385                 390                 395                 400

Ala Leu Gln Asn Phe Ser Lys Phe Leu Thr Asp Ser Gln Lys Asn Ile
                405                 410                 415

Glu Ala Tyr Tyr Pro Gln Ile Asp Gln Leu Asp Phe Tyr Arg Trp Ile
            420                 425                 430

Gly Cys Val Leu Ile Cys Cys Leu Val Val Leu Val Leu Ala Phe Asn
        435                 440                 445

Phe Leu Gly Leu Leu Cys Gly Ser Cys Gly Tyr Asp Lys Asn Ser Thr
    450                 455                 460

Pro Thr Thr Arg Gly Cys Leu Ser Asn Thr Gly Asn Leu Leu Met
465                 470                 475                 480

Ala Ser Val Gly Phe Ser Phe Ile Phe Ser Trp Val Leu Met Gly Val
                485                 490                 495

Val Val Thr Thr Phe Ile Val Gly Gly Asn Ile Glu Lys Leu Val Cys
            500                 505                 510

Glu Pro Leu Ala Asn Arg Gln Ile Phe Lys Ile Ile Asp Thr Pro Tyr
        515                 520                 525

Met Val His Pro Thr Lys Lys Asn Phe Leu Pro Gly Met Leu Phe Gln
    530                 535                 540

Asp Pro Asn Ile Asp Leu Thr Ile Gly Ser Met Tyr Arg Asp Cys Tyr
545                 550                 555                 560

Glu Asn Asn Gly Leu Tyr Ser Ala Leu Gln Leu Glu Thr Lys Phe Asn
                565                 570                 575

Phe Asn Lys Phe Leu Asn Ala Thr Val Phe Asn Pro Glu Ile Gly Asn
            580                 585                 590

Ile Phe Asn Asn Val Asn Val Asp Leu Gln Gly Met Leu Leu Leu Glu
        595                 600                 605

Gln Glu Gly Lys Asp Asn Leu Ile Asp Phe Ala Asn Thr Gly Ile Gly
    610                 615                 620

Asp Ile Asp Tyr Gln Ala Tyr Leu Thr Glu Val Asn Lys Gly Val Thr
625                 630                 635                 640

Val Val Asp Leu Leu Ser Tyr Ala Asn Glu Leu Asp Ala Gln Ala Asp
                645                 650                 655

Asn Leu Pro Arg Gly Ala Leu Glu Asn Ala Leu Lys Gly His Ala Ser
            660                 665                 670

Ser Ile Arg Gln Ile His Lys Asp Gln Val Val Pro Met Glu Gln Ala
        675                 680                 685

Met Ser Asn Leu Asn Gln Ser Ile Arg Gln Leu Glu Lys Thr Ser Arg
    690                 695                 700

Glu Leu Pro Val Lys Val Thr Asn Val Leu Asn Ala Ile Glu Ala Ala
705                 710                 715                 720

Glu Tyr Leu Ile Ser Asn Asn Ala Ser His Val Val Lys Gln Glu Ser
                725                 730                 735

Asp Lys Phe Ile Lys Lys Ile Ile Gly Tyr Phe Ser Gln Tyr Thr Glu
```

```
                        740                 745                 750
Trp Val Lys His Ser Leu Ala Met Glu Val Ala Gln Cys Lys Pro Ile
        755                 760                 765

Ser Asn Ile Val Asp Ser Ala Glu Ile Val Ala Cys Ser Phe Ile Val
    770                 775                 780

Asp Ser Val Asn Thr Phe Trp Phe Gly Leu Gly Gly Cys Cys Val Leu
785                 790                 795                 800

Leu Ile Pro Ser Ile Ile Met Ser Val Lys Leu Ala Lys Phe Tyr Arg
                805                 810                 815

Arg Met Asp Thr Glu Asp Val Phe Asp Asp Gly Ser Glu Asn Trp Ser
                820                 825                 830
```

<210> SEQ ID NO 21
<211> LENGTH: 858
<212> TYPE: PRT
<213> ORGANISM: Rattus norvegicus

<400> SEQUENCE: 21

```
Leu Ala Leu Ser Leu Pro Arg Ala Val Ala Ala Asp Cys Gly Ser Leu
1               5                   10                  15

Gly Arg Val Glu His Leu Ala Phe Ala Pro Val Pro Gly Thr Glu Pro
                20                  25                  30

Thr Ala Pro Arg Val Arg Ala Pro Trp Pro Leu Asp Ser Leu Tyr Gly
        35                  40                  45

Thr Val Arg Arg Phe Leu Ser Val Val Gln Leu Asn Pro Phe Pro Ala
    50                  55                  60

Glu Leu Ile Lys Thr Leu Leu Asn Asp Pro Ser Ser Val Lys Thr Asp
65                  70                  75                  80

Glu Val Val Arg Tyr Glu Ala Gly Tyr Val Val Cys Ala Val Ile Ala
                85                  90                  95

Gly Leu Tyr Leu Leu Leu Val Pro Ile Thr Gly Leu Cys Phe Cys Cys
                100                 105                 110

Cys Arg Cys Arg Arg Cys Gly Gly Arg Val Lys Thr Glu His Lys
            115                 120                 125

Ala Met Ala Cys Glu Arg Gly Thr Leu Met Thr Phe Leu Leu Leu Thr
    130                 135                 140

Thr Leu Met Leu Leu Ile Gly Met Val Cys Ala Phe Ala Thr Asn Gln
145                 150                 155                 160

Phe Thr His Ser Gln Thr Gly Pro Ser Val Glu Ala Val Pro Glu Thr
                165                 170                 175

Leu Leu Ser Leu Arg Gly Leu Val Ser Asp Val Pro Lys Lys Leu Gln
            180                 185                 190

Ala Val Ala Asp Gln Phe Ser Leu Pro Gln Lys Gln Val Ser Lys Asp
    195                 200                 205

Leu Asp Gly Val Gly Glu Asn Leu Gly Asn Ile Ile His Asn Gln Leu
210                 215                 220

Lys Ser Thr Val Tyr Pro Val Leu Ala Ser Val His Gly Leu Gly Gln
225                 230                 235                 240

Ala Leu Gln Val Ser Ile Asp His Leu Gln Ser Val Asn Ala Thr Ser
                245                 250                 255

Val Glu Leu Arg Glu Gly Gln Gln His Leu Gly Pro Pro Val Gln Ala
            260                 265                 270

His Arg Glu Arg Leu Leu Ala Leu Leu Gln Glu Ser Trp Cys His Glu
    275                 280                 285

Asn Cys Lys Gly Ala Leu Ser Gln Ala Ser Ala Leu Gln Leu Gly Ala
```

```
                290                 295                 300
Asp Phe Ser Gln Met Pro Val Asp Val Leu His Arg Leu Gln
305                 310                 315                 320

Gly Val Pro Glu Ala Asn Phe Ser Ser Met Val Gln Glu Asn Ala
                325                 330                 335

Thr Phe Asn Asn Leu Pro Ile Leu Val His Met Gln Met Val Ser Val
                340                 345                 350

Val Lys Asp Leu Lys Lys Ala Leu Ala Glu Gln Pro Glu Gly Val Arg
                355                 360                 365

Met Leu Ala Gln Ala Phe Pro Gly Ser Glu Ala Thr Ser Arg Trp Ser
370                 375                 380

Gln Ala Leu Glu Gly Leu Glu Gln Arg Ser Arg Pro Tyr Leu Gln Asp
385                 390                 395                 400

Val Gln Arg Tyr Glu Thr Tyr Arg Trp Ile Leu Gly Cys Val Leu Cys
                405                 410                 415

Ser Ala Ile Leu Leu Val Val Ile Cys Asn Leu Leu Gly Leu Ser Leu
                420                 425                 430

Gly Ile Trp Gly Leu Phe Ala Arg Glu Asp Pro Ser His Ser Glu Thr
                435                 440                 445

Lys Gly Glu Ala Gly Ala Arg Phe Leu Met Ala Gly Val Ala Phe Ser
                450                 455                 460

Phe Leu Phe Ala Ala Pro Leu Ile Leu Leu Val Phe Ala Thr Phe Leu
465                 470                 475                 480

Val Gly Gly Asn Val Gln Thr Leu Val Cys Arg Ser Trp Glu Ser Gly
                485                 490                 495

Glu Leu Tyr Glu Phe Val Asp Thr Pro Gly Asn Leu Pro Pro Ser Met
                500                 505                 510

Asn Leu Ser Tyr Ile Leu Gly Leu Arg Lys Asn Ile Ser Val Phe Gln
                515                 520                 525

Ala Tyr Arg Gln Cys Lys Ala Gly Thr Ala Leu Trp Lys Val Leu Gln
                530                 535                 540

Leu Asn Asp Ser Tyr Asp Leu Asp Lys His Leu Asp Ile Lys Gln Tyr
545                 550                 555                 560

Thr His Lys Leu Gln Gln Glu Leu Gln Ser Phe Lys Val Asp Leu Lys
                565                 570                 575

Asp Leu Asp Leu Leu Asn Pro Ala Ala Arg Gln Asn Leu Glu Ala Leu
                580                 585                 590

Gln Ser Ser Gly Leu Glu Lys Ile His Tyr Arg Asp Phe Leu Val Gln
                595                 600                 605

Ile Gln Lys Pro Val Val Lys Thr Asp Met Gly Gln Leu Ala Lys Glu
610                 615                 620

Leu Glu Gly Leu Ala Gln Ala His Asn Glu Ser Leu Arg Arg Gln Gln
625                 630                 635                 640

Leu Gln Glu Glu Ala Arg Glu Leu Arg Ser Leu Tyr Gln Glu Lys Val
                645                 650                 655

Val Pro Gln Glu Asn Leu Val Ala Lys Leu Asn Pro Ser Ile Arg Val
                660                 665                 670

Leu Glu Ser Ser Ala Pro Lys Leu Gln Val Asn Thr Ser Asp Leu Leu
                675                 680                 685

Asp Ile Val Ala Arg Leu Lys Gly Glu Leu Pro Ala Gln Leu Asn His
                690                 695                 700

Ile Leu Arg Asn Ala Thr Glu Cys Phe Leu Thr Arg Glu Met Gly Tyr
705                 710                 715                 720
```

```
Phe Ser Gln Tyr Val Thr Trp Val Arg Glu Val Thr Gln His Ile
            725                 730                 735

Ala Thr Cys Gln Pro Phe Ser Lys Ala Leu Asp Asp Gly His Met Ile
            740                 745                 750

Leu Cys Asp Met Met Gly Gln Pro Leu Glu Cys Leu Leu Val Leu Pro
        755                 760                 765

Gly Leu Val His Leu Leu Pro His Pro Gln His His Leu Arg Gly Gln
    770                 775                 780

Asp Leu Gln Val Leu Pro Ser His Pro Glu Thr Ala Gln Leu His Gln
785                 790                 795                 800

Leu Arg Arg Asp Thr Ala Leu Pro Tyr Pro Gln Gly His Leu Pro Glu
                805                 810                 815

Ala Ile Glu Pro Thr Gly Gln Gly Asp Thr Trp Gly Phe Pro Val Leu
            820                 825                 830

Leu Pro Cys Leu Ser Leu Asp Gln Thr Thr Ser Val Thr Ser Val Pro
            835                 840                 845

Glu Pro Arg Leu Ala Ser Ser Ala Gly Leu
        850                 855

<210> SEQ ID NO 22
<211> LENGTH: 806
<212> TYPE: PRT
<213> ORGANISM: Homo sapiens

<400> SEQUENCE: 22

Leu Ala Leu Ser Gln Leu Ala Ala Gly Ala Thr Asp Cys Lys Phe Leu
1               5                   10                  15

Gly Pro Ala Glu His Leu Thr Phe Thr Pro Ala Ala Arg Ala Arg Trp
            20                  25                  30

Leu Ala Pro Arg Val Arg Ala Pro Gly Leu Leu Asp Ser Leu Tyr Gly
        35                  40                  45

Thr Val Arg Arg Phe Leu Ser Val Gln Leu Asn Pro Phe Pro Ser
    50                  55                  60

Glu Leu Val Lys Ala Leu Leu Asn Glu Leu Ala Ser Val Lys Val Asn
65                  70                  75                  80

Glu Val Val Arg Tyr Glu Ala Gly Tyr Val Val Cys Ala Val Ile Ala
                85                  90                  95

Gly Leu Tyr Leu Leu Val Pro Thr Ala Gly Leu Cys Phe Cys Cys
    100                 105                 110

Cys Arg Cys His Arg Arg Cys Gly Gly Arg Val Lys Thr Glu His Lys
        115                 120                 125

Ala Leu Ala Cys Glu Arg Ala Ala Leu Met Val Phe Leu Leu Leu Thr
    130                 135                 140

Thr Leu Leu Leu Leu Ile Gly Val Val Cys Ala Phe Val Thr Asn Gln
145                 150                 155                 160

Arg Thr His Glu Gln Met Gly Pro Ser Ile Glu Ala Met Pro Glu Thr
                165                 170                 175

Leu Leu Ser Leu Trp Gly Leu Val Ser Asp Val Pro Gln Glu Leu Gln
            180                 185                 190

Ala Val Ala Gln Gln Phe Ser Leu Pro Gln Glu Gln Val Ser Glu Glu
        195                 200                 205

Leu Asp Gly Val Gly Val Ser Ile Gly Ser Ala Ile His Thr Gln Leu
    210                 215                 220

Arg Ser Ser Val Tyr Pro Leu Leu Ala Ala Val Gly Ser Leu Gly Gln
225                 230                 235                 240
```

-continued

Val Leu Gln Val Ser His His Leu Gln Thr Leu Asn Ala Thr Val
                245                 250                 255

Val Glu Leu Gln Ala Gly Gln Gln Asp Leu Glu Pro Ala Ile Arg Glu
            260                 265                 270

His Arg Asp Arg Leu Leu Glu Leu Leu Gln Glu Ala Arg Cys Gln Gly
        275                 280                 285

Asp Cys Ala Gly Ala Leu Ser Trp Ala Arg Thr Leu Glu Leu Gly Ala
    290                 295                 300

Asp Phe Ser Gln Val Pro Ser Val Asp His Val Leu His Gln Leu Lys
305                 310                 315                 320

Gly Val Pro Glu Ala Asn Phe Ser Ser Met Val Gln Glu Glu Asn Ser
                325                 330                 335

Thr Phe Asn Ala Leu Pro Ala Leu Ala Ala Met Gln Thr Ser Ser Val
            340                 345                 350

Val Gln Glu Leu Lys Lys Ala Val Ala Gln Pro Glu Gly Val Arg
        355                 360                 365

Thr Leu Ala Glu Gly Phe Pro Gly Leu Glu Ala Ala Ser Arg Trp Ala
    370                 375                 380

Gln Ala Leu Gln Glu Val Glu Ser Ser Arg Pro Tyr Leu Gln Glu
385                 390                 395                 400

Val Gln Arg Tyr Glu Thr Tyr Arg Trp Ile Val Gly Cys Val Leu Cys
                405                 410                 415

Ser Val Val Leu Phe Val Val Leu Cys Asn Leu Gly Leu Asn Leu
            420                 425                 430

Gly Ile Trp Gly Leu Ser Ala Arg Asp Pro Ser His Pro Glu Ala
        435                 440                 445

Lys Gly Glu Ala Gly Ala Arg Phe Leu Met Ala Gly Val Gly Leu Ser
450                 455                 460

Phe Leu Phe Ala Ala Pro Leu Ile Leu Val Phe Ala Thr Phe Leu
465                 470                 475                 480

Val Gly Gly Asn Val Gln Thr Leu Val Cys Gln Ser Trp Glu Asn Gly
                485                 490                 495

Glu Leu Phe Glu Phe Ala Asp Thr Pro Gly Asn Leu Pro Pro Ser Met
            500                 505                 510

Asn Leu Ser Gln Leu Leu Gly Leu Arg Lys Asn Ile Ser Ile His Gln
        515                 520                 525

Ala Tyr Gln Gln Cys Lys Glu Gly Ala Ala Leu Trp Thr Val Leu Gln
    530                 535                 540

Leu Asn Asp Ser Tyr Asp Leu Glu Glu His Leu Asp Ile Asn Gln Tyr
545                 550                 555                 560

Thr Asn Lys Leu Arg Gln Glu Leu Gln Ser Leu Lys Val Asp Thr Gln
                565                 570                 575

Ser Leu Asp Leu Leu Ser Ser Ala Ala Arg Arg Asp Leu Glu Ala Leu
            580                 585                 590

Gln Ser Ser Gly Leu Gln Arg Ile His Tyr Pro Asp Phe Leu Val Gln
        595                 600                 605

Ile Gln Arg Pro Val Val Lys Thr Ser Met Glu Gln Leu Ala Gln Glu
    610                 615                 620

Leu Gln Gly Leu Ala Gln Ala Gln Asp Asn Ser Val Leu Gly Gln Arg
625                 630                 635                 640

Leu Gln Glu Glu Ala Gln Gly Leu Arg Asn Leu His Gln Glu Lys Val
                645                 650                 655

Val Pro Gln Gln Ser Leu Val Ala Lys Leu Asn Leu Ser Val Arg Ala
            660                 665                 670

```
Leu Glu Ser Ser Ala Pro Asn Leu Gln Leu Glu Thr Ser Asp Val Leu
            675                 680                 685
Ala Asn Val Thr Tyr Leu Lys Gly Glu Leu Pro Ala Trp Ala Ala Arg
        690                 695                 700
Ile Leu Arg Asn Val Ser Glu Cys Phe Leu Arg Glu Met Gly Tyr
705                 710                 715                 720
Phe Ser Gln Tyr Val Ala Trp Val Arg Glu Glu Val Thr Gln Arg Ile
                725                 730                 735
Ala Thr Cys Gln Pro Leu Ser Gly Ala Leu Asp Asn Ser Arg Val Ile
            740                 745                 750
Leu Cys Asp Met Met Ala Asp Pro Trp Asn Ala Phe Trp Phe Cys Leu
        755                 760                 765
Ala Trp Cys Thr Phe Phe Leu Ile Pro Ser Ile Ile Phe Ala Val Lys
    770                 775                 780
Thr Ser Lys Tyr Phe Arg Pro Ile Arg Lys Arg Leu Ser Ser Thr Ser
785                 790                 795                 800
Ser Glu Glu Thr Gln Leu
                805

<210> SEQ ID NO 23
<211> LENGTH: 826
<212> TYPE: PRT
<213> ORGANISM: Homo sapiens

<400> SEQUENCE: 23

Leu Gly Leu Cys Gly Asn Ser Phe Ser Gly Gly Gln Pro Ser Ser Thr
1               5                   10                  15
Asp Ala Pro Lys Ala Trp Asn Tyr Glu Leu Pro Ala Thr Asn Tyr Glu
                20                  25                  30
Thr Gln Asp Ser His Lys Ala Gly Pro Ile Gly Ile Leu Phe Glu Leu
            35                  40                  45
Val His Ile Phe Leu Tyr Val Val Gln Pro Arg Asp Phe Pro Glu Asp
    50                  55                  60
Thr Leu Arg Lys Phe Leu Gln Lys Ala Tyr Glu Ser Lys Ile Asp Tyr
65                  70                  75                  80
Asp Lys Pro Glu Thr Val Ile Leu Gly Leu Lys Ile Val Tyr Tyr Glu
                85                  90                  95
Ala Gly Ile Ile Leu Cys Cys Val Leu Gly Leu Leu Phe Ile Ile Leu
            100                 105                 110
Met Pro Leu Val Gly Tyr Phe Phe Cys Met Cys Arg Cys Cys Asn Lys
        115                 120                 125
Cys Gly Gly Glu Met His Gln Arg Gln Lys Glu Asn Gly Pro Phe Leu
    130                 135                 140
Arg Lys Cys Phe Ala Ile Ser Leu Leu Val Ile Cys Ile Ile Ile Ser
145                 150                 155                 160
Ile Gly Ile Phe Tyr Gly Phe Val Ala Asn His Gln Val Arg Thr Arg
                165                 170                 175
Ile Lys Arg Ser Arg Lys Leu Ala Asp Ser Asn Phe Lys Asp Leu Arg
            180                 185                 190
Thr Leu Leu Asn Glu Thr Pro Glu Gln Ile Lys Tyr Ile Leu Ala Gln
        195                 200                 205
Tyr Asn Thr Thr Lys Asp Lys Ala Phe Thr Asp Leu Asn Ser Ile Asn
    210                 215                 220
Ser Val Leu Gly Gly Gly Ile Leu Asp Arg Leu Arg Pro Asn Ile Ile
225                 230                 235                 240
```

```
Pro Val Leu Asp Glu Ile Lys Ser Met Ala Thr Ala Ile Lys Glu Thr
            245                 250                 255
Lys Glu Ala Leu Glu Asn Met Asn Ser Thr Leu Lys Ser Leu His Gln
            260                 265                 270
Gln Ser Thr Gln Leu Ser Ser Leu Thr Ser Val Lys Thr Ser Leu
        275                 280                 285
Arg Ser Ser Leu Asn Asp Pro Leu Cys Leu Val His Pro Ser Ser Glu
        290                 295                 300
Thr Cys Asn Ser Ile Arg Leu Ser Leu Ser Gln Leu Asn Ser Asn Pro
305                 310                 315                 320
Glu Leu Arg Gln Leu Pro Pro Val Asp Ala Glu Leu Asp Asn Val Asn
                325                 330                 335
Asn Val Leu Arg Thr Asp Leu Asp Gly Leu Val Gln Gln Gly Tyr Gln
                340                 345                 350
Ser Leu Asn Asp Ile Pro Asp Arg Val Gln Arg Gln Thr Thr Thr Val
        355                 360                 365
Val Ala Gly Ile Lys Arg Val Leu Asn Ser Ile Gly Ser Asp Ile Asp
370                 375                 380
Asn Val Thr Gln Arg Leu Pro Ile Gln Asp Ile Leu Ser Ala Phe Ser
385                 390                 395                 400
Val Tyr Val Asn Asn Thr Glu Ser Tyr Ile His Arg Asn Leu Pro Thr
                405                 410                 415
Leu Glu Glu Tyr Asp Ser Tyr Trp Trp Leu Gly Gly Leu Val Ile Cys
                420                 425                 430
Ser Leu Leu Thr Leu Ile Val Ile Phe Tyr Tyr Leu Gly Leu Leu Cys
        435                 440                 445
Gly Val Cys Gly Tyr Asp Arg His Ala Thr Pro Thr Thr Arg Gly Cys
450                 455                 460
Val Ser Asn Thr Gly Gly Val Phe Leu Met Val Gly Val Gly Leu Ser
465                 470                 475                 480
Phe Leu Phe Cys Trp Ile Leu Met Ile Ile Val Val Leu Thr Phe Val
                485                 490                 495
Phe Gly Ala Asn Val Glu Lys Leu Ile Cys Glu Pro Tyr Thr Ser Lys
                500                 505                 510
Glu Leu Phe Arg Val Leu Asp Thr Pro Tyr Leu Leu Asn Glu Asp Trp
        515                 520                 525
Glu Tyr Tyr Leu Ser Gly Lys Leu Phe Asn Lys Ser Lys Met Lys Leu
        530                 535                 540
Thr Phe Glu Gln Val Tyr Ser Asp Cys Lys Lys Asn Arg Gly Thr Tyr
545                 550                 555                 560
Gly Thr Leu His Leu Gln Asn Ser Phe Asn Ile Ser Glu His Leu Asn
                565                 570                 575
Ile Asn Glu His Thr Gly Ser Ile Ser Ser Glu Leu Glu Ser Leu Lys
                580                 585                 590
Val Asn Leu Asn Ile Phe Leu Leu Gly Ala Ala Gly Arg Lys Asn Leu
        595                 600                 605
Gln Asp Phe Ala Ala Cys Gly Ile Asp Arg Met Asn Tyr Asp Ser Tyr
610                 615                 620
Leu Ala Gln Thr Gly Lys Ser Pro Ala Gly Val Asn Leu Leu Ser Phe
625                 630                 635                 640
Ala Tyr Asp Leu Glu Ala Lys Ala Asn Ser Leu Pro Pro Gly Asn Leu
                645                 650                 655
Arg Asn Ser Leu Lys Arg Asp Ala Gln Thr Ile Lys Thr Ile His Gln
```

```
                      660             665             670
Gln Arg Val Leu Pro Ile Glu Gln Ser Leu Ser Thr Leu Tyr Gln Ser
            675                 680                 685
Val Lys Ile Leu Gln Arg Thr Gly Asn Gly Leu Leu Glu Arg Val Thr
            690                 695                 700
Arg Ile Leu Ala Ser Leu Asp Phe Ala Gln Asn Phe Ile Thr Asn Asn
705                 710                 715                 720
Thr Ser Ser Val Ile Ile Glu Glu Thr Lys Lys Tyr Gly Arg Thr Ile
                725                 730                 735
Ile Gly Tyr Phe Glu His Tyr Leu Gln Trp Ile Glu Phe Ser Ile Ser
                740                 745                 750
Glu Lys Val Ala Ser Cys Lys Pro Val Ala Thr Ala Leu Asp Thr Ala
            755                 760                 765
Val Asp Val Phe Leu Cys Ser Tyr Ile Ile Asp Pro Leu Asn Leu Phe
770                 775                 780
Trp Phe Gly Ile Gly Lys Ala Thr Val Phe Leu Leu Pro Ala Leu Ile
785                 790                 795                 800
Phe Ala Val Lys Leu Ala Lys Tyr Tyr Arg Arg Met Asp Ser Glu Asp
                805                 810                 815
Val Tyr Asp Asp Val Glu Thr Ile Pro Met
                820                 825

<210> SEQ ID NO 24
<211> LENGTH: 853
<212> TYPE: PRT
<213> ORGANISM: Mus musculus

<400> SEQUENCE: 24

Leu Gly Leu Cys Gly Lys Ile Ser Ser Glu Gly Gln Pro Ala Phe His
1               5                   10                  15
Asn Thr Pro Gly Ala Met Asn Tyr Glu Leu Pro Thr Thr Lys Tyr Glu
            20                  25                  30
Thr Gln Asp Thr Phe Asn Ala Gly Ile Val Gly Pro Leu Tyr Lys Met
        35                  40                  45
Val His Ile Phe Leu Ser Val Val Gln Pro Asn Asp Phe Pro Leu Asp
    50                  55                  60
Leu Ile Lys Lys Leu Ile Gln Asn Lys Lys Phe Asp Ile Ser Val Asp
65                  70                  75                  80
Ser Lys Glu Pro Glu Ile Ile Val Leu Ala Leu Lys Ile Ala Leu Tyr
                85                  90                  95
Glu Ile Gly Val Leu Ile Cys Ala Ile Leu Gly Leu Leu Phe Ile Ile
            100                 105                 110
Leu Met Pro Leu Val Gly Cys Phe Phe Cys Met Cys Arg Cys Cys Asn
            115                 120                 125
Lys Cys Gly Gly Glu Met His Gln Arg Gln Lys Gln Asn Ala Pro Cys
        130                 135                 140
Arg Arg Lys Cys Leu Gly Leu Ser Leu Leu Val Ile Cys Leu Leu Met
145                 150                 155                 160
Ser Leu Gly Ile Ile Tyr Gly Phe Val Ala Asn Gln Gln Thr Arg Thr
                165                 170                 175
Arg Ile Lys Gly Thr Gln Lys Leu Ala Lys Ser Asn Phe Arg Asp Phe
            180                 185                 190
Gln Thr Leu Leu Thr Glu Thr Pro Lys Gln Ile Asp Tyr Val Val Glu
        195                 200                 205
Gln Tyr Thr Asn Thr Lys Asn Lys Ala Phe Ser Asp Leu Asp Gly Ile
```

-continued

```
            210                 215                 220
Gly Ser Val Leu Gly Arg Ile Lys Asp Gln Leu Lys Pro Lys Val
225                 230                 235                 240

Thr Pro Val Leu Glu Glu Ile Lys Ala Met Ala Thr Ala Ile Lys Gln
                    245                 250                 255

Thr Lys Asp Ala Leu Gln Asn Met Ser Ser Leu Lys Ser Leu Gln
                    260                 265                 270

Asp Ala Ala Thr Gln Leu Asn Thr Asn Leu Ser Ser Val Arg Asn Ser
                275                 280                 285

Ile Glu Asn Ser Leu Ser Ser Ser Asp Cys Thr Ser Asp Pro Ala Ser
290                 295                 300

Lys Ile Cys Asp Ser Ile Arg Pro Ser Leu Ser Ser Leu Gly Ser Ser
305                 310                 315                 320

Leu Asn Ser Ser Gln Leu Pro Ser Val Asp Arg Glu Leu Asn Thr Val
                325                 330                 335

Thr Glu Val Asp Lys Thr Asp Leu Glu Ser Leu Val Lys Arg Gly Tyr
                340                 345                 350

Thr Thr Ile Asp Glu Ile Pro Asn Thr Ile Gln Asn Gln Thr Val Asp
            355                 360                 365

Val Ile Lys Asp Val Lys Asn Thr Leu Asp Ser Ile Ser Ser Asn Ile
370                 375                 380

Lys Asp Met Ser Gln Ser Ile Pro Ile Glu Asp Met Leu Leu Gln Val
385                 390                 395                 400

Ser His Tyr Leu Asn Asn Ser Asn Arg Tyr Leu Asn Gln Glu Leu Pro
                    405                 410                 415

Lys Leu Glu Glu Tyr Asp Ser Tyr Trp Trp Leu Gly Gly Leu Ile Val
                    420                 425                 430

Cys Phe Leu Leu Thr Leu Ile Val Thr Phe Phe Phe Leu Gly Leu Leu
                435                 440                 445

Cys Gly Val Phe Gly Tyr Asp Lys His Ala Thr Pro Thr Arg Arg Gly
450                 455                 460

Cys Val Ser Asn Thr Gly Gly Ile Phe Leu Met Ala Gly Val Gly Phe
465                 470                 475                 480

Gly Phe Leu Phe Cys Trp Ile Leu Met Ile Leu Val Val Leu Thr Phe
                    485                 490                 495

Val Val Gly Ala Asn Val Glu Lys Leu Leu Cys Glu Pro Tyr Glu Asn
                500                 505                 510

Lys Lys Leu Leu Gln Val Leu Asp Thr Pro Tyr Leu Leu Lys Glu Gln
                515                 520                 525

Trp Gln Phe Tyr Leu Ser Gly Met Leu Phe Asn Asn Pro Asp Ile Asn
530                 535                 540

Met Thr Phe Glu Gln Val Tyr Arg Asp Cys Lys Arg Gly Arg Gly Ile
545                 550                 555                 560

Tyr Ala Ala Phe Gln Leu Glu Asn Val Val Asn Val Ser Asp His Phe
                    565                 570                 575

Asn Ile Asp Gln Ile Ser Glu Asn Ile Asn Thr Glu Leu Glu Asn Leu
                580                 585                 590

Asn Val Asn Ile Asp Ser Ile Glu Leu Leu Asp Asn Thr Gly Arg Lys
                595                 600                 605

Ser Leu Glu Asp Phe Ala His Ser Gly Ile Asp Thr Ile Asp Tyr Ser
            610                 615                 620

Thr Tyr Leu Lys Glu Thr Glu Lys Ser Pro Thr Glu Val Asn Leu Leu
625                 630                 635                 640
```

```
Thr Phe Ala Ser Thr Leu Glu Ala Lys Ala Asn Gln Leu Pro Glu Gly
                645                 650                 655

Lys Pro Lys Gln Ala Phe Leu Leu Asp Val Gln Asn Ile Arg Ala Ile
            660                 665                 670

His Gln His Leu Leu Pro Pro Val Gln Gln Ser Leu Asn Thr Leu Arg
        675                 680                 685

Gln Ser Val Trp Thr Leu Gln Gln Thr Ser Asn Lys Leu Pro Glu Lys
    690                 695                 700

Val Lys Lys Ile Leu Ala Ser Leu Asp Ser Val Gln His Phe Leu Thr
705                 710                 715                 720

Asn Asn Val Ser Leu Ile Val Ile Gly Glu Thr Lys Lys Phe Gly Lys
                725                 730                 735

Thr Ile Leu Gly Tyr Phe Glu His Tyr Leu His Trp Val Phe Tyr Ala
            740                 745                 750

Ile Thr Glu Lys Met Thr Ser Cys Lys Pro Met Ala Thr Ala Met Asp
        755                 760                 765

Ser Ala Val Asn Gly Ile Leu Cys Gly Tyr Val Ala Asp Pro Leu Asn
    770                 775                 780

Leu Phe Trp Phe Gly Ile Gly Met Asp Ser Ala Val Asn Gly Ile Leu
785                 790                 795                 800

Cys Gly Tyr Val Ala Asp Pro Leu Asn Leu Phe Trp Phe Gly Ile Gly
                805                 810                 815

Lys Ala Thr Val Leu Leu Pro Ala Val Ile Ala Ile Lys Leu
            820                 825                 830

Ala Lys Tyr Tyr Arg Arg Met Asp Ser Glu Asp Val Tyr Asp Asp Val
        835                 840                 845

Glu Thr Val Pro Met
    850

<210> SEQ ID NO 25
<211> LENGTH: 826
<212> TYPE: PRT
<213> ORGANISM: Caenorhabditis elegans

<400> SEQUENCE: 25

Tyr Leu Thr Ile Ile Val Gly Phe Thr Cys Ala Asp Leu Val Phe Ser
1               5                   10                  15

Pro Tyr Lys Ser Ala Glu Gln Tyr Lys Cys Gly Ser Phe Met Glu Asp
                20                  25                  30

Arg Asn Gly Arg Lys Ala Asp Ala Val Leu Ser Phe Tyr Tyr Thr Thr
            35                  40                  45

Ile Asp Gln Phe Ile Thr Phe Val Ser Tyr Pro Phe Pro His Gln Glu
        50                  55                  60

Leu Leu Asn Asp Gln Ala Leu Thr Gly Asp Leu Val Glu Leu Gln Ser
65                  70                  75                  80

Ser Val Glu Lys Lys Tyr Trp Gln Trp Ile Glu Phe Gln Lys Gly Trp
                85                  90                  95

Ile Val Leu Ser Val Gly Leu Val Ala Ile Ser Val Leu Phe Val Val
            100                 105                 110

Phe Tyr Phe Phe Tyr Lys Cys Cys Val Cys Ile Cys Ser Arg Ser Ser
        115                 120                 125

Lys Lys Gln Asn Thr Asp Ala Arg Tyr Asp Gly Cys Lys Arg Ser Met
    130                 135                 140

Cys Asn Leu Leu Leu Phe Val Leu Val Ser Ala Asn Ala Phe Val Ala
145                 150                 155                 160
```

-continued

Phe Thr Leu Leu Met Thr Ser Gln Tyr Ala Gln Ile Gly Leu Asp Lys
            165                 170                 175

Leu Pro Asn Arg Met Asn Gln Cys Val Asp Asp Leu Gln Ser Tyr Lys
        180                 185                 190

Arg Asp Ser Asp Met Arg Ile Arg Lys Leu Leu Ile Asp Asp Tyr Gln
    195                 200                 205

Val Leu Asn Ser Thr Ile Thr Lys Gln Leu Ser Thr Ala Gly Tyr Asn
210                 215                 220

Val Val Asp Arg Val Lys Lys Leu Thr Gly Ala His Val Ile Asp Val
225                 230                 235                 240

Phe Met Asn Ile Ser Lys Val Ala Gln Glu Met His Asp Gly Leu Glu
                245                 250                 255

Ser Val His Gly Lys Val Arg Phe Leu Asn Glu Glu Gly Ser Arg Phe
            260                 265                 270

Glu Ala Glu Phe Ser Arg Leu Arg Asn Thr Ala Asn Glu Glu Leu Val
        275                 280                 285

Lys Cys Leu Glu Asn Glu Leu Glu Pro Val Arg Ser Met Cys Ala Lys
    290                 295                 300

Ala Glu Arg Leu Leu Glu Ser Leu Ala Val Thr Gln Phe Lys Ile Asp
305                 310                 315                 320

Gln Lys Phe Leu Pro Asp Ala Thr Glu Thr Gly Leu Ser Glu Ile Val
                325                 330                 335

Asn Ala Asn Ile Thr Gln Val Leu Ala Ala Ser Asn Gln Phe Glu
            340                 345                 350

Gln Leu Glu Ser Arg Ile Gln His Glu Ile Asp Lys Glu Thr Tyr Ser
        355                 360                 365

Ala Gln Asn Met Leu Lys Gln Ile Gly Asp Asp Leu Phe Leu Val Ala
370                 375                 380

Glu Thr Ile Ser Thr Gln Leu Arg Lys Val Thr Phe Glu Ala Leu Tyr
385                 390                 395                 400

Ser Thr Val Ser Tyr Val Ser Asp Pro Lys Lys Thr Pro Thr Leu Lys
                405                 410                 415

Tyr Met Gln Tyr Ser Trp Tyr Ala Ser Leu Val Ile Thr Ser Leu Phe
            420                 425                 430

Ile Leu Leu Ala Leu Ile Phe Leu Phe Gly Val Leu Tyr Gly Ile Cys
        435                 440                 445

Gly Arg Arg Pro Thr Tyr Tyr Asn Asp Asp Cys Cys Val Arg Ser Thr
    450                 455                 460

Gly Gly Lys Phe Tyr Ser Phe Gly Ile Gly Ala Phe Leu Leu Ile Phe
465                 470                 475                 480

Val Phe Leu Ala Val Gly Thr Ser Ala Leu Met Phe Ala Val Gly Asn
                485                 490                 495

Phe Ser Asn Leu Val Cys Gln Pro Met Arg Asn Pro Leu Ser His Pro
            500                 505                 510

Glu Ser Leu Ser Leu Ala Asp Arg Tyr Ile Asn Leu Trp Lys Ala Asn
        515                 520                 525

His Thr Pro Glu Asn Asp Ile Glu Val Thr Leu Gln Ser Lys Ser Pro
    530                 535                 540

Ala Glu Ile Ile Arg Ala Cys Ser Arg Asn Glu Thr Leu Tyr Asn Phe
545                 550                 555                 560

Tyr Gly Phe Asp Lys Lys Tyr His Leu Asn Lys Leu Gln Asp Phe Glu
                565                 570                 575

Lys Asp Ala Tyr Asn Gln Leu Gln Ile Ser Leu Arg Thr Met Glu
            580                 585                 590

Asn Met Pro Glu Ile Arg Pro Leu Asp Ala Phe Ile Ser Arg Ser Glu
            595                 600                 605

Leu Arg Asp Leu Glu Lys Leu Ala Ser Val Asn Val Ser Lys Val Ser
610                 615                 620

Gln Gln Gly Leu Asn Ala Ile Lys His Ala Met Asp Glu Leu Asp Leu
625                 630                 635                 640

Ala Ser Lys Thr Arg Glu Phe Glu Ser Leu Asp Ala Asn Ser Gly
            645                 650                 655

Arg Pro Lys Ala Val Thr Leu Val Leu Glu Gln Ile Arg Glu Leu Glu
            660                 665                 670

Ile Gln Phe Ala Lys Pro Leu Arg Ser Arg Leu Glu Ala Leu Tyr Ser
            675                 680                 685

Asn Ile Thr Ser Leu Asp Glu Lys Leu Ser Gln Leu Gln Val Pro Val
            690                 695                 700

Ser Ser Leu Leu Val Lys Leu Gln His Ala Gln Ala Leu Leu Ala Glu
705                 710                 715                 720

Asn Met Arg Glu His Phe Gly Arg Ala Ala Lys Glu Glu Phe Gln Gln
            725                 730                 735

Met Val Asn Asn Ile Asp Gln Tyr Ile Val His Val Lys Ser Gln Met
            740                 745                 750

Glu Ser Glu Val Thr Ser Cys Gln Pro Leu Thr Gln Ile Ala Arg Gln
            755                 760                 765

Thr Thr Ala Ala Val Cys Ala Tyr Thr Ile Asp Pro Tyr Asn Gly Thr
770                 775                 780

Trp Met Cys Met Leu Ile Cys Leu Val Leu Leu Ile Pro Ile Val Ile
785                 790                 795                 800

Ile Ser Asn Ser Leu Ile Gly Leu Tyr Ser Lys Met His Ala Phe Pro
            805                 810                 815

Lys Tyr Ile Val Glu Pro Pro Ser Glu Thr
            820                 825

<210> SEQ ID NO 26
<211> LENGTH: 826
<212> TYPE: PRT
<213> ORGANISM: Drosophila melanogaster

<400> SEQUENCE: 26

Val Gly His Gly Thr Thr His Glu Gln Leu Gly Gln Pro His Trp Pro
1               5                   10                  15

Pro Val Gln Tyr Thr Val Tyr Arg Pro Thr Thr Asn Tyr Thr Lys Ala
            20                  25                  30

Pro Pro Pro Pro Thr Ser Ala Met Asn Pro Ile Phe Asn Phe Thr His
            35                  40                  45

Phe Leu Tyr Asp Lys Val Leu Tyr Arg Asp Glu Pro Ile Pro Glu Gly
50                  55                  60

Tyr Ile Val Val Lys Asn Ser Asp Thr Leu Ser Leu Gly Pro Lys Val
65                  70                  75                  80

Glu Glu Asn Asp Trp Arg Asp Leu Leu Ala His Tyr Trp Met Val Leu
            85                  90                  95

Ile Trp Val Val Ile Leu Val Val Leu Ile Ile Val Ile Pro Phe Ile
            100                 105                 110

Ala Val Cys Tyr Cys Cys Phe Cys Cys Cys Arg Arg Cys Arg Gln Gly
            115                 120                 125

Cys Pro Pro Cys Thr Ser Lys Gln Asp Ala Gln Arg Arg Phe Cys Cys
130                 135                 140

-continued

```
Gly Ile Cys Leu Leu Ile Leu Ile Ile Gly Leu Ile Phe Gly Ile Ile
145                 150                 155                 160

Ile Ala Phe Val Thr Asn Lys Met Ile Asp Ser Gly Phe Ala Glu Thr
                165                 170                 175

Ser Glu Thr Met Lys Arg Gly Ser Glu Asp Thr Cys Thr Tyr Leu Lys
            180                 185                 190

Asp Val Ala Asp His Val His His Leu Met Met Tyr Asn Tyr Glu Glu
        195                 200                 205

Met Glu Thr His Val Leu Asp Gln Leu Thr His Ala His Arg His Ile
    210                 215                 220

Phe Leu Asp Leu Ser Asp Thr Ser Glu Ser Asn Ser Leu Ala Glu Met
225                 230                 235                 240

Glu Arg Val Leu Glu Asn Met Pro Glu Ala Leu Glu Leu Met Arg Gln
                245                 250                 255

Val Glu Lys Met Glu Lys Asp Leu Arg Phe Tyr Gly Ser Gln Leu Arg
                260                 265                 270

Asp Gly Val Arg Gly Ile Lys Arg Asp Val Asn Phe Ala Val Ala Asn
            275                 280                 285

Leu Cys Gln Leu Gln Met Cys Gln Lys Phe Leu Ile Ser Ser Asn Ile
        290                 295                 300

Glu His Ile Asp Ser Ser Gln Cys Leu His Phe Asp Asn Leu Pro Asn
305                 310                 315                 320

Thr Lys Glu Phe Val Glu Gly Met Glu Asn Ile Val Ala Ser Glu Tyr
                325                 330                 335

Tyr Ala Ile Pro Gln Arg Gly Leu Ser Arg Leu Lys Lys Val Ser Asp
                340                 345                 350

Lys Val Lys Thr Gln Leu Ser Phe Val Val Pro Pro Met Met Arg Asp
            355                 360                 365

Leu Thr Lys Gly Arg Thr Ile Phe Arg Glu His Ala Thr Asn Val Arg
        370                 375                 380

Asn Ile Val Glu Gly Val Leu Ser Asp Ile His Ile Lys Thr Leu His
385                 390                 395                 400

Ser Thr Lys Ser Phe Glu Asp Val Tyr Glu Arg Phe Gly His Asp Arg
                405                 410                 415

Asn Val Val Ser Leu Ile Val Cys Leu Leu Ile Leu Leu Val Leu Phe
                420                 425                 430

Ile Leu Ile Phe Ala Leu Leu Cys Gly Cys Phe Gly Arg Arg Arg Thr
            435                 440                 445

Gly Tyr Gly Asp Glu Cys Cys Ser Lys Ser Thr Gly Ala Thr Cys Leu
        450                 455                 460

Leu Leu Ala Ile Leu Ile Phe Cys Val Phe Ser Phe Ile Ala Leu
465                 470                 475                 480

Val Gly Leu Phe Tyr Phe Met Leu Gly Met Val Thr Tyr Gln Gly Ala
                485                 490                 495

Cys Ala Pro Leu Arg Asp Gln Glu Asn Asn Thr Leu Phe Arg Gln Leu
                500                 505                 510

Asp Ala Ser Ile Asp Leu Asn His Tyr Leu Pro Pro Ser Glu Ser Asn
            515                 520                 525

Lys Glu Val Val Gln Pro Leu Lys Met Ser Ser Ala Ile Lys Ala Cys
        530                 535                 540

His Ala Asn Gln Thr Ile Phe Asp Met Met Arg Gln His Asn Ile Tyr
545                 550                 555                 560

Asp Ile Asn Asp Leu Thr Arg Ile Lys Val Met Ser His Ser Gln Glu
```

```
                565                 570                 575
Asn Thr Asp Ser Ile Lys Val Phe Asp Glu Asp Leu Ser Thr Val Val
            580                 585                 590
Leu Leu Thr Lys Glu Glu Arg Asp Glu Leu Lys Thr Ala Gly Glu Ser
            595                 600                 605
Lys Leu Ala Lys Tyr His Ser Ser Leu Tyr Met Pro Ser Leu Cys Thr
            610                 615                 620
Gln Phe Thr Pro Met Asn Leu Asn Ala Leu Ser Glu Gln Leu Tyr Lys
625                 630                 635                 640
Leu Ser Asn Asp Leu Glu Tyr Pro Ala Tyr Gly Trp Ala Lys Val Ser
                645                 650                 655
Phe Trp Asn Glu Gly Leu Asn Thr Lys Ala Phe Tyr Arg Asn Phe Val
                660                 665                 670
Pro Lys Leu Thr Ser Leu Val Glu Lys Met Lys Ala Asn Leu Lys Lys
                675                 680                 685
Ile Asp Glu Leu Ile Ser Tyr Glu Asn His Asp Phe Thr Asn Thr Ile
            690                 695                 700
Lys Ile Leu Thr Ala Thr Ala Ile Asn Ser Glu Gln Phe Ile Gln Thr
705                 710                 715                 720
Arg Gly Lys Asp Tyr Ile Asn Ala Leu Gly Gly Asn Leu Thr Asn Ser
                725                 730                 735
Ile Asp Gln Met Ile Asp Asp Tyr Ile Asp Met Ile Lys Glu Ala
            740                 745                 750
Asn Glu Ser Val Gly His Cys Ala Pro Leu Ser Tyr Ile Tyr Arg
                755                 760                 765
Gly Val Asp Leu Ile Cys His Arg Ile Val Asp Pro Ile Asn Gly Phe
            770                 775                 780
Trp Val Gly Ile Leu Leu Cys Ala Leu Leu Phe Leu Pro Ile Leu Phe
785                 790                 795                 800
Val Ala His Arg Leu Met Cys Leu Tyr Lys Lys Ile Tyr Pro Tyr Leu
                805                 810                 815
Ala Thr Val Gly Ala Ala Gly Val Val Glu
            820                 825

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Val Gln Arg Gln Thr Thr Thr Val Val Ala Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Gln Arg Gln Thr Thr Thr Val Val Ala Gly Ile
1               5                   10

<210> SEQ ID NO 29
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Arg Gln Thr Thr Thr Val Val Ala Gly Ile Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Gln Thr Thr Thr Val Val Ala Gly Ile Lys Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Thr Thr Thr Val Val Ala Gly Ile Lys Arg Val
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Asp Arg Val Gln Arg Gln Thr Thr Thr Val Val
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Pro Asp Arg Val Gln Arg Gln Thr Thr Thr Val
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ile Pro Asp Arg Val Gln Arg Gln Thr Thr Thr
```

```
                1               5                   10
```

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Asn Asp Ile Pro Asp Arg Val Gln Arg Gln Thr Thr Thr
1               5                   10
```

<210> SEQ ID NO 36
<211> LENGTH: 865
<212> TYPE: PRT
<213> ORGANISM: Homo sapiens

<400> SEQUENCE: 36

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300
```

```
Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
                580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
```

```
                    725                 730                 735
Glu Glu Thr Lys Lys Tyr Gly Arg Thr Ile Ile Gly Tyr Phe Glu His
                    740                 745                 750

Tyr Leu Gln Trp Ile Glu Phe Ser Ile Ser Glu Lys Val Ala Ser Cys
                755                 760                 765

Lys Pro Val Ala Thr Ala Leu Asp Thr Ala Val Asp Val Phe Leu Cys
            770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
                820                 825                 830

Thr Ile Pro Met Lys Asn Met Glu Asn Gly Asn Asn Gly Tyr His Lys
                835                 840                 845

Asp His Val Tyr Gly Ile His Asn Pro Val Met Thr Ser Pro Ser Gln
                850                 855                 860

His
865

<210> SEQ ID NO 37
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass 0
      to 20 residues
<220> FEATURE:
<221> NAME/KEY: MOD_RES
<222> LOCATION: (34)..(53)
<223> OTHER INFORMATION: Any amino acid and this region may encompass 0
      to 20 residues
<220> FEATURE:
<223> OTHER INFORMATION: see specification as filed for detailed
      description of substitutions and preferred embodiments

<400> SEQUENCE: 37

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Asp Arg Val Gln Arg Gln Thr Thr Thr Val Val
                20                  25                  30

Ala Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Cys
    50

<210> SEQ ID NO 38
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(22)
<223> OTHER INFORMATION: Any amino acid and this region may encompass 0
      to 20 residues
<220> FEATURE:
<221> NAME/KEY: MOD_RES
```

```
<222> LOCATION: (35)..(54)
<223> OTHER INFORMATION: Any amino acid and this region may encompass 0
      to 20 residues
<220> FEATURE:
<223> OTHER INFORMATION: see specification as filed for detailed
      description of substitutions and preferred embodiments

<400> SEQUENCE: 38

Ala Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp Arg Val Gln Arg Gln Thr Thr Thr Val
            20                  25                  30

Val Ala Xaa Xaa Xaa Xaa Xaa Xaa Xaa Xaa Xaa Xaa Xaa Xaa
        35                  40                  45

Xaa Xaa Xaa Xaa Xaa Xaa Cys
    50                  55

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Val Gln Arg Gln Thr Thr Thr Val Val Ala
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ala Val Gln Arg Gln Thr Thr Thr Val Val Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Arg Ala Gln Arg Gln Thr Thr Thr Val Val Ala
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Arg Val Ala Arg Gln Thr Thr Thr Val Val Ala
1               5                   10

<210> SEQ ID NO 43
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Arg Val Gln Ala Gln Thr Thr Thr Val Val Ala
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Val Gln Arg Ala Thr Thr Thr Val Val Ala
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Arg Val Gln Arg Gln Ala Thr Thr Val Val Ala
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Arg Val Gln Arg Gln Thr Ala Thr Val Val Ala
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Arg Val Gln Arg Gln Thr Thr Thr Ala Val Ala
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Arg Val Gln Arg Gln Thr Thr Thr Val Ala Ala
1               5                   10
```

```
<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Arg Val Gln Arg Gln Thr Thr Thr Val Val Ala
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Arg Val Gln Arg Gln Thr Thr Thr Val Val Gly
1               5                   10

<210> SEQ ID NO 51
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass 0
      to 20 residues
<220> FEATURE:
<221> NAME/KEY: MOD_RES
<222> LOCATION: (26)..(26)
<223> OTHER INFORMATION: Any naturally occurring amino acid or
      derivative thereof
<220> FEATURE:
<221> NAME/KEY: MOD_RES
<222> LOCATION: (34)..(53)
<223> OTHER INFORMATION: Any amino acid and this region may encompass 0
      to 20 residues
<220> FEATURE:
<223> OTHER INFORMATION: see specification as filed for detailed
      description of substitutions and preferred embodiments

<400> SEQUENCE: 51

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Asp Arg Val Gln Xaa Gln Thr Thr Thr Val Val
            20                  25                  30

Ala Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Cys
    50

<210> SEQ ID NO 52
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (3)..(22)
<223> OTHER INFORMATION: Any amino acid and this region may encompass 0
      to 20 residues
<220> FEATURE:
<221> NAME/KEY: MOD_RES
<222> LOCATION: (27)..(27)
<223> OTHER INFORMATION: Any naturally occurring amino acid or
      derivative thereof
<220> FEATURE:
<221> NAME/KEY: MOD_RES
<222> LOCATION: (35)..(54)
<223> OTHER INFORMATION: Any amino acid and this region may encompass 0
      to 20 residues
<220> FEATURE:
<223> OTHER INFORMATION: see specification as filed for detailed
      description of substitutions and preferred embodiments

<400> SEQUENCE: 52

Ala Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp Arg Val Gln Xaa Gln Thr Thr Thr Val
            20                  25                  30

Val Ala Xaa Xaa Xaa Xaa Xaa Xaa Xaa Xaa Xaa Xaa Xaa Xaa
        35                  40                  45

Xaa Xaa Xaa Xaa Xaa Xaa Cys
    50                  55

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ala Val Val Thr Thr Thr Gln Arg Gln Val Arg Asp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any naturally occurring amino acid or
      derivative thereof

<400> SEQUENCE: 54

Asp Arg Val Gln Xaa Gln Thr Thr Thr Val Val Ala
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Cys Gly Asn Ser Phe Ser Gly Gly Gln Pro Ser
1               5                   10

<210> SEQ ID NO 56
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Cys Ala Asn Ser Phe Ser Gly Gly Gln Pro Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Cys Gly Asn Ser Phe Ser Ala Gly Gln Pro Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Cys Gly Asn Ser Phe Ser Gly Ala Gln Pro Ser
1               5                   10

<210> SEQ ID NO 59
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: Any amino acid and this region may encompass 0
      to 20 residues
<220> FEATURE:
<221> NAME/KEY: MOD_RES
<222> LOCATION: (25)..(25)
<223> OTHER INFORMATION: Any naturally occurring amino acid or
      derivative thereof
<220> FEATURE:
<221> NAME/KEY: MOD_RES
<222> LOCATION: (33)..(52)
<223> OTHER INFORMATION: Any amino acid and this region may encompass 0
      to 20 residues
<220> FEATURE:
<223> OTHER INFORMATION: see specification as filed for detailed
      description of substitutions and preferred embodiments

<400> SEQUENCE: 59

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Asp Arg Val Gln Xaa Gln Thr Thr Thr Val Val Ala
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa
    50
```

```
<210> SEQ ID NO 60
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: Any amino acid and this region may encompass 0
      to 20 residues
<220> FEATURE:
<221> NAME/KEY: MOD_RES
<222> LOCATION: (25)..(25)
<223> OTHER INFORMATION: Any naturally occurring amino acid or
      derivative thereof
<220> FEATURE:
<221> NAME/KEY: MOD_RES
<222> LOCATION: (33)..(52)
<223> OTHER INFORMATION: Any amino acid and this region may encompass 0
      to 20 residues
<220> FEATURE:
<223> OTHER INFORMATION: see specification as filed for detailed
      description of substitutions and preferred embodiments

<400> SEQUENCE: 60

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Asp Arg Val Gln Xaa Gln Thr Thr Thr Val Val Ala
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa
    50
```

PROMININ-1 PEPTIDE FRAGMENTS AND USES THEREOF

CROSS REFERENCE TO RELATED APPLICATIONS

This application is a continuation-in-part of the International Application Serial No. PCT/US2009/051971, filed on Jul. 28, 2009, which claims benefit under 35 U.S.C. §119(e) of U.S. provisional application 61/084,052 filed Jul. 28, 2008, both of which are incorporated herein by reference in their entirety.

SEQUENCE LISTING

The instant application contains a Sequence Listing which has been submitted in ASCII format via EFS-Web and is hereby incorporated by reference in its entirety. The ASCII copy, created on Feb. 25, 2011, is named 20110414_SequenceListing_Text_701039_061942_CIP.txt and is 81,086 bytes in size.

FIELD OF THE INVENTION

The field of the invention relates to the field of regeneration and the modulation of the biological effects of pro-angiogenic factors.

BACKGROUND OF INVENTION

Angiogenesis is the formation, development and growth of new blood vessels. The normal regulation of angiogenesis is governed by a fine balance between factors that induce the formation of blood vessels and those that halt or inhibit the process. When this balance is upset, it generally results in pathological angiogenesis. A great number of pathologies arise from either an excess of angiogenesis or, conversely, an insufficient angiogenesis. Regulating angiogenesis with angiogenic (for insufficient angiogenesis) or angiostatic (for excessive angiogenesis) factors is therefore of great therapeutic interest in a number of medical fields such as ophthalmology, oncology and dermatology. Regulation of angiogenesis can provide approaches for the treatment of vascular diseases, for example, diseases characterized by poor capillarity and/or neurogenesis, including stroke, coronary artery disease, peripheral muscle impairment associated with chronic obstructive pulmonary disease, wound healing, and Alzheimer's disease.

SUMMARY OF THE INVENTION

Embodiments of the present invention are based on the discoveries that short peptides derived from a penta span transmembrane glycoprotein have distinct effects on angiogenesis. The inventors found that short peptides from prominin-1 (prom-1) bind VEGF (see table 1), an endogenous pro-angiogenesis factor that is important for normal growth and development but is also involved during unwanted and aberrant vascularization such as in cancer and diabetic retinopathy. In addition, the short peptides promoted VEGF binding to other cell types, promoted proliferation of endothelial cells in vitro, and enhanced angiogenesis and cell migration in the presence of VEGF. These short peptides with regenerative and/or pro-angiogenic properties are useful in promoting angiogenesis, such as in wound healing, burns, tissue repair, fertility treatments, myocardial infarction, hypertrophied hearts, revascularization of tissue after disease and trauma (e.g., stroke, ischemic limbs, vascular diseases, bone repair), tissue grafts and tissue engineered constructs. Further, because the peptides and peptide derivatives described herein potentiate the effects of VEGF, they are also to be considered for their effects on other activities mediated by VEGF. For example, VEGF is a neurotrophic factor that exhibits neuroprotective properties. The peptides and derivatives described herein are also useful for promoting nerve growth, neuroprotection, vasodilation, modulation of blood pressure, and treatment of erectile dysfunction.

In one embodiment, provided herein is an isolated peptide fragment of a prominin-1 (prom-1), the peptide having regenerative, pro-angiogenic activity and/or VEGF-binding activity as measured by, for example, an in vitro ELISA-based VEGF-binding assay.

In one embodiment, provided herein is an isolated peptide fragment of a prominin polypeptide, the peptide having regenerative and/or pro-angiogenic activity and also binds to a pro-angiogenic factor.

In one embodiment, provided herein is an isolated peptide fragment of a prominin polypeptide, the peptide having regenerative and/or pro-angiogenic activity and also stimulates endothelial cell proliferation.

In one embodiment, provided herein is an isolated peptide fragment of an extracellular domain of a prominin polypeptide, wherein the peptide has regenerative and/or pro-angiogenic activity.

In one embodiment, provided herein is isolated peptide fragments of a prominin polypeptide homologue. Homologs of prom-1 are found in zebrafish, Norway rat, house mouse, humans, nematode and fruit fly. In a particular embodiment, the prominin is human prominin-1 (Genbank Accession No.: NM_006017.1; NP_006008.1; AF027208.1; SEQ ID NO: 36).

In some embodiments, the isolated peptide fragments of prom-1 described herein are derived from the extracellular domain set forth in SEQ. ID. No. 1, 2, or 3.

In some embodiments, the isolated peptide fragments of prom-1 described herein comprise at least 6 amino acid residues, wherein the peptide does not include a full-length prominin polypeptide.

In some embodiments, the isolated peptide fragments of prom-1 described herein are conservative amino acid substitution variants. To the extent that a peptide is 12 amino acids or less, such peptides are at least 60% identical to a peptide fragment of prom-1, wherein the peptide variants bind VEGF and have regenerative and/or pro-angiogenic activity as measured by an angiogenesis assay described herein. Further, to the extent that it is known that a given amino acid residue of a prom-1 peptide is critical for or implicated in binding, e.g., by mutagenesis or deletion assays, in one embodiment that amino acid residue is not substituted. It is specifically contemplated, however, that some substitutions at such residues may actually enhance binding. Thus, one of skill in the art should consider carefully before modifying such amino acids. Substitutions or modifications to residues of this kind that maintain or enhance binding to VEGF or the biological properties of VEGF are also encompassed within the scope of the terms "variant" and "derivative" as used in reference to prom-1 peptides.

In one embodiment, the isolated peptide fragment of a prominin polypeptide, the peptide having regenerative, pro-angiogenic activity and/or VEGF-binding activity as measured by an in vitro ELISA-based VEGF-binding assay, comprises at least 6 consecutive amino acid residues from e.g., SEQ ID NOs: 1, 2, or 3. While any fragment of prom-1 that has regenerative and/or pro-angiogenic activity is contemplated, fragments of 30 amino acids or less, down to a minimum of 6 amino acids, e.g., 29, 28, 27, 26, 25, 24, 23, 22, 21, 20, 19, 18, 17, 16, 15, 14, 13, 12, 11, 10, 9, 8, 7, or 6 amino acid residues are of particular interest. Preferably, the isolated peptide is selected from the group consisting of LCGNSF-SGGQPS (SEQ. ID. No. 4); PNIIPVLDEIKS (SEQ. ID. No. 5); LCGVCGYDRHAT (SEQ. ID. No. 6); ITNNTSSVIIEE (SEQ. ID. No. 7); DRVQRQTTTVVA (SEQ. ID. No. 8); and CSFAYDLEAKANSLPPGNLRN (SEQ. ID. No. 9) or a conservative amino acid substitution variant thereof that substantially retains regenerative, pro-angiogenic activity and/or VEGF-binding activity. These peptides dramatically enhance angiogenesis in vivo and enhance cell migration in the presence of VEGF.

Alternatively, or in addition, such peptides or variants or derivatives thereof encompassed by the various embodiments described herein can bind VEGF and exhibit neuroprotective properties.

In one embodiment, the isolated peptide is a VEGF-binding conservative substitution variant of a peptide fragment of prominin-1, the peptide having regenerative and/or pro-angiogenic activity. The peptide can have one, two, three or more conservative amino acid substitutions. The variant peptide retains a pro-angiogenic activity that is at least 50% of the original non-substituted parent peptide as measured by an in vitro ELISA-based VEGF-binding assay.

In another embodiment, the isolated peptide having VEGF-binding and regenerative and/or pro-angiogenic activities is fused with a non-prominin-1 protein, or a heterologous peptide or protein, forming a fusion protein comprising a peptide fragment of a prominin-1.

In yet another embodiment, the isolated peptide is a peptide mimetic of an isolated prom-1 peptide having regenerative and/or pro-angiogenic activities and binds VEGF.

In yet another embodiment, the isolated peptide having VEGF-binding, regenerative and/or pro-angiogenic activities is conjugated to a compound such as a polymer, e.g., for the purpose of improving serum half and pharmacokinetics in vivo. In another embodiment, the isolated peptide having VEGF-binding, regenerative and/or pro-angiogenic activities is fused to another protein or a portion of a protein for the purpose of improving serum half-life and pharmacokinetics in vivo, for improved recombinant protein expression and purification, and/or increased potency of angiogenic activity. The isolated peptide having VEGF-binding, regenerative and/or pro-angiogenic activities is present in the context of a fusion protein. In one embodiment, the peptide is PEGylated.

The isolated peptide, variant, fusion protein, peptide mimetic or conjugate described herein enhances VEGF binding to endothelial cells, enhances cell proliferation, enhances angiogenesis in the presence of pro-angiogenic factors, and enhances cell migration in the presence of pro-angiogenic factors.

In one embodiment, the isolated peptide, variant, fusion protein, peptide mimetic or conjugate described herein has neuroprotective activity. In another embodiment, the isolated peptide, variant, fusion protein, peptide mimetic or conjugate described herein prevents or delays neuronal cell death relative to neuronal cell death occurring in the absence of the isolated peptide, variant, fusion protein, peptide mimetic or conjugate described herein. In another embodiment, the isolated peptide, variant, fusion protein, peptide mimetic or conjugate described herein promotes nerve regeneration by stimulating neuronal growth.

In one embodiment, described herein is a composition comprising a pharmaceutically acceptable carrier and an isolated peptide, variant, fusion protein, peptide mimetic or conjugate as described herein.

In one embodiment, a method or use for promoting cell proliferation in a tissue in need thereof is provided, the method comprising contacting the tissue with a composition comprising an isolated peptide, variant, peptide mimetic or conjugate thereof.

In one embodiment, one first identifies a tissue in need of e.g., cell proliferation, and then contacts the tissue with a peptide of prom-1, as that term is used herein.

In one embodiment, a method of promoting angiogenesis in a tissue in need thereof is provided, the method comprising contacting the tissue with a composition comprising an isolated peptide, variant, fusion protein, peptide mimetic or conjugate thereof. The method is applied in the context of wound healing, burns, tissue repair, bone repair, impaired fertility, myocardial infarction, cardiac hypertrophy, erectile dysfunction, promoting revascularization after disease or trauma, tissue grafts, or tissue engineered constructs. In addition, the methods described herein can be administered to potentiate the vasodilatory effect of VEGF in the context of disorders associated with reduced vasodilation such as e.g., erectile dysfunction and high blood pressure.

Accordingly, in one embodiment, one first diagnoses the individual as having a wound in need of healing, a tissue in need of repair, impaired fertility, cardiac hypertrophy, erectile dysfunction, tissue in need of revascularization, tissue in need of grafting or engineered constructs, and then contacts the tissue with a prom-1 peptide as described herein.

Another aspect described herein relates to an isolated prom-1 peptide derived from a prominin polypeptide, the peptide having regenerative, pro-angiogenic and/or VEGF-binding activity.

Also described herein is an isolated prom-1 peptide of a prominin polypeptide, the peptide having regenerative and/or pro-angiogenic activity, and stimulating endothelial cell proliferation.

Also described herein is an isolated prom-1 peptide derived from an extracellular domain of a prominin polypeptide, the peptide having regenerative and/or pro-angiogenic activity.

In one embodiment of this aspect and all other aspects described herein, the prominin-1 polypeptide is human prominin-1.

In another embodiment of this aspect and all other aspects described herein, the extracellular domain is selected from SEQ. ID. No. 1, 2, and 3.

In another embodiment of this aspect and all other aspects described herein, the peptide comprises at least 6 consecutive amino acid residues of prom-1, e.g., SEQ ID NO: 36, wherein the peptide does not include a full-length prominin polypeptide.

Another aspect described herein relates to an isolated peptide that is a conservative amino acid substitution variant of a peptide as described above.

In one embodiment, the peptide of any of the aspects described above is at least 90% identical to a prom-1 peptide, wherein the peptide binds VEGF and has regenerative and/or pro-angiogenic activity. In other embodiments, the peptide of any of the aspects described above is at least 80%, at least 70%, at least 60%, or at least 50% identical to a prom-1 peptide, wherein the peptide binds VEGF and has regenerative and/or pro-angiogenic activity.

Another aspect described herein relates to an isolated peptide fragment of a prominin polypeptide, the peptide having regenerative, pro-angiogenic activity and/or VEGF-binding activity, wherein the peptide consists or consists essentially of a peptide selected from the group consisting of: LCGNSF-SGGQPS (SEQ. ID. No. 4); PNIIPVLDEIKS (SEQ. ID. No. 5); LCGVCGYDRHAT (SEQ. ID. No. 6); ITNNTSSVIIEE (SEQ. ID. No. 7); DRVQRQTTTVVA (SEQ. ID. No. 8); and CSFAYDLEAKANSLPPGNLRN (SEQ. ID. No.9), or a conservative amino acid substitution variant thereof that substantially retains regenerative, pro-angiogenic activity and/or VEGF-binding activity.

In one embodiment, the isolated peptide of any one of the aspects described herein above enhances VEGF binding to endothelial cells. Thus, methods and uses of the peptide fragments for enhancing VEGF binding to endothelial cells are provided.

In another embodiment, the isolated peptide of any one of the aspects described herein enhances cell proliferation. Thus, methods and uses of the peptide fragments for enhancing cell proliferation are provided.

In another embodiment, the isolated peptide in any of the above-described aspects enhances proliferation of endothelial cells. Thus, methods and uses of the peptide fragments for enhancing endothelial cell proliferation are provided.

In another embodiment, the isolated peptide in any of the above-described aspects enhances angiogenesis in the presence of a pro-angiogenic factor. Thus, methods and uses of the peptide fragments for promoting angiogenesis are provided.

In another embodiment, the isolated peptide in any of the above-described aspects enhances cell migration in the presence of a pro-angiogenic factor. Thus, methods and uses of the peptide fragments for enhancing cell migration in the presence of a pro-angiogenic factor are provided.

In one embodiment, the isolated prom-1 peptide is a cyclic peptide.

In one embodiment, the cyclic peptide comprises a formula of CX(DRVQBQTTTVVA)ZC (SEQ ID NO: 51) or ACX (DRVQBQTTTVVA)ZC (SEQ ID NO: 52), wherein X or Z are each independently 0-20 amino acids, and wherein B is any one of the naturally occurring amino acid or a derivative thereof. In one embodiment, the glutamine (Q) at position 6 of the core (DRVQBQTTTVVA) (SEQ ID NO: 54) of the cyclic peptide is substituted with any known amino acid other than glutamine.

In one embodiment, B is a more hydrophobic amino acid residue than arginine which has a hydrophobic index of (−4.5) according to Kyte and Doolittle. In another embodiment, the glutamine (Q) at position 6 of the core (DRVQBQTTTVVA) (SEQ ID NO: 54) of the cyclic peptide is substituted with a more hydrophobic amino acid residue than glutamine which has a hydrophobic index of (−3.5) according to Kyte and Doolittle.

In one embodiment, the cyclic peptide is selected from the group consisting of:

```
ACGG(DRVQRQTTTVVA)GGC,          (SEQ ID NO: 15)

ACGG(DRVQRQTTTVVA)GGGGGGC,      (SEQ ID NO: 16)
and

CGGGGGG(DRVQRQTTTVVA)GGCA.      (SEQ ID NO: 17)
```

In another embodiment, the isolated peptide in any of the above-described aspects is conjugated to a polymer.

In another embodiment, a fusion protein comprising a peptide of any of the above-described aspects fused to a heterologous peptide or polypeptide is provided, wherein the fusion protein is not a full-length prominin polypeptide.

Another embodiment relates to a composition comprising a pharmaceutically acceptable carrier and a peptide or fusion protein of any one of the above-described aspects.

Also described herein are methods and uses for promoting cell proliferation in a tissue in need thereof, the methods comprising contacting the tissue with a composition as described above.

Another aspect described herein relates to a method or use for promoting angiogenesis in a tissue in need thereof, the method comprising contacting the tissue with a composition as described above.

In one embodiment of the above-noted aspects, the method is applied in the context of wound healing, burns, neuronal growth, protection or repair, tissue repair, bone repair, fertility promotion, myocardial infarction, cardiac hypertrophy, treatment of erectile dysfunction, modulation of blood pressure, revascularization after disease or trauma, tissue grafts, or tissue engineered constructs.

Also described herein is a method of promoting wound healing, the method comprising contacting a wound, or tissue surrounding the wound, with an isolated prom-1 peptide or fusion protein of any one of the above-described aspects, whereby wound healing is enhanced relative to wound healing in the absence of the peptide or fusion protein.

Another aspect described herein relates to a method of promoting neuroprotection, the method comprising contacting a neuronal cell with an isolated prom-1 peptide of a prominin polypeptide or fusion protein of any one of the above-described aspects, wherein the peptide binds VEGF, and wherein the contacting promotes neuroprotection of the neuronal cell.

In one embodiment of this aspect and all other aspects described herein, the prom-1 peptide derived from a prominin polypeptide comprises sequence found in an extracellular domain of the prominin polypeptide.

In another embodiment of this aspect and all other aspects described herein, the prominin polypeptide is human prominin-1.

In another embodiment of this aspect and all other aspects described herein, the extracellular domain is one of SEQ. ID. No. 1, 2, or 3.

In another embodiment of this aspect and all other aspects described herein, the prom-1 peptide comprises at least 6 consecutive amino acid residues SEQ ID NOs: 1, 2, or 3, and wherein the peptide does not include a full-length prominin polypeptide.

In another embodiment of this aspect and all other aspects described herein, the prom-1 peptide comprises a conservative amino acid substitution relative to the corresponding wild-type human prominin-1 polypeptide sequence.

In another embodiment of this aspect and all other aspects described herein, the prom-1 peptide is a conservative amino acid substitution variant of a peptide of SEQ ID NO: 8.

In another embodiment of this aspect and all other aspects described herein, the prom-1 peptide comprises or consists essentially of a cyclic peptide.

In another embodiment of this aspect and all other aspects described herein, the prom-1 peptide comprises or consists essentially of a heterologous fusion polypeptide.

In another embodiment of this aspect and all other aspects described herein, the prom-1 peptide is conjugated to a polymer. In one embodiment, the peptide is PEGylated.

In another embodiment of this aspect and all other aspects described herein, the prom-1 peptide consists essentially of a peptide of SEQ ID NO: 8.

In another embodiment of this aspect and all other aspects described herein, the prom-1 peptide consists of SEQ ID NO: 8.

In another embodiment of this aspect and all other aspects described herein, the contacting step comprises administering a composition comprising a prom-1 peptide and a pharmaceutically acceptable carrier to an individual in need thereof, e.g., for neuroprotection. In the embodiment of the method of neuroprotection, one first diagnoses an individual in need of neuroprotection or neuronal growth, and then contacts the tissue with a prom-1 peptide as described herein.

In another embodiment of this aspect and all other aspects described herein, the contacting step prevents or delays neuronal cell death relative to neuronal cell death occurring in the absence of the contacting.

Definitions

As used herein, the term "regenerative activity" refers to the capacity to stimulate or mediate the restoration of functional tissue following insult, disease or disorder that destroys or damages tissue. In one embodiment, "regenerative activity" refers to lessening, preventing and/or mitigating tissue degeneration resulting from a degenerative disease, e.g., amyotrophic lateral sclerosis (ALS), multiple sclerosis (MS), Alzheimer's disease, and Parkinson's disease. In one embodiment, "regenerative activity" comprises pro-angiogenic activity. In another embodiment, "regenerative activity" comprises neuroprotection and/or stimulation of neuronal growth activity. Assays for "regenerative activity" include but are not limited to angiogenesis assays, wound healing assay, bone repair assay, neuronal growth assay, and use of mouse models of various diseases (e.g., ALS, MS, Alzheimer's disease, and Parkinson's disease).

As used herein, in one embodiment, the term "pro-angiogenic activity" refers to the stimulation or enhancement of angiogenesis and/or endothelial cell proliferation.

As used herein, the term "prom-1 peptide" refers to a peptide derived from a prominin-1. Preferably, the prom-1 peptide is derived from human prominin-1 (Genbank Accession No.: NM_006017.1; NP_006008.1; AF027208.1; SEQ ID NO: 36). In one aspect of the invention, the prom-1 peptide is not a variant or derivative, but rather consists essentially of a peptide of prominin-1 that can potentiate one or more of the biological effects of an endogenous growth factor. The term "prom-1 peptide" encompasses peptides that have regenerative, pro-angiogenic, vasoregulator properties, and/or neurotrophic activity.

As used herein, the term "variant" refers to a peptide fragment from prom-1 that has one or more conservative amino acid substitutions from the sequences of SEQ. ID. NO.4-9. Conservative amino acid substitutions are well known to one skilled in the art. For example, the amino acid serine can be substituted for threonine and the amino acid aspartate may be substituted for glutamate. "Conservative amino acid substitution variant," "variant" and "prom-1 peptide variant" are used interchangeably herein.

In one aspect, the term "variant" refers to a VEGF-binding peptide fragment from prom-1 that has one or more conservative amino acid substitutions from the sequences of SEQ. ID. NO.4-9 but substantially retains one or more of the VEGF-binding, regenerative, pro-angiogenic, pro-cell proliferation, pro-cell migration, and/or neuroprotective activities of the original peptide as the specific case may be. By "substantially retain" means the activity of the variant is at least 50% compared to the activity of the original peptide in a similar assay, under similar conditions; preferably the activity is at least 60%, at least 70%, at least 80%, at least 90%, at least 95%, at least 99%, at least 100%, at least 2-fold, at least 5-fold, at least 10-fold, at least 100-fold or higher activity compared to the original peptide. The VEGF-binding, regenerative, pro-angiogenic, pro-cell proliferation, pro-cell migration, and/or neuroprotective activities of the variant peptide are determined by methods well known in the art and by the methods described herein. Conservative amino acid substitutions are well known to one skilled in the art. For example, the amino acid serine can be substituted for threonine and the amino acid aspartate may be substituted for glutamate.

As used herein, a "derivative" of a peptide is a form of a given peptide that is chemically modified relative to the reference peptide, the modification including, but not limited to, oligomerization or polymerization, modifications of amino acid residues or peptide backbone, cross-linking, cyclization, conjugation, fusion to additional heterologous amino acid sequences, or other modifications that substantially alter the stability, solubility, or other properties of the peptide while substantially retaining VEGF binding activity.

As used herein, the term "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Specific examples of conservative amino acid substitutions are described herein below.

As used herein, the term "peptide mimetic" or "peptidomimetic" refers to a peptide mimetic of a peptide fragment from prom-1 that biologically mimics the peptide's functions, such as VEGF-binding, regenerative, pro-angiogenic, pro-cell proliferation, pro-cell migration, and/or neuroprotective activities of a prominin-1 peptide as described herein. By "biologically mimics" is meant that a peptidomimetic derivative of a peptide as described herein has at least 50% of the regenerative, pro-angiogenic, pro-proliferative, pro-cell migration, pro-wound healing and/or neuroprotective activity of the peptide itself. In one embodiment, "biologically mimics" is meant that a peptidomimetic derivative of a peptide as described herein has at least 50% of the VEGF binding activity and/or at least 50% of the regenerative, pro-angiogenic, pro-proliferative, pro-cell migration, and/or neuroprotective activity of the peptide itself.

As used herein, the term "amino acid" of a peptide refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. In one embodiment, the amino acids in a peptide described herein are naturally occurring amino acids.

By "conjugated" is meant the covalent linkage of at least two molecules. As described herein, an isolated peptide of prom-1 is conjugated to a pharmaceutically acceptable polymer to increase its serum half-life.

The term "fragment" refers to any peptide or polypeptide having an amino acid residue sequence shorter than that of a full-length polypeptide whose amino acid residue sequence is described herein. An isolated peptide of prom-1 is shortened or truncated compared to its parent full-length prom-1. The polypeptide can have N-terminus or C-terminus truncations and/or also internal deletions. Examples of prom-1 fragments include fragments consisting of amino acids 13-50, 57-79, and 245-260.

As used herein, the term "homologous proteins" or "homologs" refers to proteins that look similar by way of amino acid sequences and can work in similar ways in different species of organism. For example, human, rabbit, rat, mouse, horse, cow, pig and chicken express transferrins and these transferrins from the various organisms all have the same function of transporting iron. The polypeptides of these transferrins are approximately of the same molecular size and structure, have the same number of domains (one N- and one C-terminal domain), again each domain of approximately the same size, and the same number, type and position of protein secondary folds such as beta-sheets and alpha helices. When the sequences are aligned, homologous proteins have exactly the same amino acid residues at certain amino acid positions in the polypeptide (i.e., highly conserved regions) and also similar amino acid residues at other amino acid positions in the polypeptide.

As used herein, "heterologous expression" refers to protein expression in an organism or tissue or cell type that is different from that of the transgene or coding nucleic acid being expressed into protein in nature. For example, the coding nucleic acid is derived from human, but the coding nucleic acid is used to express the coded protein is a non-human organism (e.g., yeast or hamster) or non-human cells.

As used herein, a "heterologous protein or peptide" refers to a protein or peptide that is not naturally expressed in an organism or cell. A "heterologous protein" can be expressed when the coding nucleic acid that codes for it is introduced into the organism that does not naturally express the "heterologous protein".

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

The term "isolated" means the protein is removed from its natural surroundings. However, some of the components found with it may continue to be with an "isolated" protein. Thus, an "isolated protein" is not as it appears in nature but may be substantially less than 100% pure protein.

The term "vector" as used herein, refers to a nucleic acid construct designed for delivery to a host cell or transfer between different host cells. As used herein, a vector can be viral or non-viral. In one embodiment, the vector permits the expression of a sequence encoded within the vector.

As used herein, a "retroviral vector" refers to an expression vector that comprises a nucleotide sequence that encodes a transgene and that further comprises nucleotide sequences necessary for packaging of the vector. Preferably, the retroviral transfer vector also comprises the necessary sequences for expressing the transgene in host cells.

As used herein, the term "pro-angiogenic factors" refers to factors that directly or indirectly promote new blood vessel formation (e.g., neovascularization).

As used herein, the term "enhances VEGF binding to endothelial cells" refers to an increase in VEGF binding to endothelial cells of at least 10% (as assessed by measuring binding of e.g., $^{125}$I-VEGF to endothelial cells as described herein in the Examples section) in the presence of both VEGF and a prom-1 peptide, compared to the amount of VEGF binding to endothelial cells when VEGF is administered alone. Preferably, the prom-1 peptide enhances VEGF binding to endothelial cells by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more compared to VEGF binding when VEGF is administered in the absence of a prom-1 peptide.

As used herein, the terms "increasing angiogenesis", "promoting angiogenesis" or "enhancing angiogenesis" refer to an increase in at least one measurable marker of angiogenesis by at least 10%, at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more, in the presence of a prom-1 peptide relative to that marker in the absence of such agent. The terms recited above also encompass co-treatment of a cell or subject with VEGF and a prom-1 peptide, wherein an increase as described above is determined by comparing the angiogenic marker to the effect of VEGF alone on the same marker. To date, six human VEGF mRNA species, encoding VEGF isoforms of 121, 145, 165, 183, 189 and 206 amino acids, are produced by alternative splicing of the VEGF mRNA.

The determination of VEGF binding to endothelial cells can be performed with any VEGF isoform that promotes angiogenesis, for example, at least isoform $VEGF_{165}$, $VEGF_{121}$, and $VEGF_{189}$. In one embodiment, radiolabelled $VEGF_{165}$ is used to determine VEGF binding to endothelial cells.

Endothelial cell migration can be assessed, for example, by measuring the migration of cells through a porous membrane using a commercially available kit such as BD BioCoat Angiogenesis System or through a Boyden chamber apparatus. Thus, as used herein, the term "enhances cell migration" refers, at a minimum, to an increase in the migration of endothelial cells through a porous membrane of at least 10% in the presence of a prom-1 peptide; preferably the increase is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of a prom-1 peptide, as that term is used herein.

Endothelial cell growth can be determined, for example, by measuring cell proliferation using an MTS assay commercially available from a variety of companies including RnD Systems, and Promega, among others. Thus, as used herein, the term "enhances cell proliferation" refers to an increase in the number of endothelial cells of at least 10% in the presence of a prom-1 peptide (as assessed using e.g., an MTS assay); preferably the increase is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of a prom-1 peptide, as that term is used herein.

The term "wound" as used herein refers broadly to injuries to an organ or tissue of an organism that typically involves division of tissue or rupture of a membrane (e.g., skin), due to external violence, a mechanical agency, or infectious disease. The term "wound" encompasses injuries including, but not limited to, lacerations, abrasions, avulsions, cuts, velocity wounds (e.g., gunshot wounds), penetration wounds, puncture wounds, contusions, hematomas, tearing wounds, bone fractures and/or crushing injuries. In one aspect, the term "wound" refers to an injury to the skin and subcutaneous tissue initiated in any one of a variety of ways (e.g., pressure sores from extended bed rest, wounds induced by trauma, cuts, ulcers, burns and the like) and with varying characteristics. Skin wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

As used herein, the term "wound healing" refers to a process by which the body of a wounded organism initiates repair of a tissue at the wound site (e.g., skin). In one embodiment, wound healing also includes the healing of burn wounds. The wound healing process requires, in part, angiogenesis and revascularization of the wounded tissue. Wound healing can be measured by assessing such parameters as contraction, area of the wound, percent closure, percent closure rate, and/or infiltration of blood vessels as known to those of skill in the art or as described herein in the section entitled "Wound healing assays".

As used herein, the term "treat" or treatment" refers to reducing or alleviating at least one adverse effect or symptom associated with medical conditions that are associated with excessive, unwanted, and/or aberrant angiogenesis, or diseases or disorders related to degeneration. In one embodiment, "treat" or treatment" refers to reducing or alleviating at least one adverse effect or symptom associated with medical conditions that are associated with wounds, burns, neuronal damage, neuron degeneration, cell degeneration, tissue damage, bone damage, infertility, cardiac hypertrophy, cardiomyopathy, erectile dysfunction and hypertension. In one embodiment, "treat" or treatment" refers to increased collateral artery growth, revascularization after disease or trauma and tissue grafts in tissues or subjects in need thereof.

As used herein, the term "promotes neuroprotection" refers to conditions under which neuronal cell death (necrotic, apoptotic or otherwise) is prevented or decreased, e.g., by at least 20%, and preferably at least 30%, at least 40%, at least 50%, at least 60%, at least 75%, at least 90%, at least 95% or more, up to and including, 100% protection in the presence of an agent such as a peptide disclosed herein, relative to the absence of that agent. In one aspect, the term refers to conditions under which neuronal cell growth, axonal elongation, neuronal proliferation or functional organization is increased by at least 20%, and preferably at least 30%, at least 40%, at least 50%, at least 60%, at least 75%, at least 90%, at least 95% or more, up to and including, for example, at least 1×, at least 2×, at least 3×, at least 5×, at least 10×, at least 20× or more in the presence of an agent, relative to the absence of such agent. Effects of neuroprotection can be assessed by any assay known in the art, e.g., neural cell death, neural outgrowth etc. known in the art and/or as described herein.

As used herein, the term "stimulates neuronal growth" refers to conditions under which neuronal cell growth (e.g., axonal growth, trophism) is increased e.g., by at least 20%, and preferably at least 30%, at least 40%, at least 50%, at least 60%, at least 75%, at least 90%, at least 95% or more, up to and including, for example, at least 1×, at least 2×, at least 3×, at least 5×, at least 10×, or at least 20× or more in the presence of an agent, such as a peptide composition set forth herein, relative to the absence of that agent.

As used herein, the term "contacting neurons" refers to any mode of peptide delivery or "administration" either to cells, or to whole organisms in which the peptide is capable of exhibiting its pharmacological effect in neurons. "Contacting neurons" is intended to include both in vivo and in vitro methods of bringing an agent as described herein into proximity with a neuron, particularly in a neuron in need of protection or stimulation, e.g., in neurodegenerative disease such has Parkinson's and ALS. Suitable modes of administration can be determined by those skilled in the art, and such modes of administration may vary between peptides. For example, when axonal growth of CNS neurons is stimulated ex vivo, peptides can be administered, for example, by transfection, lipofection, electroporation, viral vector infection, or by addition to growth medium. An in vivo means of contacting neurons with an agent that stimulate growth of neurons include, but is not limited to, for example, the assay that is described in Yin et al, 2003, J. Neurosci. 23:2284, which is incorporated by reference in its entirety.

As used herein, the term "pharmaceutical composition" refers to the active agent in combination with a pharmaceutically acceptable carrier of chemicals and compounds commonly used in the pharmaceutical industry. The term "pharmaceutically acceptable carrier" excludes tissue culture medium.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Unless otherwise explained, all technical and scientific terms used herein have the same meaning as commonly understood by one of ordinary skill in the art to which this disclosure belongs. Definitions of common terms in cell biology and molecular biology can be found in "The Merck Manual of Diagnosis and Therapy", 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology are also be found in Benjamin Lewin, Genes IX, published by Jones & Bartlett Publishing, 2007 (ISBN-13: 9780763740634); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

BRIEF DESCRIPTION OF THE DRAWINGS

FIG. 1 shows an exemplary protein sequence alignment of some homologous members of the prominin family. FIG. 1 discloses SEQ ID NOS 20-26, respectively, in order of appearance.

FIG. 2B discloses SEQ ID NOS 4-9, respectively, in order of appearance.

FIG. 3 shows that peptide #237 increased VEGF binding to endothelial cells and melanoma cells. 10000 cells were incubated in binding buffer containing 20 mM Hepes, 0.1% BSA and I125-VEGF (12 ng/ml) for 3 h on ice.

FIG. 9 discloses SEQ ID NOS 8, 8, 8, 8 and 27-35, respectively, in order of appearance.

FIG. 10B is a bar graph showing the results of the mouse ear punch model experiment.

FIG. 11B is a set of micrographs showing the results of such experiments.

DETAILED DESCRIPTION OF THE INVENTION

Figures 2A, 2B:
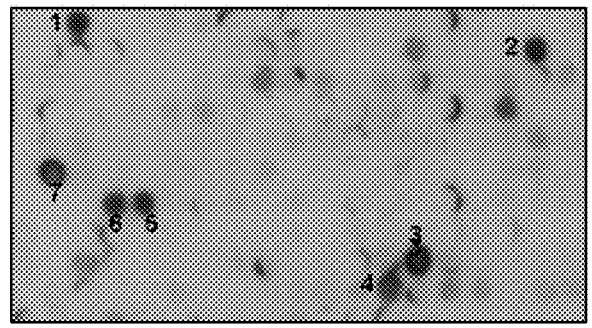
FIG. 2A shows prominin-1 fragments bind VEGF. Black dots that are above the background were chosen as candidates for VEGF binding peptides.
FIG. 2B shows peptide sequences derived from the extracellular domains of Prominin-1 that bind VEGF.

The methods and compositions described herein are based, in part, on the discoveries that short peptides derived from the extracellular portion of a penta span transmembrane glycoprotein have distinct effects on angiogenesis. The inventors found that short peptides of Prominin-1 (prom-1) bind VEGF (see table 1), an endogenous pro-angiogenesis factor that is important for normal growth and development but also during unwanted and aberrant vascularization such as in cancer and diabetic retinopathy. Some of the peptides promoted VEGF binding to other cell types, promoted proliferation of endothelial cells in vitro, and enhanced angiogenesis and cell migration in the presence of VEGF. These peptides with regenerative and/or pro-angiogenic properties are useful in promoting angiogenesis such as in wound healing and tissue repair.

The peptides described herein were identified based on their ability to bind VEGF, such as $VEGF_{165}$, $VEGF_{121}$, and $VEGF_{145}$. The peptides potentiate the activity of VEGF in processes including angiogenesis, cell migration, vasodilation, and cell proliferation. Given these effects on the various activities of VEGF, it is considered that the peptides described herein, and variants and derivatives that bind VEGF can influence other effect of VEGF, including, for example, neurotrophic and neuroprotective effect, cell migration, cell proliferation, and angiogenesis. In one embodiment, the peptides described herein are administered to potentiate the vasodilatory effect of VEGF for the treatment or regulation of high blood pressure and/or erectile dysfunction.

The human prominin-1 (aka AC133, CD133, MSTP061, PROML1, RP41, prominin 1, hProminin, prominin (mouse)-like 1, hematopoietic stem cell antigen; Genbank Accession No.: NM_006017.1; NP_006008.1; AF027208.1) is a penta span transmembrane glycoprotein (5-TMD) expressed in stem cells, primarily on the apical membrane of epithelial cells, and is a marker of hematopoietic stem cells. It belongs to a molecular family of 5-transmembrane domain (TMD) proteins, pfam prominin. This "family" includes members from several different species including human, mouse, rat, fly, zebrafish and nematode worms. The 5-TMD structure includes an extracellular N-terminus, two short intracellular loops, two large extracellular loops and an intracellular C-terminus. Prom-1 was initially shown to be expressed on primitive hematopoietic stem and progenitor cells and on retinoblastoma cells. However, prom-1 has since been shown to be expressed on hemangioblasts, and neural stem cells as well as on developing epithelia. The prom-1 positive fractions of human bone marrow, cord blood and peripheral blood efficiently engraft in xenotransplantation models, and contain the majority of the granulocyte/macrophage precursors, NOD/SCID repopulating cells and CD34+ dendritic cell precursors. Phenotypically, prom-1 positive cells in blood and marrow are CD34 bright, with CD34 dim CD71 bright cells being negative for prom-1 expression. Prom-1 is also found in extracellular membrane particles in body fluids. No natural ligand has yet been demonstrated for prom-1, and its specific function in hematopoietic tissue is unknown (Corbeil, D., et. al, Blood. 1998, 91:2625-6; Miraglia S, et. al., Blood. 1997, 90:5013-21; Weigmann A, et. al, Proc Natl. Acad. Sci. USA. 1997, 94:12425-30). The exact function of prominin is unknown although in humans, defects in PROM1, the gene coding for prominin, cause retinal degeneration.

Prom-1 expression is also associated with cancer; many leukemias express prom-1 as well as CD34. It is believed that colon cancer is initiated and propagated by a small number of undifferentiated tumorigenic prom-1+ cells. Prom-1 mRNA expression is increased in cancer patients with metastatic disease, specifically with bone metastasis. In addition, prom-1 mRNA expression seems to be an independent prognostic factor for overall survival.

One of the reasons why prom-1 can promote cancer and/or metastasis is that the intact full length prom-1 enhances the angiogenesis properties of VEGF and therefore is pro-angiogenic. This characteristic of prom-1 could certainly support the pathological angiogenesis associated with cancer and metastasis. Treatment options that specifically target the prom-1 protein and its expression are currently under study and include blocking activity with anti-prom-1 antibody and inhibiting expression by siRNA.

Provided herein are peptides derived from a prominin polypeptide that has regenerative and/or pro-angiogenic activities.

Accordingly, embodiments of the present invention provide isolated peptide fragments derived from prominin-1 (prom-1), the peptides having regenerative, pro-angiogenic activity and/or VEGF-binding activity as measured by an in vitro ELISA-based VEGF-binding assay. The pro-angiogenic activities include: promoting VEGF binding to other cell types, the other cell types including, for example, endothelial cells; promoting cell proliferation of endothelial cells in vitro; enhancing angiogenesis in the presence of VEGF as assayed via a corneal micro pocket assay; enhancing endothelial cell migration in vivo in the presence of VEGF; and promoting neovascularization in vivo in the presence of growth factors as assayed in an ear wound healing assay as described herein.

Figure 1:
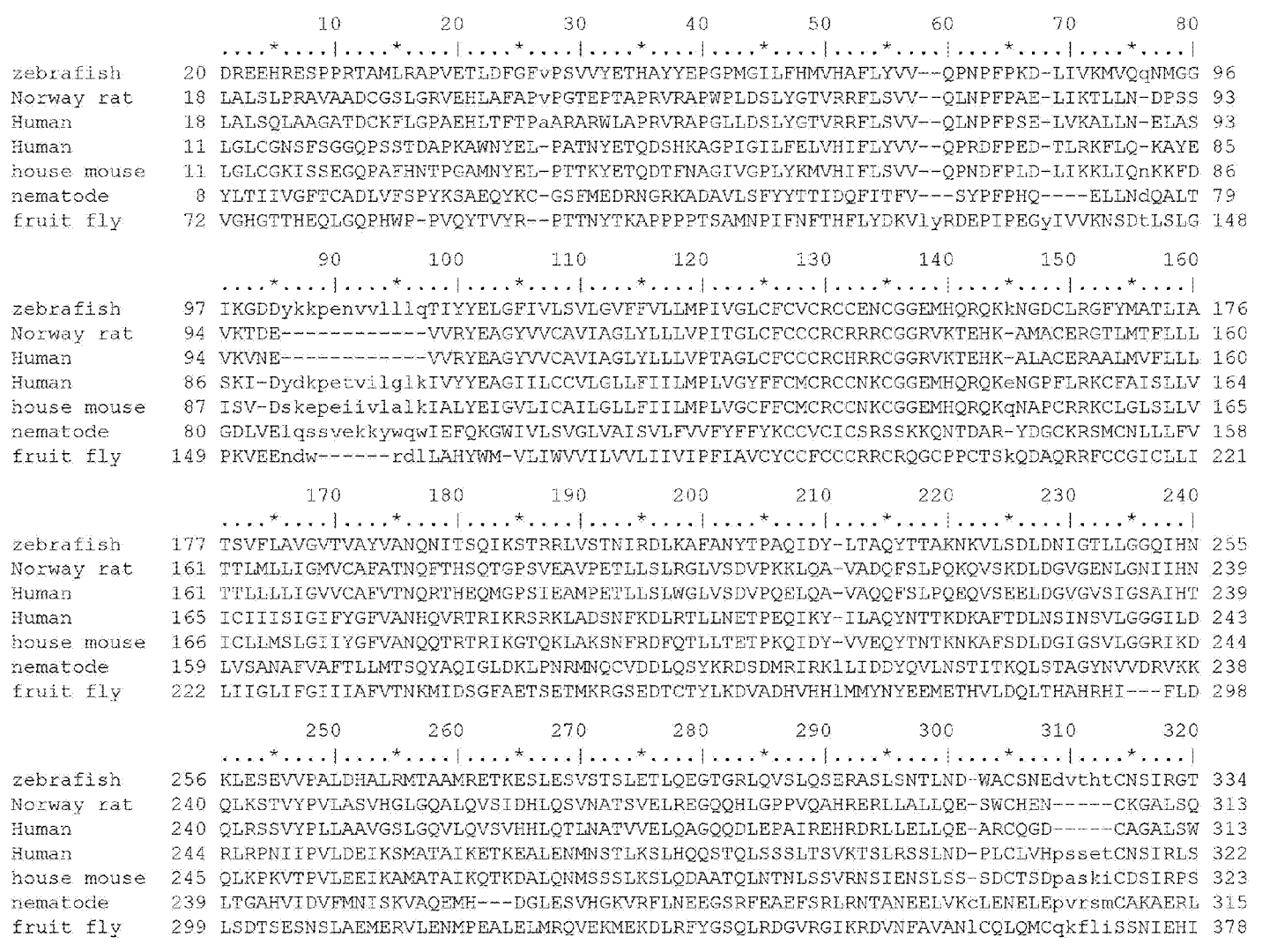

In one embodiment, an isolated peptide with regenerative and/or pro-angiogenic activity is derived from the full length human prom-1 (Genbank Accession No.: NM_006017.1; NP_006008.1; AF027208.1). However, under no circumstances does the term "prom-1 peptide" encompass the full length peptide. Rather, "prom-1 peptide" refers to a truncated peptide of prom-1. In other embodiments, an isolated peptide with regenerative and/or pro-angiogenic activity is from homologous protein members of the prominin protein family (pfam05478:Prominin). Homologous protein members of the prominin protein family include known and identified proteins as well as predicted proteins from genomic studies. All members of the prominin family are predicted to contain five membrane spanning domains, with an N-terminal domain exposed to the extracellular space followed by four, alternating small cytoplasmic and large extracellular loops and a cytoplasmic C-terminal domain. These proteins are homologs of the human prom-1. An example of the protein sequence alignment of some of the prominin family members is shown in FIG. 1. Examples of prom-1 homologs are: *Danio rerio* (zebrafish) prominin-like 2 protein, swissprot Q90WI3, Genbank Accession No. GI:82177379; *Rattus norvegicus* (Norway rat) testosterone-regulated prominin-related protein, swissprot Q8R4B6, Genbank Accession No. GI:81866961; *Homo sapiens* (human) Prominin-like protein 2, swissprot Q8N271, Genbank Accession No. GI:74728673; *Mus musculus* (house mouse) Prominin-like protein 1, swissprot O54990, Genbank Accession No. GI:13124464; *Caenorhabditis elegans* hypothetical protein F08B12.1, swissprot Q19188, Genbank Accession No. GI:74963586; and *Drosophila melanogaster* (fruit fly) Prominin-like protein, swissprot P82295, Genbank Accession No. GI:13124468.

In one embodiment, the isolated peptide with regenerative and/or pro-angiogenic activity comprises at least 6 consecutive amino acid residues. The 6 amino acid residues are consecutive, reflecting what is encoded and expressed in the intact full length prom-1 polypeptide. In another embodiment, the isolated peptide with regenerative and/or pro-angiogenic activity comprises no more than 50 amino acids of prom-1. In yet another embodiment, the isolated peptide with pro-angiogenic activity has at least 7, 8, 9, 10, 11, 12, 13, 14, 15, 16, 17, 18, 19, 20, 21, 22, 23, 24, 25, 26, 27, 28, 29, or 30 consecutive amino acid residues of prom-1. In another embodiment, the isolated peptide has no more than 30 consecutive amino acid residues. In yet another embodiment, the isolated peptide has no more than 29, 28, 27, 26, 25, 24, 23, 22, 21, 20, 19, 18, 17, 16, 15, 14, 13, 12, 11, 10, 9, 8, or 7 consecutive amino acid residues of prom-1. In another embodiment, the peptide has 50 or fewer consecutive amino acids and includes peptides with 49, 48, 47, 46, 45, 44, 43, 42, 41, 40, 39, 38, 37, 36, 35, 34, 33, 32, 31, and 30 consecutive amino acids of prom-1.

In one aspect, the isolated peptide with regenerative and/or pro-angiogenic activity consists essentially of or consists of a peptide selected from the group consisting of: LCGNSFSGGQPS (SEQ. ID. No. 4); PNIIPVLDEIKS (SEQ. ID. No. 5); LCGVCGYDRHAT (SEQ. ID. No. 6); ITNNTSSVIIEE (SEQ. ID. No. 7); DRVQRQTTTVVA (SEQ. ID. No. 8); and CSFAYDLEAKANSLPPGNLRN (SEQ. ID. No. 9) or a conservative substitution variant thereof.

Encompassed herein is an isolated peptide that is a VEGF-binding conservative substitution variant of a peptide with regenerative and/or pro-angiogenic activity as measured by an in vitro ELISA-based VEGF-binding assay as described herein. Conservative amino acid residue substitution is well known in the art. Conservative amino acid substitutions replace an amino acid with another amino acid of similar chemical structure. Examples of such substitution are glycine for alanine, leucine for valine, serine for threonine, and aspartate for glutamate. For example, SEQ ID NO: 4 can be altered to a peptide VCGNSFSGGQPS (SEQ ID NO: 55), LCANSFSGGQPS (SEQ ID NO: 56), or LCGNSFSAGQPS (SEQ ID NO: 57), or LCGNSFSGAQPS (SEQ ID NO: 58) where the residues that are in bold and italicized are changed. In one embodiment, only one of the amino acids is substituted with a conservative substitution. In another embodiment, two substitutions can be made. In other embodiments, up to four amino acids are substituted. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Conservative amino acid substitutions do not change the overall structure of the peptide nor the type of amino acid side chains available for forming van der Waals bonds with a binding partner. Conservative amino acid substitution can be achieved during chemical synthesis of the peptide by adding the desired substitute amino acid at the appropriate sequence in the synthesis process. Alternatively, molecular biology methods can be used. The coding sequence of a peptide described herein can be made by annealing two single strand nucleic acids that are complementary to each other. The sequence of the nucleic acid codes for the peptide. For example, a sense nucleic acid for the prom-1 peptide LCGNSFSGGQPS (SEQ. ID. No. 4) is 5' CTGTGCGGCAACAGCTTTAGCGGCGGC-CAGCCGAGC 3'(SEQ. ID. No.10) and the complementary anti-sense nucleic acid is 5' GCTCGGCTGGCCGC-CGCTAAAGCTGTTGCCGCACAG 3'(SEQ. ID. No. 11). After deciding on a substitute amino acid, the triplet codon for that substitute amino acid is determined and incorporated into the design of two complementary single strand nucleic acid sequences, with the codon of the substitute amino acid replacing the codon of amino acid that is being substituted. For example, for a serine to threonine substitution of the serine in position 5' of LCGNSFSGGQPS (SEQ. ID. No. 4), the triplet codon AGC for serine is replaced with the triplet codon ACG for threonine in the SEQ. ID. No. 10. Complementary changes in the design of the anti-sense SEQ. ID. No.11 are then made in order to anneal the two strands. Alternatively, site-directed mutagenesis, a known art, can be used for conservative amino acid substitution in the peptides described herein.

In some embodiments, conservative amino acid substitution are not to be found in the amino acid residues that are important for its regenerative, pro-angiogenic activity, pro-cell proliferation, and/or cell migration activity. In one embodiment, when a conservative amino acid substitution occurring at position X in a peptide results in reduced regenerative, pro-angiogenic activity, pro-cell proliferation, and/or cell migration activity, it is an indication that the amino acid residue at position X is important for its regenerative, pro-angiogenic activity, pro-cell proliferation, and/or cell migration activity. For example, in DRVQRQTTTVVA (SEQ. ID. NO:8), substitution of the valine at position 10 this amino acid with the conservative amino acid alanine destroyed activity and should not be substituted (See Example 13, FIG. 15).

In one embodiment, the isolated peptide and VEGF-binding conservative amino acid substitution variant thereof with regenerative and/or pro-angiogenic activity described herein enhances VEGF binding to endothelial cells. In another embodiment, the peptide with regenerative and/or pro-angiogenic activity described herein enhances cell proliferation in endothelial cells. In another embodiment, the peptide with regenerative and/or pro-angiogenic activity described herein enhances angiogenesis in the presence of pro-angiogenic factors. In some aspects, the peptide with regenerative and/or pro-angiogenic activity described herein enhances cell migration, such as endothelial cells, in the presence of pro-angiogenic factors. In another aspect, the peptide with regenerative and/or pro-angiogenic activity described herein promotes neovascularization in vivo in the presence of growth factors. Such growth factors include, but are not limited to, VEGF, EGF, bFGF, NGF, PDGF, IGF-1, and TGF-β.

In one embodiment, the isolated prom-1 peptide is a cyclic peptide.

In one embodiment, the cyclic peptide comprises a formula of CX(DRVQBQTTTVVA)ZC (SEQ ID NO: 51) or ACX (DRVQBQTTTVVA)ZC (SEQ ID NO: 52), wherein X or Z are each independently 0-20 amino acids, and wherein B is any one of the naturally occurring amino acid or a derivative thereof. In one embodiment, the glutamine (Q) at position 6 of the core (DRVQBQTTTVVA) (SEQ ID NO: 54) of the cyclic peptide is substituted with any one of the known 20 amino acids other that glutamine.

In one embodiment, B is a more hydrophobic amino acid residue than arginine which has a hydrophobic index of (−4.5) according to Kyte and Doolittle. In another embodiment, the glutamine (Q) at position 6 of the core (DRVQBQTTTVVA) (SEQ ID NO: 54) of the cyclic peptide is substituted with a more hydrophobic amino acid residue than glutamine which has a hydrophobic index of (−3.5)according to Kyte and Doolittle.

In one embodiment, the cyclic peptide is selected from the group consisting of:

```
ACGG(DRVQRQTTTVVA)GGC,         (SEQ ID NO: 15)

ACGG(DRVQRQTTTVVA)GGGGGGC,     (SEQ ID NO: 16)
and

CGGGGGG(DRVQRQTTTVVA)GGCA.     (SEQ ID NO: 17)
```

In one embodiment, a fusion polypeptide comprising a prom-1 peptide or a conservative amino acid substitution variant thereof is contemplated herein. The fusion polypeptide is formed by the fusion of a peptide described herein with another heterologous protein or a portion thereof. The heterologous protein is any protein that is not a member of the prominin family. The fusion gives rise to a prom-1 chimeric polypeptide. Such fusion prom-1 peptides can serve to enhance the serum half life of the prom-1 peptide in vivo. Examples include fusion with albumin, transferrin, transthyretin, and Fc of IgG (See G. M. Subramanian, 2007, Nature Biotechnology 25, 1411-141). Other fusions can facilitate protein expression, solubility during expression, and purification, e.g., thioredoxin, glutathione S-transferase, avidin and six histidine tags (SEQ ID NO: 19). In another embodiment, a peptide or a conservative amino acid substitution variant thereof described herein with regenerative and/or pro-angiogenic activity can be fused with other pro-angiogenic factors, e.g., VEGF, FGF and IGF to enhance angiogenic potency.

Peptide Modifications

It is to be understood that modified versions of the peptides described herein are encompassed in the present invention. Conservative substitutions are discussed herein above. Non-conservative substitutions are encompassed to the extent that that they substantially retain the activities of those peptides. Modification to a prom-1 peptide can be performed as described in U.S. published patent application Nos. 20080090760 and 20060286636, each of which is incorporated herein by reference in its entirety. The following provides a non-limiting discussion of various other peptide modifications encompassed within the scope of the invention.

Encompassed by the peptide described herein are chemical derivatives of a prom-1 peptide whose amino acid residue sequence is described herein, so long as they substantially retain the activities of those peptides. A "chemical derivative" is a subset of peptide derivatives as described herein and refers to a subject polypeptide having one or more residues chemically derivatized by reaction of a functional side group. In addition to side group derivatizations, a chemical derivative can have one or more backbone modifications including alpha-amino substitutions such as N-methyl, N-ethyl, N-propyl and the like, and alpha-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. Also included as chemical derivatives are those peptides which contain one or more non-limiting, non-natural amino acids, examples include those available for peptide synthesis from commercial suppliers (e.g., Bachem Catalog, 2004 pp. 1-276). For examples: 4-hydroxyproline may be substituted for proline; 5-hydroxylysine may be substituted for lysine; 3-methylhistidine may be substituted for histidine; homoserine may be substituted for serine; ornithine may be substituted for lysine; β-alanine may be substituted for alanine; norleucine may be substituted for leucine; phenylglycine may be substituted for phenylalanine, and L-1,2,3,4-tetrahydronorharman-3-carboxylic acid or H-β-(3-Benzothienyl)-Ala-OH may be substituted for tryptophan.

In certain embodiments, chemical modifications to the peptide include, but are not limited to the inclusion of, alkyl, alkoxy, hydroxyalkyl, alkoxyalkyl, alkoxycarbonyl, alkenyl, alkynyl, cycloalkyl, amino, alkylamino, aminoalkyl, dialkylamino, aminodialkyl, halogen, heteroatom, carbocycle, carbocyclyl, carbocyclo, carbocyclic, aryl, aralkyl, aralkoxy, aryloxyalkyl, heterocycle, heterocyclyl, heterocyclic, heteroaryl, and/or aliphatic groups.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic $C_3$-$C_{12}$ hydrocarbons which are completely saturated or which contain one or more units of unsaturation, but which are not aromatic. Lower alkyl refers to an alkyl group containing 1-6 carbons.

The term "amino" refers to an $NH_2$ group.

The term "alkylamino" or "aminoalkyl" refers to an amino group wherein one of the hydrogen atoms is replaced by an alkyl group.

The term "dialkylamino" or "aminodialkyl" refers to an amino group wherein the hydrogen atoms are replaced by alkyl groups, wherein the alkyl group may be the same or different.

The term "halogen" means F, Cl, Br, or I.

The term "heteroatom" means nitrogen, oxygen, or sulfur with a carbon ring structure and includes any oxidized form of nitrogen and sulfur, and the quaternized form of any basic nitrogen. Also the term "nitrogen" includes substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having six to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetrahydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on any unsaturated carbon atom of an aryl, heteroaryl, aralkyl, or heteroaralkyl group include a halogen, —R0, —OR0, —SR0, 1,2-methylene-dioxy, 1,2-ethylenedioxy, protected OH (such as acyloxy), phenyl (Ph), substituted Ph, —O(Ph), substituted —O(Ph), —CH2(Ph), substituted —CH2(Ph), CH2CH2(Ph), substituted —CH2CH2(Ph), —NO2, —CN, —N(R0)2, —NR0C(O)R0, NR0C(O)N(R0)2, NR0CO2R0, —NR0NR0C(O)R0, —NR0NR0C(O)N(R0)2, —NR0NR0C2R0, C(O)C(O)R0, C(O)CH2C(O)R0, —CO2R0, —C(O)R0, —C(O)N(R0)2, —OC(O)N(R0)2, S(O)2R0, —SO2N(R0)2, —S(O)R0, —NR0SO2N(R0)2, —NR0SO2R0, —C(=S)N(R0)2, C(=NH)N(R0)2, (CH2)yNHC(O)R0, and —(CH2)yNHC(O)CH(V—R0)(R0); wherein each R0 is independently selected from hydrogen, a substituted or unsubstituted aliphatic group, an unsubstituted heteroaryl or heterocyclic ring, phenyl (Ph), substituted Ph, O(Ph), substituted —O(Ph), —CH2 (Ph), or substituted —CH2(Ph); y is 0-6; and V is a linker group. Examples of substituents on the aliphatic group or the phenyl ring of R0 include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

An aliphatic group or a non-aromatic heterocyclic ring or a fused aryl or heteroaryl ring may contain one or more substituents. Examples of suitable substituents on any saturated carbon of an aliphatic group or of a non-aromatic heterocyclic ring or a fused aryl or heteroaryl ring include those listed above for the unsaturated carbon of an aryl or heteroaryl group and the following: =O, =S, =NNHR*, =NN(R*)$_2$, =N—, =NNHC(O)R*, =NNHCO2(alkyl), =NNHSO2 (alkyl), or =NR*, where each R* is independently selected from hydrogen, an unsubstituted aliphatic group, or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

Suitable substituents on the nitrogen of a non-aromatic heterocyclic ring include R+, —N(R+)2, —C(O)R+, —CO2R+, —C(O)C(O)R+, —C(O)CH2C(O)R+, —SO2R+, —SO2N(R+)2, C(=S)N(R+)2, —C(=NH)—N (R+)2, and —NR+SO2R+; wherein each R+ is independently selected from hydrogen, an aliphatic group, a substituted aliphatic group, phenyl (Ph), substituted Ph, —O(Ph), substituted —O(Ph), —CH2(Ph), substituted —CH2(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

In certain embodiments, the peptide monomers described herein are dimerized or multimerized by covalent attachment to at least one linker moiety. The linker moiety is preferably, although not necessarily, a $C_{1-12}$ linking moiety optionally terminated with one or two —NH—linkages and optionally substituted at one or more available carbon atoms with a lower alkyl substituent. Preferably the linker comprises —NH—R—NH— wherein R is a lower ($C_{1-6}$) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue. In certain other embodiments, the linker bridges the C-termini of two peptide monomers, by simultaneous attachment to the C-terminal amino acid of each monomer. In other embodiments, the linker bridges the peptides by attaching to the side chains of amino acids not at the C-termini. When the linker attaches to a side chain of an amino acid not at the C-termini of the peptides, the side chain preferably contains an amine, such as those found in lysine, and the linker contains two or more carboxy groups capable of forming an amide bond with the peptides.

The peptide monomers of the invention may be oligomerized using the biotin/streptavidin system. Oligomerizat6ion can enhance one or more activities of peptides as described herein. Biotinylated analogs of peptide monomers may be synthesized by standard techniques known to those skilled in the art. For example, the peptide monomers may be C-terminally biotinylated. These biotinylated monomers are then oligomerized by incubation with streptavidin (e.g., at a 4:1 molar ratio at room temperature in phosphate buffered saline (PBS) or HEPES-buffered RPMI medium (Invitrogen) for 1 hour). In a variation of this process, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

In some aspects, the peptides described herein can be linked physically in tandem to form a polymer of prom-1 peptides. The peptides making up such a polymer can be spaced apart from each other by a peptide linker. A "peptide linker" is a short (e.g., about 1-40, e.g., 1-20 amino acids) sequence of amino acids that is not part of the prom-1 or variant sequence. A linker peptide is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers (e.g., a (Gly$_4$Ser)n repeat where n=1-8 (SEQ ID NO: 18), preferably, n=3, 4, 5, or 6). The prom-1 peptides described herein can also be joined by chemical bond linkages, such as linkages by disulfide bonds or by chemical bridges. Molecular biology techniques that are well known to those skilled in the art can be used to create a polymer of prom-1 peptides. In one embodiment, combination of a prom-1 peptide and variant peptide is found in the polymer. Peptide sequences of the present invention can also be linked together using non-peptide cross-linkers (Pierce 2003-2004 Applications Handbook and Catalog, Chapter 6) or other scaffolds such as HPMA, polydextran, polysaccharides, ethylene-glycol, poly-ethylene-glycol, glycerol, sugars, and sugar alcohols (e.g., sorbitol, mannitol).

In an optional embodiment, polyethylene glycol (PEG) may serve as a linker that dimerizes two peptide monomers: for example, a single PEG moiety containing two reactive functional groups may be simultaneously attached to the N-termini of both peptide chains of a peptide dimer. These peptides are referred to herein as "PEGylated peptides."

In yet another embodiment, a linker moiety may comprise a molecule containing two carboxylic acids and optionally substituted at one or more available atoms with an additional functional group such as an amine capable of being bound to one or more PEG molecules. Such a molecule can be depicted as:—CO—(CH$_2$)n-uX—(CH$_2$)m-CO— where n is an integer between zero and 10, m is an integer between one and 10, X is selected from O, S, N(CH$_2$)pNR1, NCO(CH$_2$)pNR1, and CHNR1, R1 is selected from H, Boc (tert-butyloxycarbonyl), Cbz, and p is an integer between 1 and 10. In certain embodiments, one amino group of each of the peptides forms an amide bond with the linker. In certain other embodiments, the amino group of the peptide bound to the linker is the epsilon amine of a lysine residue or the alpha amine of the N-terminal residue, or an amino group of an optional spacer molecule. In one embodiment, a linker is used to cyclize peptides. In another embodiment, a spacer can be used in addition to a linker molecule for separating moieties as desired. In particularly preferred embodiments, both n and m are one, X is NCO(CH$_2$)pNR1, p is two, and R1 is Boc. Optionally, the Boc group can be removed to liberate a reactive amine group capable of forming a covalent bond with a suitably activated PEG species such as mPEG-SPA-NHS or mPEG-NPC (Nektar Therapeutics, San Carlos Calif.). Optionally, the linker contains more than one reactive amine capable of being derivatized with a suitably activated PEG species. Optionally, the linker contains one or more reactive amines capable of being derivatized with a suitably activated pharmacokinetic (PK) modifying agent such as a fatty acid, a homing peptide, a transport agent, a cell-penetrating agent, an organ-targeting agent, or a chelating agent.

A peptide monomer, dimer, multimer or oligomer as described herein may further comprise one or more linker and/or spacer moieties. In one embodiment, the linker moiety is a $C_{1-12}$ linking moiety optionally terminated with —NH— linkages or carboxyl (—COOH) groups, and optionally substituted at one or more available carbon atoms with a lower alkyl substituent. In one embodiment, the linker is R—COOH wherein R is a lower (C1-6) alkyl optionally substituted with a functional group such as a carboxyl group or an amino group that enables binding to another molecular moiety. For example, the linker may be a glycine (G) residue, or an amino hexanoic acid (Ahx) such as 6-amino hexanoic acid. In other embodiments, the linker is —NH—R—NH— wherein R is a lower (C1-6) alkyl substituted with a functional group such as a carboxyl group or an amino group that enables binding to another molecular moiety. For example, the linker may be a lysine (K) residue or a lysine amide (K—NH$_2$, a lysine residue wherein the carboxyl group has been converted to an amide moiety —CONH$_2$).

In some embodiments, the linker moiety has the following structure: —NH—(CH$_2$)$_\alpha$—[O—(CH$_2$)$_\beta$]$_\gamma$—O$_\delta$—(CH$_2$)$_\epsilon$—Y— where $\alpha$, $\beta$, $\gamma$, $\delta$, and $\epsilon$ are each integers whose values are independently selected. In some embodiments, $\alpha$, $\beta$, and c are each integers whose values are independently selected between one and about six, $\delta$ is zero or one, $\gamma$ is an integer selected between zero and about ten, except that when $\gamma$ is greater than one, $\beta$ is two, and Y is selected from NH or CO. In some embodiments, $\alpha$, $\beta$, and c are each equal to two, both $\gamma$ and $\delta$ are equal to 1, and Y is NH. In another embodiment, $\gamma$ and $\delta$ are zero, $\alpha$ and $\epsilon$ together equal five, and Y is CO.

The peptide monomers, dimers, or multimers of the invention may further comprise one or more water soluble polymer moieties. Preferably, these polymers are covalently attached to the peptide compounds of the invention. Preferably, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone)polyethylene glycol, propropylene glycol homopolymers, polypropylene oxide/ethylene oxide copolymers, and polyoxyethylated polyols. A preferred water soluble polymer is PEG.

The polymer may be of any molecular weight, and may be branched or unbranched. A preferred PEG for use in the present invention is linear, unbranched PEG having a molecular weight of from about 5 kilodaltons (kDa) to about 60 kDa (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 20 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the invention. The multiple attached polymers may be the same or different chemical moieties (e.g., PEGs of different molecular weight).

In certain embodiments, PEG may be attached to at least one terminus (N-terminus or C-terminus) of a peptide monomer or dimer. In other embodiments, PEG may be attached to a linker moiety of a peptide monomer or dimer. In a preferred embodiment, PEG is attached to the linker moiety of a peptide dimer. Optionally, the linker contains more than one reactive amine capable of being derivatized with a suitably activated PEG species.

Methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety.

Encompassed herein are conjugates of a peptide described herein or of a conservative amino acid substitution variant or derivative thereof. These peptides can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and $\alpha,\beta$-Poly[(2-hydroxyethyl)-DL-aspartamide, and the like, or mixtures thereof. Conjugation to a polymer can improve serum half-life, among other effects. A variety of chelating agents can be use to conjugate the peptides described herein. These chelating agents include but are not limited to ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et al., 2001, J. Biol. Chem., 276:27930-27935; and U.S. Pat. Nos. 5,601,825, 5,180,816, 6,423,685, 6,706,252, 6,884,780, and 7,022,673, which are hereby incorporated by reference in their entirety.

In one embodiment, the peptides, fusion proteins or conjugates of prom-1 peptides include modifications within the sequence, such as, modification by terminal-$NH_2$ acylation, e.g., acetylation, or thioglycolic acid amidation, by terminal-carboxylamidation, e.g., with ammonia, methylamine, and the like terminal modifications.

One can also modify the amino and/or carboxy termini of the peptides described herein. Terminal modifications are useful, to reduce susceptibility by proteinase digestion, and therefore can serve to prolong half life of the polypeptides in solution, particularly in biological fluids where proteases may be present. Amino terminus modifications include methylation (e.g., —$NHCH_3$ or —$N(CH_3)_2$), acetylation (e.g., with acetic acid or a halogenated derivative thereof such as $\alpha$-chloroacetic acid, $\alpha$-bromoacetic acid, or $\alpha$-iodoacetic acid), adding a benzyloxycarbonyl (Cbz) group, or blocking the amino terminus with any blocking group containing a carboxylate functionality defined by RCOO— or sulfonyl functionality defined by R—$SO_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; Muralidharan and Muir, 2006, Nat Methods, 3:429-38; and Lockless and Muir, 2009, Proc Natl Acad Sci USA. June 18, Epub. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower ($C_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods [e.g., as described in Hruby, et al. (1990) Biochem J. 268:249-262].

The peptide compounds described herein also serve as structural models for non-peptidic compounds with similar biological activity. Those of skill in the art recognize that a variety of techniques are available for constructing compounds with the same or similar desired biological activity as the prom-1 peptides, but with more favorable activity than the prom-1 peptide with respect to solubility, stability, and susceptibility to hydrolysis and proteolysis [See, Morgan and Gainor (1989) Ann. Rep. Med. Chem. 24:243-252]. These techniques include, but are not limited to, replacing the peptide backbone with a backbone composed of phosphonates, amidates, carbamates, sulfonamides, secondary amines, and N-methylamino acids. Further encompassed is a peptide mimetic of the peptide fragments of prom-1 described herein, including e.g., peptidomimetics of SEQ. ID. Nos. 4-9. Such a peptidomimetic may have different amino acids from the peptide that it mimics but substantially retains the VEGF-binding, regenerative, pro-angiogenic, pro-cell proliferation, pro-cell migration, anti-angiogenic, anti-cell proliferation, pro-cell migration, pro-wound healing, or neuroprotective activity of the peptide that it mimics.

Prom-1 Peptides in the Treatment of Disease

In one embodiment, provided herein is a composition comprising a pharmaceutically acceptable carrier and a peptide fragment of a prom-1 extracellular domain. In yet another embodiment, provided herein is a composition comprising a pharmaceutically acceptable carrier and a fusion protein comprising a peptide described herein or a conjugate of a peptide described herein. Also encompassed are compositions comprising a vector carrying the coding nucleic acid for a fusion protein comprising a peptide described herein or a polymer of peptides described herein.

In one embodiment, described herein is a method of promoting cell proliferation in a tissue in need thereof, the method comprising contacting the tissue with a composition comprising a peptide fragment of a prom-1 extracellular domain having a conservative amino acid substitution variant thereof, or a conjugate or other derivative thereof.

In one embodiment, described herein is a method of promoting angiogenesis in a tissue in need thereof, the method comprising contacting the tissue with a composition comprising a peptide of a prom-1 extracellular domain or a variant or derivative thereof.

In one embodiment, the method of promoting angiogenesis in a tissue in need thereof includes but is not limited to tissues that require re-vascularization after disease and trauma. Re-vascularization is needed for the rehabilitation of important organs, such as the heart, liver, bone, and lungs, after damage caused by disease and physical trauma (e.g., myocardial infarction, occlusive peripheral vascular disease). Diseases that halt, block or reduce blood circulation include, but are not limited to, stroke, heart attack, myocardial ischemia, ischemic limbs, diabetes, vascular diseases such as peripheral vascular disease (PVD), carotid artery disease, atherosclerosis, and renal artery disease. Trauma such as those from car accidents and shock can result in reduced blood circulation to areas needing increased circulation during the healing process. In addition, treatment of a subject with a peptide described herein is applicable to improving collateral coronary, peripheral artery, and carotid circulation in patients suffering from impaired wound healing, burn healing, bone fractures, neuropathy, impotence, erectile dysfunction, diabetic neuropathy, spinal cord injury, nerve injury, and other vascular occlusive disorders such as sickle cell disease, and stroke. As some of the prom-1 peptides can potentiate the effect of VEGF on the vasculature, the peptides are also contemplated herein for use as vasodilators for the regulation of high blood pressure in a subject.

In one embodiment, the method of promoting angiogenesis is applied to erectile dysfunction, which can be caused by vascular disorders. The use of the prominin-1 peptides described herein can treat impotence by encouraging repair of the penile vascular network.

In one embodiment, the method of promoting cell proliferation and/or promoting angiogenesis is applied in the context of wound healing, burn healing, myocardial infarction, tissue repair, fertility, erectile dysfunction, cardiac hypertrophy, tissue grafts, and/or tissue engineered constructs. A variety of tissues, or organs comprising organized tissues, requiring angiogenesis include but are not limited to the skin, muscle, gut, connective tissue, joints, bones and the like types of tissue in which blood vessels are required to nourish the tissue.

In one embodiment, the methods of promoting cell proliferation and/or promoting angiogenesis further comprise contacting a tissue with additional pro-angiogenic factors and/or growth promoting factors, e.g., VEGF, FGF, PDGF, and IGF.

In one aspect, promoting angiogenesis can protect severely hypertrophied hearts from ischemic injury. Myocardial hypertrophy is associated with progressive contractile dysfunction, increased vulnerability to ischemia-reperfusion injury, and is, therefore, a risk factor in cardiac surgery. During the progression of hypertrophy, a mismatch develops between the number of capillaries and cardiomyocytes (heart muscle cells) per unit area, indicating an increase in diffusion distance and the potential for limited supply of oxygen and nutrients. Treatment of hypertrophied hearts with VEGF resulted in an increase of microvascular density, improved tissue perfusion, and glucose delivery. (I. Friehs, et. al., 2004, The Annals of Thoracic Surgery, 77: 2004-2010). While not wishing to be bound by theory, the methods described herein for promoting cell proliferation and/or promoting angiogenesis can address this mismatch by potentiating the effect of VEGF in increasing the capillaries to improve the supply of nutrients to the cardiomyocytes.

In another aspect, promoting angiogenesis can stimulate bone repair and bone turnover. Several growth factors are known to be expressed in a temporal and spatial pattern during fracture repair. Exogenously added VEGF enhances blood vessel formation, ossification, and new bone maturation (Street, J. et. al., 2002, PNAS, 99:9656-61). Accordingly, the method described herein for promoting cell proliferation and/or promoting angiogenesis with prominin-1 peptide can be a therapy for bone repair. Bone repair assays are provided herein (see section entitled "Bone Repair Assays") to test the bone repair activity of pharmaceutical compositions comprising the peptides described herein.

In some aspects, the methods described herein for promoting cell proliferation and/or promoting angiogenesis are applicable to the treatment of wounds, and particularly for the treatment of persistent wounds, such as diabetic ulcers. Wounds, in particular persistent wounds, which are difficult to heal, require a blood supply that can nourish the wound, mediate the healing process and minimize scar formation. Commonly used therapies for treating persistent wounds do not assist the wound to provide its own blood supply and therefore the healing process remains slow. Persistent wounds can be ischemic wounds, for example, where the injury results from lack of oxygen due to poor circulation such as in diabetes, scleroderma, and the like. Scleroderma is a disease involving an imbalance in tissue reformation giving rise to the overproduction of collagen, and ultimately resulting in swelling and hardening of the skin (and affected organs). Diabetic wounds are especially difficult to treat because the inadequate blood supply is often complicated by other medical conditions such as peripheral vascular disease and neuropathy.

Agents such as the peptides described herein can be used to promote wound healing. A prominin-1 peptide used for wound healing will promote more rapid wound closure and/or greater angiogenesis at a given time relative to a similar wound not treated with the prom-1 peptide. Wound healing assays are provided herein (see section entitled "Wound Healing Assays") to test the wound healing activity of pharmaceutical compositions comprising the peptides described herein.

In one embodiment, the compositions described herein are administered topically to promote wound healing. In one embodiment, the peptides described herein are incorporated into a hydrogel or dressing or the like for use in the treatment of wounds. Alternatively, the prom-1 peptide compositions can be administered systemically. In other embodiments, the prom-1 peptide compositions can be administered directly to the organ or tissue in need in the context of a scaffold or gel material, e.g., directly to a bone fracture site.

In another embodiment, the compositions described herein are administered to the central nervous system to stimulate neuronal growth (e.g., neurite formation, axonal growth, axonal branching, and nerve tropism).

In some aspects, the methods described herein for promoting cell proliferation and/or promoting angiogenesis can promote angiogenesis in 3-D scaffold constructs of biodegradable polymeric scaffolds coated with the peptides or engineered to contain cells expressing nucleic acids encoding the peptide fragments. This equally applies to other scaffold materials (such as hydroxylapatite and metals). The emergence of the tissue engineering (TE) field has resulted in the development of various interdisciplinary strategies primarily aimed at meeting the need to replace organs and tissues lost due to diseases or trauma. In essence, the main TE approach is centered on seeding biodegradable scaffolds (both organic and inorganic such as poly(lactide-co-glycolide) and apatites) with donor cells, and optionally appropriate growth factor(s), followed by culturing and implantation of the scaffolds to induce and direct the growth of new, functional tissue. The scaffold material eventually disappears through biodegradation and is replaced by the specific tissue. This scaffold-guided TE approach is aimed at creating tissues such as skin, cartilage, bone, liver, heart, breast, etc.

Despite success with small (thin) tissue-engineered constructs, perhaps the biggest roadblock in scaffold-guided TE is engineering large tissue volumes. This challenge arises due to the lack of rapid vascularization (angiogenesis) of large three-dimensional (3-D) scaffold constructs. Accordingly, angiogenesis is a pre-requisite for scaffold-guided TE of large tissue volumes. Described herein is a method of promoting cell proliferation and/or promoting angiogenesis in a tissue-engineered construct, the method comprising contacting the tissue construct with a composition comprising a prom-1 peptide as that term is defined herein.

A number of biomolecules which induce or promote angiogenesis in tissues have been identified. The most prominent of these are: growth factors such as vascular endothelial growth factor (VEGF), fibroblast growth factor (FGF), epidermal growth factor (EGF), platelet-derived growth factors (PDGFs) and transforming growth factors (TGFs); and nitric oxide (NO). Therefore, in one embodiment, the method of promoting cell proliferation and/or promoting angiogenesis in a tissue-engineered construct further comprises administration of additional growth factors such as VEGF, FGF, EGF, PDGFs, TGFs, NO, and combinations thereof.

The patient treated according to the various embodiments described herein is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species.

In methods of treatment as described herein, the administration of prom-1 peptides can be for either "prophylactic" or "therapeutic" purpose. When provided prophylactically, the prom-1 peptides, variants, fusion protein, polymer of peptides, conjugates, mimetics and/or coding nucleic acids are provided in advance of any symptom. The prophylactic administration of the prom-1 peptides and/or coding nucleic acids serves to prevent or inhibit a disease or disorder associated with insufficient angiogenesis.

When provided therapeutically, a prom-1 peptide as described herein and/or coding nucleic acid thereof is provided at (or after) the onset of a symptom or indication of insufficient angiogenesis. Thus, the prom-1 peptides and/or coding nucleic acids can be provided either prior to the anticipated angiogenesis at a site or after the angiogenesis has begun at a site.

Angiogenesis Assays

Various methods of assaying for angiogenesis are described herein and referenced below. The complete content of these references is hereby incorporated by reference. In general, to measure the pro-angiogenic activity of an agent, e.g., a prominin-1 peptide as described herein, one will perform a given assay in the presence and absence of the peptide composition. Further, where the prom-1 peptides described herein interact with VEGF, it is preferred that the assays include VEGF (or another pro-angiogenic factor) as the baseline or control assay as well as in the prominin-1 containing assay.

Examples of well described angiogenesis assays that can be used to test or confirm pro-angiogenic activity of the peptides, variants, fusion proteins, peptidomimetics, peptide conjugates, or polymers of peptides or other derivatives described herein include, but are not limited to in vitro endothelial cell assays, rat aortic ring angiogenesis assays, cornea micro pocket assays (corneal neovascularization assays), and chick embryo chorioallantoic membrane assays (Erwin, A. et al. (2001) Seminars in Oncology 28(6):570-576).

Some examples of in vitro endothelial cell assays include methods for monitoring endothelial cell proliferation, cell migration, or tube formation. It is anticipated that prominin-1 peptides as described herein will affect each of these endothelial cell processes. Cell proliferation assays can use cell counting, BRdU incorporation, thymidine incorporation, or staining techniques (Montesano, R. (1992) Eur J Clin Invest 22:504-515; Montesano, R. (1986) Proc Natl. Acad. Sci. USA 83:7297-7301; Holmgren L. et al. (1995) Nature Med 1:149-153).

As one example of a cell proliferation assay, human umbilical vein endothelial cells are cultured in Medium 199 (Gibco BRL) supplemented with 10% fetal bovine serum (Gibco BRL), 50 U/ml penicillin, 50 ng/ml streptomycin, 2 mM L-glutamine and 1 ng/ml basic fibroblast growth factor (bFGF) in T75 tissue culture flasks (Nunclon) in 5% $CO_2$ at 37° C. Cells are trypsinised (0.025% trypsin, 0.265 mM EDTA, GibcoBRL) and seeded in 96-well plates (Nunclon) at a density of 3000 cells/well/200 µl and cultured for 3 days. Cells are starved in 1% serum for 24 hours and are then treated with 1% serum containing 1 ng/ml bFGF in the presence or absence of a pro-angiogenic agent for a further 48 hours. Two hours before the termination of incubation, 20 µl of CELL-TITER 96® Aqueous One Solution Reagent (Promega Inc.) is added into each well. After the completion of incubation at 37° C. in a humidified, 5% $CO_2$ atmosphere, the optical densities of the wells at 490 nm ("OD490") are recorded using a plate reader (Bio-Tek). The quantity of formazan product as measured by the amount of 490 nm absorbance is directly proportional to the number of living cells in culture.

Alternatively, the incubation period of cells with the pro-angiogenic factor can be allowed to proceed for up to 7 days. The cells are counted on a coulter counter on e.g., days 1, 3, 5 and 7. Remaining cells are fed by media replacement on these days. Data is plotted and doubling time calculated using a regression analysis (cells in log phase of growth). The doubling time for the cell is monitored as an indicator of cell proliferative activity.

In cell migration assays, endothelial cells are plated on matrigel and migration monitored upon addition of a chemoattractant (Homgren, L. et al. (1995) Nature Med 1:149-153; Albini, A. et al. (1987) Cancer Res. 47:3239-3245; Hu, G. et al. (1994) Proc Natl Acad Sci USA 6:12096-12100; Alessandri, G. et al. (1983) Cancer Res. 43:1790-1797.)

Another migration assay monitors the migration of bovine aortic endothelial cells. In the assay, bovine aortic endothelial (BAE) cells are allowed to grow to confluence in Dulbecco's modified Eagle medium (DMEM, GibcoBRL) containing 10% fetal bovine serum (GibcoBRL) in 12-well plates (Nunclon). The monolayers are then 'wounded' by scraping a disposable pipette tip across the dishes. After washing with Dulbecco's PBS plus calcium (0.1 g/L) (GIBCO™, Invitrogen Corporation), the wounded monolayers are cultured for a further 48 hours in fresh 1% serum in the presence or absence of a pro-angiogenic agent.

The degree of movement of cells in the wounded mono layers is determined by taking photomicrographs at the time of the initial wounding and 48 hours after wounding. The photomicrographs are taken at 20× magnification, e.g., on an Olympus CK2 inverted microscope and printed to a standard size of 15 cm wide by 10 cm deep. A grid with lines 1.5 cm apart and 10 cm long running parallel to a baseline is placed over the photograph. The baseline is placed on the "wounding line" above which the cells have originally been scraped off. The number of cells intercepted by each of the lines is recorded. This allows an assessment of the number of cells that have migrated 1.5, 3.0, 4.5, 6.0, 7.5 or 9.0 cm away from the baseline on the photomicrograph.

Endothelial tube formation assays monitor vessel formation (Kohn, E C. et al. (1995) Proc Natl Acad Sci USA 92:1307-1311; Schnaper, H W. et al. (1995) J Cell Physiol 165:107-118).

Rat aortic ring assays have been used successfully for the evaluation of angiogenesis drugs (Zhu, W H. et al., (2000) Lab Invest 80:545-555; Kruger, E A. et al., (2000) Invasion Metastas 18:209-218; Kruger, E A. et al., (2000) Biochem Biophys Res Commun 268:183-191; Bauer, K S. et al. (1998) Biochem Pharmacol 55:1827-1834; Bauer, K S. et al., (2000) J Pharmacol Exp Ther 292:31-37; Berger, A C. et al., (2000) Microvasc Res 60:70-80.). Briefly, the assay is an ex vivo model of explant rat aortic ring cultures in a three dimensional matrix. One can visually observe either the presence or absence of microvessel outgrowths. The human saphenous angiogenesis assay, another ex vivo assay, can also be used (Kruger, E A. et al. (2000) Biochem Biophys Res Commun 268:183-191).

Another common angiogenesis assay is the corneal micropocket assay (Gimbrone, M A. et al., (1974) J Natl Canc Inst. 52:413-427; Kenyon, B M. et al., (1996) Invest Opthalmol V is Sci 37:1625-1632; Kenyon, B M. et al., (1997) Exp Eye Res 64:971-978; Proia, A D. et al., (1993) Exp Eye Res 57:693-698). Briefly, neovascularization into an avascular space is monitored in vivo. This assay is commonly performed in rabbit, rat, or mouse.

The chick embryo chorioallantoic membrane assay has been used often to study tumor angiogenesis, angiogenic factors, and antiangiogenic compounds (Knighton, D. et al. (1977) Br J Cancer 35:347-356; Auerbach, R. et al. (1974) Dev Biol 41:391-394; Ausprunk, D H. et al. (1974) Dev Biol 38:237-248; Nguyen, M. et al. (1994) Microvasc Res 47:31-40). This assay uses fertilized eggs and monitors the formation of primitive blood vessels that form in the allantois, an extra-embryonic membrane. This assay functions as an in vivo endothelial cell proliferation assay.

Other in vivo angiogenesis assays are described in U.S. Pat. No. 5,382,514 and the directed in vivo angiogenesis assay (DIVAA™) system made by Trevigen, Inc. In these assays, a pro-angiogenic factor is incorporated into a tissue compatible matrix or hydrogel material such as Matrigel (GibcoBDL) or in the angioreactor Cultrex® DIVAA™, the matrix material or angioreactor is implanted subdermally into nude mice. Over time, usually days, microvessels invade the matrix material or angioreactor. The matrix material or angioreactor are then excised from the host mouse and examined.

Wound Healing Assays

The prominin-1 peptides described herein can be used to facilitate, enhance or accelerate wound healing. Wound healing, or wound repair, is an intricate process in which the skin (or some other organ) repairs itself after injury. The classic model of wound healing is divided into four sequential, yet overlapping, phases: (1) hemostasis, (2) inflammatory, (3) proliferative and (4) remodeling. Angiogenesis occurs during the proliferative phase of wound healing and promotes wound contraction (i.e., a decrease in the size of the wound). Microvascular in-growth into damaged tissue is an essential component of the normal healing process. In fact, wound therapy is often aimed at promoting neovascularization.

Thus, a wound healing assay can be used as an angiogenesis assay to assess the effect of a given prom-1 peptide, variant, or derivative described herein. Such wound healing assays include, but are not limited to, ear punch assays and full thickness dorsal skin assays. Wound healing assays can be performed as described in U.S. Published Application No. 20060147415, entitled "Composition and method for treating occlusive vascular diseases, nerve regeneration and wound healing," which is incorporated herein by reference in its entirety. The term "full thickness" is used herein to describe a wound that includes the epidermal layer and at least a portion of the dermal layer. The term "full thickness" also encompasses a deep wound to the level of the panniculus carnosus that removes epidermal, dermal, subcutaneous, and fascia layers.

Full thickness dorsal skin wounding assays can be performed as described in e.g., Luckett-Chastain, L R and Galluci, R M, Br J Dermatol. (2009) Apr. 29; Shaterian, A et al., Burns (2009) May 5; Lee, W R, et al., Wound Repair Regen (2009) Jun. 12; and Safer, J D, et al., Endocrinology (2005) 146(10):4425-30, which are herein incorporated by reference in their entirety. Dorsal skin wounding assays can be performed using rat or mouse models.

Whereas, the ear punch wound assay is used to generate the wound healing data described herein, it is expected that any of the other wound healing assays described herein will provide similar or superior results with prom-1 peptides as described. In one embodiment, a full-thickness wound is effected by removing a section of skin (e.g., 1.5 mm diameter) from the dorsal surface (e.g., back) of an anesthetized animal by e.g., surgical incision. If so desired, the section of skin to be wounded can be pre-treated with a candidate pro-angiogenic factor prior to wound induction by e.g., subcutaneous injection. Alternatively, the wound can be treated using a candidate pro-angiogenic factor coincident with or immediately following wounding using methods known to one of skill in the art. The size, area, rate of healing, contraction and histology of the wound are assessed at different time points by methods known to those of skill in the art. The wound size of an animal is assessed by measuring the unclosed wound area compared to the original wound area. Wound healing can be expressed as either percent wound closure or percent wound closure rate. Wounds can be harvested at different time points by euthanizing the animal and removing a section of skin surrounding the wound site for histological analysis if so desired.

The capacity of a candidate pro-angiogenic factor to induce or accelerate a healing process of a skin wound can be determined by administering the candidate pro-angiogenic factor to skin cells colonizing the damaged skin or skin wound area and evaluating the treated damaged skin or wounds for e.g., angiogenesis and/or epidermal closure and/or wound contraction. As known to those of skill in the art, different administration methods (e.g., injection or topical administration) can be used to treat the skin wound, and different concentrations of the candidate pro-angiogenic factor can be tested. A statistically significant increase in the incidence of vessel formation and/or epidermal closure and/or wound contraction, over an untreated control, indicates that a tested candidate pro-angiogenic factor is capable of inducing or accelerating a healing process of a damaged skin or skin wound. Positive results are indicated by a reduction in the percent wound area of a mouse treated with a candidate pro-angiogenic factor of at least 5% compared to the wound area of an untreated or vehicle treated mouse at the same timepoint; preferably the reduction in percent wound area is at least 7%, at least 8%, at least 9%, at least 10%, at least 12%, at least 15%, at least 20%, at least 25%, at least 30%, at least 35%, at least 40%, at least 50%, at least 60%, at least 70%, at least 80%, at least 90%, at least 95%, at least 99%, or even 100% (i.e., wound is completely closed).

An ear punch model can also be used to assess rates of angiogenesis or wound healing, in a design similar to that for the full thickness dorsal back skin assay. The model consists of wounding the ear of an animal using a circular punch of a standard size (e.g., 2.25 mm). The wound is treated daily with either a matrigel vehicle or a matrigel containing a candidate pro-angiogenic factor. This assay is further described herein in the Examples section.

Neurodegenerative Diseases

VEGF has neurotrophic and neuroprotective effects. Given the effects of prom-1 peptides as described herein on VEGF-mediated angiogenesis, and parallels between VEGF's pro-angiogenic and neurotrophic activities, it is anticipated that prom-1 peptides as described herein can potentiate or enhance the neurotrophic or neuroprotective effects of VEGF. The prom-1 peptides can be used to treat neurodegenerative diseases as described in e.g., U.S. Published Application No. 20060147415, entitled "Composition and method for treating occlusive vascular diseases, nerve regeneration and wound healing," which is incorporated herein by reference in its entirety. Furthermore, the prom-1 peptides described herein can be used to stimulate neuronal growth, axonal elongation, axonal branching and neurite formation.

In one embodiment, the prom-1 peptide compositions described herein are used as neuroprotective agents to prevent and/or treat diseases associated with neurodegeneration or nerve damage. Thus, in one embodiment, provided herein is a method of promoting neuroprotection, the method comprising contacting a neuronal cell with an isolated prom-1 peptide of a prominin polypeptide, wherein the peptide binds VEGF, and wherein the contacting promotes neuroprotection of the neuronal cell. In another embodiment, the contacting of the neuronal cell prevents or delays neuronal cell death relative to neuronal cell death occurring in the absence of such contacting, or wherein such contacting promotes nerve regeneration by stimulating neuronal growth.

Neurodegeneration or nerve damage can result from e.g., stroke, heat stress, head and spinal cord trauma, and bleeding that occurs in the brain, the pressure from which eventually causes the death of one or more neurons; often neuronal death begins long before the patient will ever experience any symptoms.

Neurodegeneration can also be a result of neurodegenerative diseases caused by the deterioration of neurons, which over time leads to physical manifestations. Neurodegenerative diseases of the central nervous system include e.g., intracerebral hemorrhage (ICH), neurodegenerative diseases such as Alzheimer's disease, Parkinson's disease and other degenerative diseases of the basal ganglia; other neurological causes of memory loss or impairment, including Down's syndrome, Creutzfeldt-Jakob disease, prion diseases, cerebral ischemia and stroke; multiple sclerosis; motor neuron disease, such as amyotropic lateral sclerosis; neurological viral disease; post-surgical neurological dysfunction; Huntington's disease; hereditary spastic hemiplegia; primary lateral sclerosis; spinal muscular atrophy; Kennedy's disease; Shy-Drager syndrome; Progressive Supranuclear Palsy; Lewy Body Disease; neuronopathies; dementia; frontotemporal lobe dementia; ischemic disorders (e.g., cerebral or spinal cord infarction and ischemia, chronic ischemic brain disease, and stroke); kaumas (e.g., caused by physical injury or surgery, and compression injuries); affective disorders (e.g., stress, depression and post-traumatic depression); neuropsychiatric disorders (e.g., schizophrenia, multiple sclerosis, and epilepsy); learning and memory disorders; trigeminal neuralgia; glossopharyngeal neuralgia; Bell's Palsy; myasthenia gravis; progressive muscular atrophy; progressive bulbar inherited muscular atrophy; herniated, ruptured and prolapsed vertebrate disk syndromes; cervical spondylosis; plexus disorders; thoracic outlet destruction syndromes; peripheral neuropathies; prophyria; muscular dystrophy; a polyglutamine repeat disease; and spongiform encephalopathy. Ocular neuron disorders can also be treated with peptides as described herein and include, but are not limited to, retina or optic nerve disorders; optic nerve damage and optic neuropathies such as Lebers hereditary optic neuropathy, autosomal dominant optic atrophy, optic neuritis; disorders of the optic nerve or visual pathways; toxic neuropathies and toxic retinopathies; optic atrophy; glaucoma; retinal degenerations such as retinitis pigmentosa, macular degeneration, and diabetic retinopathy.

Neuroprotective effects of peptide compositions as described herein can be measured using in vivo or in vitro assays that assess e.g., neuron survival, neuron growth, neurite production, re-innervation, improved behavioral symptoms etc. As one example, in vitro assays of neurite outgrowth can be used to evaluate or monitor the neuroprotective effects of peptide compositions as described herein. In vitro assays of neurite growth are well known in the art and are described in, for example, Jin and Strittmatter, *J Neurosci* 17:6256-6263 (1997); Fournier et al., *Methods Enzymol.* 325:473-482 (2000); Zheng et al., *Neuron* 38:213-224 (2003); Wang et al., *Nature* 417:941-944 (2002), and Neumann et al., *Neuron* 34:885-893 (2002), which are all incorporated herein by reference in their entirety. Kits for measuring and quantifying neurite outgrowth are commercially available from e.g., Chemicon (Billerica, Mass.), Millipore (Billerica, Mass.), and Thermo Scientific Pierce Protein Research Products (Rockford, Ill.). Thus, for example, CHEMICON's Neurite Outgrowth Assay Kit (Catalog number NS200) uses microporous filter technology for the quantitative testing of compounds that influence neurite formation and repulsion. With this system, it is possible to analyze biological and pharmacological agents simultaneously, directly evaluate adhesion and guidance receptor functions responsible for neurite extension and repulsion, as well as the analysis of gene function in transfected cells. The microporous filter allows for biochemical separation and purification of neurites and cell bodies for detailed molecular analysis of protein expression, signal transduction processes and identification of drug targets that regulate neurite outgrowth or retraction processes.

In one embodiment, an in vitro neurite cell-based assay involves culturing neuronal cells in the presence and absence of a candidate neuroprotective agent (e.g., a peptide composition as described herein) and determining the change in neurite length. The agent is identified or confirmed as neuroprotective when the neurite length is longer in the presence of the candidate agent than the length of a neurite in untreated cells. Assays will generally be performed in the presence of VEGF, plus and minus a prom-1 peptide composition. In such a cell-based assay, the neuronal cells can be primary neurons, or can, for example, be derived from cells or cell lines, including stem cells, e.g., embryonic stem (ES) cells. In other embodiments, the neurons can, for example, be selected from the group consisting of cerebellar granule neurons, dorsal root ganglion neurons, and cortical neurons. In a typical protocol, primary neurons isolated from rodent neural tissue (including cerebellar granule neurons, dorsal root ganglion neurons, and cortical neurons) are cultured on 96-well tissue culture dishes coated with immobilized whole myelin or myelin associated proteins (e.g., Nogo66, MAG and/or OMgp). Following a defined time in culture, typically 24-48 hours, the neurons are fixed with 4% paraformaldehyde and stained with a neuronal marker (anti-class III b-Tubulin, Covance). Image acquisition and analysis are then performed using e.g., the ImageXpress automated imaging system (Molecular Devices). Data are analyzed for changes in maximal or total neurite length per neuron. An enhanced neurite growth response in the presence of a prom-1 peptide as described herein confirms the neurotrophic and/or neuroprotective effects of the given prom-1 peptide (see Example 10).

In vivo assays are known to those of skill in the art and include animal models of various neurodegenerative diseases, such as spinal cord injury models, visual cortex plasticity models, and other models known in the art. Thus, regeneration and plasticity can be studied in models of plasticity following unilateral pyramidotomy and models of traumatic brain injury. Other models of neurodegeneration include mouse models of multiple sclerosis, such as experimental autoimmune encephalitis (EAE), models of amyotrophic lateral sclerosis (ALS), such as the SODI mutant mouse, transgenic animal models of Alzheimer's disease, and animal models of Parkinson's. The beneficial effect of prom-1 peptide administration can be evaluated or confirmed in any of these assays, e.g., by administering VEGF alone or VEGF and a prom-1 peptide as described herein. Alternatively, it is contemplated that prom-1 peptides can act in such assays without exogenously added VEGF or other pro-angiogenic or neurotrophic agents.

In one embodiment, neuronal regeneration is assessed by measuring axonal regeneration in a model of optic nerve crushing (Fischer D, et al., *J. Neurosci.* 18, 1646 (2004)). In a typical protocol, adult mouse optic nerves are exposed behind the eyeball and crushed. Immediately after injury in adult mice, Gelfoam soaked in a solution containing a peptide described herein or vehicle control is placed against the crush site of the nerve and replaced every three days for the first six days. Animals are sacrificed two weeks post injury followed by transcardial perfusion with 4% paraformaldehyde. Optic nerves are cryosectioned at 10 μm and stained with an anti-GAP43 antibody (Chemicon) to detect regenerating axons.

Other in vivo assays include assessing behavioral changes in peptide treated and untreated animal models of neurodegenerative disease. For example, akinesia is measured by noting the latency in seconds (s) of the animals to move all four limbs. In a typical protocol, each animal is initially acclimatized for 5 min on a wooden elevated platform (40 cm×40 cm×30 cm) used for measuring akinesia in mice. Using a stopwatch, the time taken (s) by the animal to move all four limbs is recorded. In general, measurement is stopped once the latency period reaches 180 sec. Another behavioral measure is catalepsy, which refers to the inability of an animal to correct an externally imposed posture. In one embodiment, catalepsy is measured by placing the animal on a flat horizontal surface with both the hind limbs on a square wooden block (3 cm high) and the latency in seconds is measured to move the hind limbs from the block to the ground. A swim test is also used for measuring the extent of neurodegeneration in an animal model. Swim-tests are carried out following treatment of the animals with a peptide and are performed in water tubs. In a typical protocol, the depth of water is about 12 cm and the temperature maintained at around 27° C. Animals are scored for swim tests according to the following scale: 0, hind part sinks with head floating; 1, occasional swimming using hind limbs while floating on one side; 2, occasional floating/swimming only; 3, continuous swimming (see Haobam et al. (2005) Behay. Brain Res. 163, 159-167). The beneficial neuroprotective or neurotrophic effects of prom-1 peptides described herein would be confirmed by a statistically significant improvement in any of the behaviors monitored by these assays.

Clinically, an effective dose of a peptide described herein, or effective regimen, is a combination of dose and dosing that provides for an improvement in the symptoms associated with the particular neuronal or neurodegenerative disease, e.g., Parkinson's disease as assessed by the United Parkinson's Disease Rating Scale (UPDRS), or the use of surrogate markers. For example, the motor abilities of a Parkinson's patient may improve, where motor symptoms may include motor fluctuations, dyskinesias, off-period dystonia, freezing, and falls. Alternatively, improvement may be assessed by imaging, e.g., by monitoring of dopamine uptake, or striatal neuron function. The standard tool for tracking Parkinson's disease progress and response to therapy is the United Parkinson's Disease Rating Scale (UPDRS). The UPDRS is subdivided into three scales including cognitive and mood aspects, motor aspects, and activities of daily living (ADL). A lower score indicates a better condition than a higher score. The UPDRS is readily available, e.g., see Fahn S, Elton R, Members of the UPDRS Development Committee, In: Fahn S, Marsden C D, Caine D B, Goldstein M, eds. Recent Developments in Parkinson's Disease, Vol 2. Florham Park, N.J. Macmillan Health Care Information 1987, pp 15 3-163, 293-304.

Further clinical tests for assessing neuroprotection can be used in the clinical setting by those of skill in the art of medicine. The treatment of a neurodegeneration as a result of brain injury can be monitored by employing a variety of neurological measurements. For example, a therapeutic response can be monitored by determining if, for example, there is an improvement in the subject's: a) maximum daily Glasgow Coma Score; b) duration of coma; 3) daily intracranial pressure (ICP)—therapeutic intensity levels; 4) extent of cerebral edema/mass effect measured on serial CT scans; and, 5) duration of ventilator support. A brief description of each of these measurements is provided below.

The Glasgow Coma Score (index GCS) is a reflection of the depth of impaired consciousness and is best obtained following initial resuscitation (oxygenation, rehydration and support of blood pressure) but prior to use of sedating drugs, neuromuscular blocking agents, or intubation.

The ICP of patients with severe brain injury is often monitored with an intracranial pressure device. Monitoring ICP can provide a measure of cerebral edema. However, inherent variability and analysis complexities due to therapeutic intervention exist. To adjust for these interventions a therapeutic intensity scale was developed. This scale, known as the Therapeutic Intensity Level (TIL), measures treatment aggressiveness for elevated ICPs (Allolio et al. (1995) European Journal of Endocrinology 133(6): 696-700; Adashi et al. (1996) Reproductive endocrinology, surgery, and technology Philadelphia: Lippincott-Raven; and, Beers et al. eds. (1999) The Merck Manual of Diagnosis and Therapy. 17th ed., Merck Sharp & Dohme Research Laboratories, Rahway, N.J.).

The extent of cerebral edema and mass effect can be determined by CT scans. For example, the volume of focal lesions can be measured. Mass lesions, either high-density or mixed-density abnormalities, are evaluated by measuring the area of the abnormality as a region of interest, multiplying the area by the slice thickness, and summing these volumes for contiguous slices showing the same lesion. Each lesion is measured three times, and the mean volume entered. This technique has been shown to be reliable (Garcia-Estrada et al. (1993) Brain Res 628(1-2): 271-8). Intracerebral lesions can be further characterized by location (frontal, temporal, parietal, occipital, basal ganglia, or any combination).

In addition to the neurological measurements discussed above, a therapeutic response can also be assayed through various functional and neuropsychological outcomes. Several standardized measures of neuropsychological and functional performance are known. For instance subjects may display an improvement in the Glasgow Outcome Scale (GOS)/Glasgow Outcome Scale Extender (GOSE) and/or in the Disability Rating Scale (DRS). The Glasgow Outcome Score is one of the most widely used measures of brain injury recovery in the world (Garcia-Estrada et al. (1999) Int J Dev Neurosci 17(2): p. 145-51). Patients are classified into one of five categories: death, persistent vegetative state, severe disability, moderate disability, and good recovery. It is easy to administer and score, and has a high degree of reliability and validity. The Disability Rating Scale (DRS) offers more precision than the GOS for measuring outcomes of moderate brain injury (Goodman et al. (1996) *J Neurochem* 66(5): 1836-44). The DRS consists of an eight-item rating of arousal and awareness, daily living activities, physical dependence, and employability (Vedder et al. (1999) *J Neurochem* 72(6): 2531-8). Inter-rater reliability for the entire DRS is high (0.97 to 0.98).

The Functional Independence Measure (FIM) can be used to assess physical and cognitive disability. It contains 18 items in the following domains: self-care, sphincter control, mobility, locomotion, communication, and social cognition (Baulieu (1997) *Mult Scler* 3(2):105-12). The FIM has demonstrated reliability and validity as an outcome measure following moderate and severe TBI (Jung-Testas et al. (1994) *J Steroid Biochem Mol Biol* 48(1):145-54).

The Sickness Impact Profile is one method for measuring self-perceived health status (Schumacher et al. (1995) *Ciba Found Symp* 191: p. 90-112 and Koenig et al. (1995) *Science* 268(5216):1500-3). It consists of 136 questions divided into 12 categories: sleep and rest, eating, work, home management, recreation and pastimes, ambulation, mobility, body care and movement, social interaction, alertness, behavior, emotional behavior, and communication. It has been widely used across a variety of diseases and injuries, including head injury (Thomas et al. (1999) Spine 24:2134-8). Baseline SIP scores will reflect pre-injury health status, while follow-up scores will examine post-injury functioning.

In one embodiment, the compositions described herein are administered to the central nervous system to stimulate neuronal growth (e.g., neurite formation, axonal growth, axonal branching, and nerve tropism).

Bone Repair Assays

Method 1: Each mouse is anesthetized with a ketamine/xylazine anesthetic and an incision is made over the anteromedial surface of the right tibial diaphysis. The muscle is blunt dissected to expose the periosteal surface and a 0.6 mm diameter penetrating hole is created in the medial cortex approximately 1 mm distal from the termination of the tibial tuberosity. Following surgery and/or treatment with the peptides described herein, all animals undergo high resolution micro-CT scan (Scanco vivaCT 40; 11 μm voxel resolution) to confirm the fracture. A second and third micro-CT scan are performed in all animals at 12 and 21 days, respectively to monitor the progress of bone healing and provide a quantitative analysis of the bone mineral density at the fracture site.

Method 2: Each mouse is anesthetized with a ketamine/xylazine anesthetic and a small incision is made on the dorsolateral side of the thigh and extended over the knee region. A longitudinal incision is made in the patellar tendon, and a 0.5 mm hole is drilled above the tibia tuberosity. A fracture is then made by cutting the shaft of tibia. A fracture generated in this manner is known to heal through both endochondral and intramembranous ossification.

Alternatively, the calvarial bone repair assay describe in Example 12 can be used.

Peptides described herein are mixed with MATRIGEL™ and injected into the fracture site using a microsyringe. The animals are allowed free, unrestricted weight bearing in cages after recovery from anesthesia. At different time points (3, 4, 7, 14, and 21 d) after the fracture, the bone mineral density at the fracture site is analyzed using a Small Animal Bone Densitometer.

Pro-Angiogenic Factors

Pro-angiogenic factors are factors that directly or indirectly promote new blood vessel formation. These factors can be expressed and secreted by normal and tumor cells. Pro-angiogenic factors derived from prom-1 as described can be administered in combination with other pro-angiogenic factors including, but not limited to, EGF, E-cadherin, VEGF (particularly VEGF isoforms: VEGF 121, 145 and 165), angiogenin, angiopoietin-1, fibroblast growth factors: acidic (aFGF) and basic (bFGF), fibrinogen, fibronectin, heparanase, hepatocyte growth factor (HGF), insulin-like growth factor-1 (IGF-1), IGF, BP-3, PDGF, VEGF-A VEGF-C, pigment epithelium-derived factor (PEDF), vitronection, leptin, trefoil peptides (TFFs), CYR61 (CCN1) and NOV (CCN3), leptin, midkine, placental growth factor platelet-derived endothelial cell growth factor (PD-ECGF), platelet-derived growth factor-BB (PDGF-BB), pleiotrophin (PTN), pro-granulin, proliferin, transforming growth factor-alpha (TGF-alpha), transforming growth factor-beta (TGF-beta), tumor necrosis factor-alpha (TNF-alpha), c-Myc, granulocyte colony-stimulating factor (G-CSF), stromal derived factor 1 (SDF-1), scatter factor (SF), osteopontin, stem cell factor (SCF), matrix metalloproteinases (MMPs), thrombospondin-1 (TSP-1), and inflammatory cytokines and chemokines that are inducers of angiogenesis and increased vascularity, eg. CCL2 (MCP-1), interleukin-8 (IL-8) and CCL5 (RANTES).

Synthesis of Peptides

Prom-1 peptides, including variants and derivatives thereof can be chemically synthesized and purified by biochemical methods that are well known in the art such as solid phase peptide synthesis using t-Boc (tert-butyloxycarbonyl) or FMOC (9-flourenylmethloxycarbonyl) protection group described in "Peptide synthesis and applications" in Methods in molecular biology Vol. 298, Ed. by John Howl and "Chemistry of Peptide Synthesis" by N. Leo Benoiton, 2005, CRC Press, (ISBN-13: 978-1574444544) and "Chemical Approaches to the Synthesis of Peptides and Proteins" by P. Lloyd-Williams, et. al., 1997, CRC-Press, (ISBN-13: 978-0849391422), Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954 and these are all hereby incorporated by reference in their entirety.

Solid phase peptide synthesis, developed by R. B. Merrifield, 1963, J. Am. Chem. Soc. 85 (14): 2149-2154, was a major breakthrough allowing for the chemical synthesis of peptides and small proteins. An insoluble polymer support (resin) is used to anchor the peptide chain as each additional alpha-amino acid is attached. This polymer support is constructed of 20-50 µm diameter particles which are chemically inert to the reagents and solvents used in solid phase peptide synthesis. These particles swell extensively in solvents, which makes the linker arms more accessible.

Organic linkers attached to the polymer support activate the resin sites and strengthen the bond between the alpha-amino acid and the polymer support. Chloromethyl linkers, which were developed first, have been found to be unsatisfactory for longer peptides due to a decrease in step yields. The PAM (phenylacetamidomethyl) resin, because of the electron withdrawing power of the acid amide group on the phenylene ring, provides a much more stable bond than the classical resin. Another alternative resin for peptides under typical peptide synthesis conditions is the Wang resin. This resin is generally used with the FMOC labile protecting group.

A labile group protects the alpha-amino group of the amino acid. This group is easily removed after each coupling reaction so that the next alpha-amino protected amino acid may be added. Typical labile protecting groups include t-Boc (tert-butyloxycarbonyl) and FMOC. t-Boc is a very satisfactory labile group which is stable at room temperature and easily removed with dilute solutions of trifluoroacetic acid (TFA) and dichloromethane. FMOC is a base labile protecting group which is easily removed by concentrated solutions of amines (usually 20-55% piperidine in N-methylpyrrolidone). When using FMOC alpha-amino acids, an acid labile (or base stable) resin, such as an ether resin, is desired.

The stable blocking group protects the reactive functional group of an amino acid and prevents formation of complicated secondary chains. This blocking group must remain attached throughout the synthesis and may be removed after completion of synthesis. When choosing a stable blocking group, the labile protecting group and the cleavage procedure to be used should be considered.

After generation of the resin bound synthetic peptide, the stable blocking groups are removed and the peptide is cleaved from the resin to produce a "free" peptide. In general, the stable blocking groups and organic linkers are labile to strong acids such as TFA. After the peptide is cleaved from the resin, the resin is washed away and the peptide is extracted with ether to remove unwanted materials such as the scavengers used in the cleavage reaction. The peptide is then frozen and lyophilized to produce the solid peptide. This is generally then characterized by HPLC and MALDI before being used. In addition, the peptide should be purified by HPLC to higher purity before use.

Commercial peptide synthesizing machines are available for solid phase peptide synthesis. For example, the Advanced Chemtech Model 396 Multiple Peptide Synthesizer and an Applied Biosystems Model 432A Peptide synthesizer are suitable. There are commercial companies that make custom synthetic peptides to order, e.g., Abbiotec, Abgent, AnaSpec Global Peptide Services, LLC. Invitrogen and rPeptide, LLC.

The prom-1 peptides and derivatives thereof can also be synthesized and purified by molecular methods that are well known in the art. For example, recombinant protein may be expressed in bacteria, mammal, insect, yeast, or plant cells.

Conventional polymerase chain reaction (PCR) cloning techniques can be used to clone a nucleic acid encoding a prom-1 peptide, using the mRNA of the intact full length prom-1 as the template for PCR Cloning. Alternatively, the sense and anti-sense strand of the coding nucleic acid can be made synthetically and then annealed together to form the double-stranded coding nucleic acid. Ideally, restriction enzyme digestion recognition sites should be designed at the ends of the sense and anti-sense strand to facilitate ligation into a cloning vector or other vectors. Alternatively, a 3'A overhang can be include for the purpose of TA-cloning that is well known in the art. Such coding nucleic acids with 3'A overhangs can be easily ligated into the Invitrogen topoisomerase-assisted TA vectors such as pCR®-TOPO, pCR®-Blunt II-TOPO, pENTR/D-TOPO®, and pENTR/SD/D-TOPO®. The coding nucleic acid can be cloned into a general purpose cloning vector such as pUC19, pBR322, pBluescript vectors (Stratagene Inc.) or pCR TOPO® from Invitrogen Inc. The resultant recombinant vector carrying the nucleic acid encoding a prom-1 peptide can then be used for further molecular biological manipulations such as site-directed mutagenesis for variant prom-1 peptide and/or to reduce the immunogenic properties of the peptide or improve protein expression in heterologous expression systems, or can be subcloned into protein expression vectors or viral vectors for the synthesis of fusion protein comprising prom-1 peptides and protein synthesis in a variety of protein expression systems using host cells selected from the group consisting of mammalian cell lines, insect cell lines, yeast, bacteria, and plant cells.

In one embodiment, the invention provides cells engineered to express nucleic acids encoding peptides of the invention. Preferably, the cells are eukaryotic cells. The nucleic acids are operationally linked to a promoter. The expression construct can further comprise a secretory sequence to assist purification of the peptide from the cell culture medium.

In one embodiment, a sense nucleic acid encoding LCGNSFSGGQPS (SEQ ID NO: 4) is 5' CTGTGCGGCAA-CAGCTTTAGCGGCGGCCAGCCGAGC 3'(SEQ. ID. No. 10) and the complementary anti-sense nucleic acid is 5' is GCTCGGCTGGCCGCCGCTAAAGCTGT-TGCCGCACAG 3'(SEQ. ID. No. 11).

PCR amplified coding nucleic acids or annealed sense and anti-sense nucleic acid with 3'A overhang can cloned into a vector using the TOPO® cloning method in Invitrogen topoisomerase-assisted TA vectors such as pCR®-TOPO, pCR®-Blunt II-TOPO, pENTR/D-TOPO®, and pENTR/SD/D-TOPO®. Both pENTR/D-TOPO®, and pENTR/SD/D-TOPO® are directional TOPO entry vectors which allow the cloning of the DNA sequence in the 5'→3' orientation into a Gateway® expression vector. Directional cloning in the 5'→3' orientation facilitate the unidirectional insertion of the DNA sequence into a protein expression vector such that the promoter is upstream of the 5' ATG start codon of the nucleic acid, thus enabling promoter-driven protein expression. The recombinant vector carrying a prom-1 peptide coding nucleic acid can be transfected into and propagated in a general cloning E. coli cells such as XL1Blue, SURE (Stratagene) and TOP-10 cells (Invitrogen).

It is envisioned that multiple copies of the nucleic acid encoding prom-1 peptide can be ligated in tandem such that a polymer of prom-1 peptides can be expressed. Protease cleavage sites can be designed and included between the nucleic acid to facilitate liberation of each prom-1 peptide from the polymeric prom-1 peptide if so desired. Examples of protease cleavage sites include but are not limited to those of enterokinase, chymotrypsin, and thrombin.

Methods of making conservative amino acid substitutions are also well known to one skilled in the art and include but are not limited to site-specific mutagenesis using oligonucleotide primers and polymerase chain reactions. A conservative substitution variant of a prom-1 peptide of 12 or fewer amino acids (as a non-limiting example, the #237 prom-1 peptide) described herein can have 1 to 4 conservative amino acid substitutions but will, as will all prom-1 peptide variants or derivatives, substantially retain VEGF binding activity. In one embodiment, the 1-4 substitutions are not located within the 6 C-terminal amino acids of the #237 peptide. In another embodiment, the substitutions do not change the C-terminal alanine and valine amino acids of the #237 peptide. Variant prom-1 peptides can be expressed and assayed for VEGF-binding activity, regenerative, pro-angiogenic activity, promotion of cell proliferation activity, and/or promotion cell migration activity by methods known in the art and/or described herein to verify that these activities specific to each prom-1 peptide are not abolished by the amino acid substitutions. Variant prom-1 peptides have at least 50% of the VEGF-binding activity, regenerative, pro-angiogenic activity, promotion of cell proliferation activity, promotion of cell migration, or neurotrophic/neuroprotective activity of the original parent prom-1 peptide. It is contemplated that conservative amino acid substitution variants of prom-1 peptides as described herein can have enhanced activity or superior stability relative to the parent prom-1 peptide.

Certain silent or neutral missense mutations can also be made in the nucleic acid encoding a prom-1 peptide by a mutation that does not change the encoded amino acid sequence or the regenerative and/or pro-angiogenic or anti-angiogenic activities of the encoded prom-1 peptide. These types of mutations are useful to optimize codon usage which improves recombinant protein expression and production.

Specific site-directed mutagenesis of a nucleic acid encoding a prom-1 peptide in a vector can be used to create specific amino acid mutations and substitutions. Site-directed mutagenesis can be carried out using, e.g., the QUIKCHANGE® site-directed mutagenesis kit from STRATAGENE® according to manufacture's instructions, or by any method known in the art.

Different expression vectors comprising a nucleic acid that encodes a prom-1 peptide or derivative as described herein for the expression and purification of the recombinant protein produced from a heterologous protein expression system can be made. Heterologous protein expression systems that use host cells selected from, e.g., mammalian, insect, yeast, bacterial, or plant cells are well known to one skilled in the art. The expression vector should have the necessary 5' upstream and 3' downstream regulatory elements such as promoter sequences, ribosome recognition and binding TATA box, and 3' UTR AAUAAA transcription termination sequence for efficient gene transcription and translation in its respective host cell. The expression vector may have additional sequence such as 6X-histidine (SEQ ID NO: 19), V5, thioredoxin, glutathione-S-transferase, c-Myc, VSV-G, HSV, FLAG, maltose binding peptide, metal-binding peptide, HA and "secretion" signals (Honeybee melittin, α-factor, PHO, Bip), which are incorporated into the expressed recombinant prom-1 peptide. In addition, there can be enzyme digestion sites incorporated after these sequences to facilitate enzymatic removal of additional sequence after they are not needed. These additional sequences are useful for the detection of prom-1 peptide expression, for protein purification by affinity chromatography, enhanced solubility of the recombinant protein in the host cytoplasm, for better protein expression especially for small peptides and/or for secreting the expressed recombinant protein out into the culture media, into the periplasm of the prokaryote bacteria, or to the spheroplast of yeast cells. The expression of recombinant prom-1 peptide can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose, depending on the host and vector system chosen.

Recombinant prom-1 peptide can be expressed in a variety of expression host cells e.g., bacteria, such as *E. coli*, yeast, mammalian, insect, and plant cells such as *Chlamydomonas*, or even from cell-free expression systems. From a cloning vector, the nucleic acid can be subcloned into a recombinant expression vector that is appropriate for the expression of the prom-1 peptide in mammalian, insect, yeast, bacterial, or plant cells or a cell-free expression system such as a rabbit reticulocyte expression system. Subcloning can be achieved by PCR cloning, restriction digestion followed by ligation, or recombination reaction such as those of the lambda phage-based site-specific recombination using the Gateway® LR and BP Clonase™ enzyme mixtures. Subcloning should be unidirectional such that the 5' ATG start codon of the nucleic acid is downstream of the promoter in the expression vector. Alternatively, when the coding nucleic acid is cloned into pENTR/D-TOPO®, pENTR/SD/D-TOPO® (directional entry vectors), or any of the INVITROGEN's Gateway® Technology pENTR (entry) vectors, the coding nucleic acid can be transferred into the various Gateway® expression vectors (destination) for protein expression in mammalian cells, *E. coli*, insects and yeast respectively in one single recombination reaction. Some of the Gateway® destination vectors are designed for the constructions of baculovirus, adenovirus, adeno-associated virus (AAV), retrovirus, and lentiviruses, which upon infecting their respective host cells, permit heterologous expression of the prom-1 peptide in the host cells. Transferring a gene into a destination vector is accomplished in just two steps according to manufacturer's instructions. There are Gateway® expression vectors for protein expression in *E. coli*, insect cells, mammalian cells, and yeast. Following transformation and selection in *E. coli*, the expression vector is ready to be used for expression in the appropriate host.

Examples of other expression vectors and host cells are the pET vectors (NOVAGEN), pGEX vectors (Amersham Pharmacia), and pMAL vectors (New England labs. Inc.) for protein expression in *E. coli* host cells such as BL21, BL21(DE3) and AD494(DE3)pLysS, Rosetta (DE3), and Origami(DE3) (NOVAGEN); the strong CMV promoter-based pcDNA3.1 (INVITROGEN) and pCIneo vectors (PROMEGA) for expression in mammalian cell lines such as CHO, COS, HEK-293, Jurkat, and MCF-7; replication incompetent adenoviral vector vectors pAdeno X, pAd5F35, pLP-Adeno-X-CMV (CLONTECH), pAd/CMV/V5-DEST, pAd-DEST vector (INVITROGEN) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN) for lentivirus-mediated gene transfer and expression in mammalian cells; adenovirus-associated virus expression vectors such as pAAV-MCS, pAAV-IRES-hrGFP, and pAAV-RC vector (STRATAGENE) for adeno-associated virus-mediated gene transfer and expression in mammalian cells; BACpak6 baculovirus (CLONTECH) and pFastBac™ HT (INVITROGEN) for the expression in *Spodopera frugiperda* 9 (Sf9) and Sfll insect cell lines; pMT/BiP/V5-His (INVITROGEN) for the expression in *Drosophila* Schneider S2 cells; *Pichia* expression vectors pPICZα, pPICZ, pFLDα and pFLD (INVITROGEN) for expression in *Pichia pastoris* and vectors pMETα and pMET for expression in *P. methanolica*; pYES2/GS and pYD1 (INVITROGEN) vectors for expression in yeast *Saccharomyces cerevisiae*. Recent advances in the large scale expression heterologous proteins in *Chlamydomonas reinhardtii* are described by Griesbeck C. et al. 2006 *Mol. Biotechnol.* 34:213-33 and Fuhrmann M. 2004, *Methods Mol Med.* 94:191-5. Foreign heterologous coding sequences are inserted into the genome of the nucleus, chloroplast and mitochondria by homologous recombination. The chloroplast expression vector p64 carrying the versatile chloroplast selectable marker aminoglycoside adenyl transferase (aadA), which confers resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Recombinant protein expression in different host cells can be constitutive or inducible with inducers such as copper sulfate, or sugars such as galactose, methanol, methylamine, thiamine, tetracycline, or IPTG. After the protein is expressed in the host cells, the host cells are lysed to liberate the expressed protein for purification. Methods of lysing the various host cells are featured in "Sample Preparation-Tools for Protein Research" EMD Bioscience and in the Current Protocols in Protein Sciences (CPPS). A preferred purification method is affinity chromatography such as ion-metal affinity chromatograph using nickel, cobalt, or zinc affinity resins for histidine-tagged prom-1 peptide. Methods of purifying histidine-tagged recombinant proteins are described by Clontech using their Talon® cobalt resin and by Novagen in their pET system manual, 10th edition. Another preferred purification strategy is by immuno-affinity chromatography, for example, anti-Myc antibody conjugated resin can be used to affinity purify Myc-tagged prom-1 peptide. Enzymatic digestion with serine proteases such as thrombin and enterokinase cleave and release the prom-1 peptide from the histidine or Myc tag, releasing the recombinant prom-1 peptide from the affinity resin while the histidine-tags and Myc-tags are left attached to the affinity resin.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. As an example, large scale cell-free production of the integral membrane protein EmrE multidrug transporter is described by Chang G. et. al., Science 310:1950-3 (2005).

Other commercially available cell-free expression systems include the Expressway™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E.* coli-based in-vitro system; and the TNT Coupled Reticulocyte Lysate Systems (Promega) which uses a rabbit reticulocyte-based in-vitro system.

Designing Peptide Mimetics

Methods of designing peptide mimetics and screening of functional peptide mimetics are well known to those skilled in the art. One basic method of designing a molecule which mimics a known protein or peptide is first to identify the active region(s) of the known protein (for example, in the case of an antibody-antigen interaction, one identifies which region(s) of the antibody that permit binding to the antigen), and then searches for a mimetic which emulates the active region. As an example, the active region of the prom-1 peptide DRVQRQTTTVVA (SEQ. ID. NO 8) is TTTVVA (SEQ. ID. NO 12). Although the active region of the known protein is relatively small, it is anticipated that a mimetic will be smaller (e.g., in molecular weight) than the protein, and correspondingly easier and cheaper to synthesize and/or have benefits regarding stability or other advantageous pharmacokinetic aspects. Such a mimetic could be used as a convenient substitute for the protein, as an agent for interacting with the target molecule.

For example, Reineke et al. (1999, Nature Biotechnology, 17; 271-275) designed a mimic molecule which mimics a binding site of the interleukin-10 protein using a large library of short synthetic peptides, each of which corresponded to a short section of interleukin 10. The binding of each of these peptides to the target (in this case an antibody against interleukin-10) was then tested individually by an assay technique, to identify potentially relevant peptides. Phage display libraries of peptides and alanine scanning methods can be used.

Other methods for designing peptide mimetics to a particular peptide or protein include those described in European Patent EP1206494, the SuperMimic program by Andrean Goede et. al. 2006 BMC Bioinformatics, 7:11; and MIMETIC program by W. Campbell et al., 2002, Microbiology and Immunology 46:211-215. The SuperMimic program is designed to identify compounds that mimic parts of a protein, or positions in proteins that are suitable for inserting mimetics. The application provides libraries that contain peptidomimetic building blocks on the one hand and protein structures on the other. The search for promising peptidomimetic linkers for a given peptide is based on the superposition of the peptide with several conformers of the mimetic. New synthetic elements or proteins can be imported and used for searching. The MIMETIC computer program, which generates a series of peptides for interaction with a target peptide sequence, is taught by W. Campbell et. al., 2002. In depth discussion of the topic is reviewed in "Peptide Mimetic Design with the Aid of Computational Chemistry" by James R. Damewood Jr. in Reviews in Computational Chemistry Reviews in Computational Chemistry, January 2007, Volume 9 Book Series: Reviews in Computational Chemistry, Editor(s): Kenny B. Lipkowitz, Donald B. BoydPrint ISBN: 9780471186397 ISBN: 9780470125861 Published by John Wiley &Sons, Inc.; and in T. Tselios, et. al., *Amino Acids,* 14: 333-341, 1998.

Methods for preparing libraries containing diverse populations of peptides, peptoids and peptidomimetics are well known in the art and various libraries are commercially available (see, for example, Ecker and Crooke, Biotechnology 13:351-360 (1995), and Blondelle et al., Trends Anal. Chem. 14:83-92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803-861, and Gordon et al., J. Med. Chem. 37:1385-1401 (1994), each of which is incorporated herein by reference). One skilled in the art understands that a peptide can be produced in vitro directly or can be expressed from a nucleic acid, which can be produced in vitro. Methods of synthetic peptide and nucleic acid chemistry are well known in the art.

A library of peptide molecules also can be produced, for example, by constructing a cDNA expression library from mRNA collected from a tissue of interest. Methods for producing such libraries are well known in the art (see, for example, Sambrook et. al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA.

Therapeutic/Prophylactic Administration

Pharmaceutical compositions of the present invention can be applied, for example, topically to a tissue. The composition can be applied as a therapeutically effective amount in admixture with pharmaceutical carriers, in the form of topical pharmaceutical compositions. Such compositions include solutions, suspensions, lotions, gels, creams, ointments, emulsions, skin patches, etc. All of these dosage forms, along with methods for their preparation, are known in the pharmaceutical and cosmetic art. Harry's Cosmeticology (Chemical Publishing, 7th ed. 1982); Remington's Pharmaceutical Sciences (Mack Publishing Co., 18th ed. 1990). Typically, such topical formulations contain the active ingredient in a concentration range of 0.1 to 100 mg/ml, in admixture with a pharmaceutically acceptable carrier. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to a prom-1 peptide with which it is admixed, unless so desired. The preparation of a pharmacological composition that contains active ingredients dissolved or dispersed therein is well understood in the art and need not be limited based on formulation. For gene therapy using viral expression, the pharmaceutical compositions can be in the form of an adenovirus, adeno-associated virus, or lentivirus. The dosage ranges for gene therapy can be from $1\times10^6$ to $10^{14}$ particles per application. Other desirable ingredients for use in such preparations include preservatives, co-solvents, viscosity building agents, carriers, etc. The carrier itself or a component dissolved in the carrier may have palliative or therapeutic properties of its own, including moisturizing, cleansing, or anti-inflammatory/anti-itching properties. Penetration enhancers may, for example, be surface active agents; certain organic solvents, such as di-methylsulfoxide and other sulfoxides, dimethyl-acetamide and pyrrolidone; certain amides of heterocyclic amines, glycols (e.g., propylene glycol); propylene carbonate; oleic acid; alkyl amines and derivatives; various cationic, anionic, nonionic, and amphoteric surface active agents; and the like.

Topical administration of a pharmacologically effective amount can utilize transdermal delivery systems well known in the art. An example is a dermal patch. Alternatively the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The isolated prom-1 peptide expression vector, and/or gene therapy viral expression vectors can be coated on minute gold particles, and these coated particles are "shot" into biological tissues under high pressure. An example of the gene gun-based method is described for DNA based vaccination of cattle by Loehr B. I. et al., J. Virol. 2000, 74:6077-86.

In one embodiment, the pharmaceutical compositions described herein can be administered directly by injection, for example to the affected tissue, such as organ, muscle or tissue, or wound. A preferred formulation is sterile saline or Lactated Ringer's solution. Lactated Ringer's solution is a solution that is isotonic with blood and intended for intravenous administration.

In another embodiment, the peptide compositions are administered such as the agents come into contact with a subject's nervous system. In one embodiment, the active agents are administered by introduction into the cerebrospinal fluid of the subject. In certain aspects, the peptide composition is introduced into a cerebral ventricle, the lumbar area, or the cisterna magna.

In another aspect, the peptide composition is introduced locally, such as into the site of nerve or cord injury, into a site of pain or neural degeneration, or intraocularly to contact neuroretinal cells. In one embodiment, the peptide composition described herein is administered to the subject in the period from the time of, for example, an injury to the CNS up to about 100 hours after the injury has occurred, for example within 24, 12, or 6 hours from the time of injury.

In another embodiment of the invention, the peptide composition is administered into a subject intrathecally. As used herein, the term "intrathecal administration" is intended to include delivering a peptide composition directly into the cerebrospinal fluid of a subject, by techniques including lateral cerebroventricular injection through a burrhole or cisternal or lumbar puncture or the like (described in Lazorthes et al., 1991, and Ommaya A. K., 1984, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of an active compound to any of the above mentioned sites can be achieved by direct injection of the active compound formulation or by the use of infusion pumps. Implantable or external pumps and catheter may be used.

An additional means of administration to intracranial tissue involves application of compounds of the invention to the olfactory epithelium, with subsequent transmission to the olfactory bulb and transport to more proximal portions of the brain. Such administration can be by nebulized or aerosolized preparations. In a further embodiment, ophthalmic peptide compositions are used to prevent or reduce damage to retinal and optic nerve head tissues, as well as to enhance functional recovery after damage to ocular tissues. Ophthalmic conditions that may be treated include, but are not limited to, retinopathies (including diabetic retinopathy and retrolental fibroplasia), macular degeneration, ocular ischemia, and glaucoma. Other conditions to be treated with the methods described herein include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic compositions may also be used as an adjunct to ophthalmic surgery, such as by vitreal or subconjunctival injection following ophthalmic surgery. The peptide compositions may be used for acute treatment of temporary conditions, or may be administered chronically, especially in the case of degenerative disease. The ophthalmic peptide compositions may also be used prophylactically, especially prior to ocular surgery or noninvasive ophthalmic procedures or other types of surgery.

In one embodiment, the active compound is administered to a subject for an extended period of time to produce optimum axonal outgrowth. Sustained contact with the peptide composition can be achieved by, for example, repeated administration of the peptide composition over a period of time, such as one week, several weeks, one month or longer. More preferably, the pharmaceutically acceptable formulation used to administer the active compound provides sustained delivery, such as "slow release" of the active compound to a subject. For example, the formulation may deliver the active peptide composition for at least one, two, three, or four weeks after the pharmaceutically acceptable formulation is administered to the subject. Preferably, a subject to be treated in accordance with the methods described herein is treated with the active peptide composition for at least 30 days (either by repeated administration or by use of a sustained delivery system, or both).

As used herein, the term "sustained delivery" is intended to include continual delivery of the active peptide composition in vivo over a period of time following administration, preferably at least several days, a week, several weeks, one month or longer. Sustained delivery of the active compound can be demonstrated by, for example, the continued therapeutic effect of the peptide composition over time (such as sustained delivery of the agents can be demonstrated by continued axonal growth in CNS neurons in a subject). Alternatively, sustained delivery of the peptide composition may be demonstrated by detecting the presence of the peptide composition in vivo over time.

Preferred approaches for sustained delivery include use of a polymeric capsule, a minipump to deliver the formulation, a biodegradable implant, or implanted transgenic autologous cells (as described in U.S. Pat. No. 6,214,622). Implantable infusion pump systems (such as Infusaid; see such as Zierski, J. et al, 1988; Kanoff, R. B., 1994) and osmotic pumps (sold by Alza Corporation) are available in the art. Another mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

In addition to topical therapy it is contemplated that the pharmaceutical compositions described herein can also be administered systemically in a pharmaceutical formulation. Systemic routes include but are not limited to oral, parenteral, nasal inhalation, intratracheal, intrathecal, intracranial, and intrarectal. The pharmaceutical formulation is preferably a sterile saline or lactated Ringer's solution. For therapeutic applications, the preparations described herein are administered to a mammal, preferably a human, in a pharmaceutically acceptable dosage form, including those that may be administered to a human intravenously as a bolus or by continuous infusion over a period of time, by intramuscular, intraperitoneal, intracerebrospinal, subcutaneous, intra-arterial, intrasynovial, intrathecal, oral, or inhalation routes. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required. Vector DNA and/or virus can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et. al. Gene Ther. 1999, 6:1438-47). Other techniques in formulating expression vectors and virus as therapeutics are found in "DNA-Pharmaceuticals: Formulation and Delivery in Gene Therapy, DNA Vaccination and Immunotherapy" by Martin Schleef (Editor) December 2005, Wiley Publisher, and "Plasmids for Therapy and Vaccination" by Martin Schleef (Editor) May 2001, are incorporated herein as reference. In one embodiment, the dosage for viral vectors is $1 \times 10^6$ to $10^{14}$ viral vector particles per application per patient.

The compositions can be formulated as a sustained release composition. For example, sustained-release means or delivery devices are known in the art and include, but are not limited to, sustained-release matrices such as biodegradable matrices or semi-permeable polymer matrices in the form of shaped articles, e.g., films, or microcapsules that comprise prom-1 peptides, expression vectors and/or viral vectors.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly(2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release compositions also include liposomally entrapped prom-1 peptides, expression vectors, and nucleic acid constructs. Such liposomes can be prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446).

Methods for preparing liposomes and microspheres for administration to a patient are known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

Preferred micro particles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, osmotic mini pumps can be used to provide controlled sustained delivery of the pharmaceutical compositions described herein, through cannulae to the site of interest, e.g., directly into a tissue at the site of needing angiogenesis. The pump can be surgically implanted; for example, continuous administration of endostatin, an anti-angiogenesis agent, by intraperitoneally implanted osmotic pump is described in Cancer Res. 2001 Oct. 15; 61(20):7669-74. Therapeutic amounts of prom-1 peptides can also be continually administered by an external pump attached to an intravenous needle.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

For enteral administration, a composition can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet can be made by compression or molding, optionally with one or more accessory ingredients. Compressed tablets can be prepared by compressing in a suitable machine the active compound in a free-flowing form, e.g., a powder or granules, optionally mixed with accessory ingredients, e.g., binders, lubricants, inert diluents, surface active or dispersing agents. Molded tablets can be made by molding in a suitable machine, a mixture of the powdered active compound with any suitable carrier.

A syrup or suspension can be made by adding the active compound to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration can be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propane-sulfonate), Big-CHAPS(N,N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

Formulations for rectal administration can be presented as a suppository with a conventional carrier, e.g., cocoa butter or Witepsol S55 (trademark of Dynamite Nobel Chemical, Germany), for a suppository base.

The route of administration, dosage form, and the effective amount vary according to the potency of the prom-1 peptides, expression vectors and viral vectors, their physicochemical characteristics, and according to the treatment location. The selection of proper dosage is well within the skill of an ordinarily skilled physician. Topical formulations can be administered up to four-times a day.

In one embodiment, dosage forms include pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of compositions include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nanocapsules, liposomes, plasters, inhalation forms, nose sprays, sublingual tablets, and sustained release preparations. For examples of sustained release compositions, see U.S. Pat. No. 3,773,919, EP 58,481A, U.S. Pat. No. 3,887,699, EP 158, 277A, Canadian Patent No. 1176565, U. Sidman et al., Biopolymers 22:547 (1983) and R. Langer et al., Chem. Tech. 12:98 (1982). The prom-1 peptides will usually be formulated in such vehicles at a concentration of about 0.1 mg/ml to 100 mg/ml and the viral vector should be in the range of $1 \times 10^6$ to $10^{14}$ viral vector particles per application per patient.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the pharmaceutical formulation to be used for therapeutic administration is sterile. Sterility is readily accomplished by filtration through sterile filtration membranes (e.g., 0.2 micron membranes). The prom-1 peptide compositions can be stored in lyophilized form or as an aqueous solution if it is highly stable to thermal and oxidative denaturation. The pH of the prom-1 peptide composition preparations typically can be about from 6 to 8.

For therapeutic applications, the appropriate dosage of compositions will depend upon the type of tissue needing angiogenesis, neuroprotection or other beneficial effect of the prom-1 peptide, the associated medical conditions to be treated, the severity and course of the medical conditions, whether the compositions are administered for preventative or therapeutic purposes, previous therapy, the patient's clinical history and response to the compositions and the discretion of the attending physician. In addition, in vitro or in vivo assays can optionally be employed to help identify optimal dosage ranges. The precise dose to be employed will also depend on the route of administration, and the seriousness of the condition being treated and should be decided according to the judgment of the practitioner and each subject's circumstances in view of, e.g., published clinical studies. Suitable effective dosage amounts for topical administration of the peptide compositions described herein range from about 10 micrograms to about 5 grams applied or administered about every 4 hours, although they are typically about 500 mg or less per every 4 hours. In one embodiment the effective dosage for topical administration is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, or about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered.

For systemic administration, the dosage ranges are typically from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

The compositions comprising prom-1 peptides, expression vectors and/or viral vectors are suitably administered to the patient at one time or over a series of treatments. For purposes herein, a "therapeutically effective amount" of a composition comprising prom-1 peptides, prom-1 peptide variants, fusion protein comprising a prom-1 peptide, expression vector and/or viral vector is an amount that is effective to either prevent, reduce the likelihood, lessen the worsening of, alleviate, or cure one or more symptoms or indicia of the treated condition.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, a peptide as described herein can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to a prom-1 peptide permits the agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Gene Therapy Using Nucleic Acids Coding for Peptides

The principles of gene therapy are disclosed by Oldham, R. K. (In: Principles of Biotherapy, Raven Press, N.Y., 1987), and similar texts. Disclosures of the methods and uses for gene therapy are provided by Boggs, S. S. (Int. J. Cell Clon. 8:80-96 (1990)); Karson, E. M. (Biol. Reprod. 42:39-49 (1990)); Ledley, F. D., In: Biotechnology, A Comprehensive Treatise, volume 7B, Gene Technology, VCH Publishers, Inc. NY, pp 399-458 (1989)), all of which references are incorporated herein by reference.

In one embodiment, the peptides can be administered to a patient by any one of several gene therapy techniques known to those of skill in the art. In general, gene therapy can be accomplished by either direct transformation of target cells within the mammalian subject (in vivo gene therapy) or transformation of cells in vitro and subsequent implantation of the transformed cells into the mammalian subject (ex vivo gene therapy).

In one embodiment, DNA encoding the peptides can be introduced into the somatic cells of an animal (particularly mammals including humans) in order to provide a treatment of a disease or condition that responds to the peptide composition. Most preferably, viral or retroviral vectors are employed for this purpose.

Retroviral vectors are a common mode of delivery and in this context are often retroviruses from which viral genes have been removed or altered so that viral replication does not occur in cells infected with the vector. Viral replication functions are provided by the use of retrovirus "packaging" cells that produce the viral proteins required for nucleic acid packaging but that do not produce infectious virus.

Introduction of the retroviral vector DNA into packaging cells results in production of virions that carry vector RNA and can infect target cells, but such that no further virus spread occurs after infection. To distinguish this process from a natural virus infection where the virus continues to replicate and spread, the term transduction rather than infection is often used.

In one embodiment, the invention provides a recombinant lentivirus for the delivery and expression of a peptide in either dividing or non-dividing mammalian cells. The HIV-1 based lentivirus can effectively transduce a broader host range than the Moloney Leukemia Virus (MoMLV)-based retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

Examples of use of lentiviral vectors for gene therapy for e.g., inherited disorders and various types of cancer, are described in the following references and are hereby incorporated by reference in their entirety (Klein, C. and Baum, C. (2004). Hematol. J., 5, 103-111; Zufferey, R. et al., (1997). Nat. Biotechnol., 15, 871-875; Morizono, K. et. al. (2005). Nat. Med., 11, 346-352; Di Domenico, C. et al. (2005), Gene therapy for amucopolysaccharidosis type I murine model with lentiviral-IDUA vector. Hum. Gene Ther., 16, 81-90; Kim, E. Y., Hong, Y. B., Lai, Z., Kim, H. J., Cho, Y.-H., Brady, R. O. and Jung, S.-C. (2004). Biochem. Biophys. Res. Comm., 318, 381-390).

Non-retroviral vectors also have been used in genetic therapy. One such alternative is the adenovirus (Rosenfeld, M. A., et al., Cell 68:143155 (1992); Jaffe, H. A. et al., Nature Genetics 1:372-378 (1992); Lemarchand, P. et al., Proc. Natl. Acad. Sci. USA 89:6482-6486 (1992)). Major advantages of adenovirus vectors are their potential to carry large segments of DNA (36 Kb genome), a very high titer ($10^{11}$ particles/ml), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., Cell 63:143-155 (1992)). Similarly, herpes viruses may also prove valuable for human gene therapy (Wolfe, J. H. et al., Nature Genetics 1:379-384 (1992)). Of course, any other suitable viral vector can be used for the genetic therapy for the delivery of prom-1 peptides as described herein.

The viron used for gene therapy can be any viron known in the art including but not limited to those derived from adenovirus, adeno-associated virus (AAV), retrovirus, and lentivirus. Recombinant viruses provide a versatile system for gene expression studies and therapeutic applications.

The recombinant AAV virions described above, including the DNA of interest, can be produced using standard methodology, known to those of skill in the art. The methods generally involve the steps of (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques.

A simplified system for generating recombinant adenoviruses is presented by He TC. et. al. Proc. Natl. Acad. Sci. USA 95:2509-2514, 1998. The gene of interest is first cloned into a shuttle vector, e.g., pAdTrack-CMV. The resultant plasmid is linearized by digesting with restriction endonuclease Pme I, and subsequently cotransformed into E. coli. BJ5183 cells with an adenoviral backbone plasmid, e.g., pAdEasy-1 of Stratagene's ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

In one embodiment, the invention provides a recombinant adeno-associated virus (rAAV) vector for the expression of a peptide, or e.g., a fusion protein including a peptide as described herein. Using rAAV vectors, genes can be delivered into a wide range of host cells including many different human and non-human cell lines or tissues. Because AAV is non-pathogenic and does not elicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml can be obtained with further concentration. The transgene is integrated into the host genome, so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, for example, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying a DNA coding sequence for a peptide, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Although local administration will most likely be preferred, a prom-1 peptide used in the methods described herein can be delivered systemically via in vivo gene therapy. Systemic treatment involves transfecting target cells with the DNA of interest, i.e., DNA encoding a prom-1 peptide, expressing the coded peptide/protein in that cell, and the capability of the transformed cell to subsequently secrete the manufactured peptide/protein into the blood.

A variety of methods have been developed to accomplish in vivo transformation including mechanical means (e.g., direct injection of nucleic acid into target cells or particle bombardment), recombinant viruses, liposomes, and receptor-mediated endocytosis (RME) (for reviews, see Chang et al. 1994 Gastroenterol. 106:1076-84; Morsy et al. 1993 JAMA 270: 2338-45; and Ledley 1992 J. Pediatr. Gastroenterol. Nutr. 14:328-37).

Another gene transfer method for use in humans is the transfer of plasmid DNA in liposomes directly to human cells in situ (Nabel, E. G., et al., Science 249:1285-1288 (1990)). Plasmid DNA should be easy to certify for use in human gene therapy because, unlike retroviral vectors, it can be purified to homogeneity. In addition to liposome-mediated DNA transfer, several other physical DNA transfer methods, such as those targeting the DNA to receptors on cells by conjugating the plasmid DNA to proteins, have shown promise in human gene therapy (Wu, G. Y., et al., J. Biol. Chem., 266:14338-14342 (1991); Curiel, D. T., et al., Proc. Natl. Acad. Sci. USA, 88:8850-8854 (1991)).

Some embodiments of the present invention can be defined as any of the following numbered paragraphs:

1. An isolated prom-1 peptide derived from a prominin-1, the peptide having VEGF binding activity.

2. An isolated prom-1 peptide of a prominin-1, the peptide having pro-angiogenic activity.

3. An isolated prom-1 peptide of a prominin-1, the peptide promotes wound healing. 4. An isolated prom-1 peptide derived from an extracellular domain of a prominin-1, the peptide having pro-angiogenic activity.

5. The isolated prom-1 peptide of any of paragraphs 1-4, wherein the prominin-1 is human prominin-1.

6. The isolated prom-1 peptide of either of paragraph 4 or 5, wherein the extracellular domain is one of SEQ. ID. No. 1, 2, or 3.

7. The isolated prom-1 peptide of any one of paragraphs 1-6, wherein the peptide comprises at least 6 consecutive amino acid residues from SEQ ID NOs: 1, 2, or 3, and wherein the peptide does not include a full-length prominin-1.

8. An isolated peptide that is a conservative amino acid substitution variant of a peptide of any one of paragraphs 1-7.

9. A peptide that is at least 90% identical to a peptide of any one of paragraphs 1-8, wherein the peptide has pro-angiogenic activity.

10. An isolated peptide fragment of a prominin-1, the peptide having pro-angiogenic activity, wherein the peptide consists essentially of a peptide selected from the group consisting of: LCGNSFSGGQPS (SEQ. ID. No. 4) ; PNIIPVLDEIKS (SEQ. ID. No. 5); LCGVCGYDRHAT (SEQ. ID. No. 6); ITNNTSSVIIEE (SEQ. ID. No. 7); DRVQRQTTTVVA (SEQ. ID. No. 8); and CSFAYDLEAKANSLPPGNLRN (SEQ. ID. No.9), or a conservative amino acid substitution variant thereof that substantially retains pro-angiogenic activity.

11. The isolated peptide of any one of paragraphs 1-10, wherein the peptide enhances VEGF binding to endothelial cells.

12. The isolated peptide of any one of paragraphs 1-11, wherein the peptide enhances cell proliferation.

13. The isolated peptide of any one of paragraphs 1-12, wherein the peptide enhances proliferation of endothelial cells.

14. The isolated peptide of any of paragraphs 1-13, wherein the peptide enhances angiogenesis in the presence of a pro-angiogenic factor.

15. The isolated peptide of any of paragraphs 1-14, wherein the peptide enhances cell migration in the presence of a pro-angiogenic factor.

16. The isolated prom-1 peptide of any one of paragraphs 1-15, wherein the prom-1 peptide is comprised by a cyclic peptide.

17. The isolated peptide of any of paragraphs 1-15, wherein the peptide is conjugated to a polymer.

18. A fusion protein comprising a peptide of any one of paragraphs 1-17, fused to a heterologous peptide or polypeptide, wherein the fusion protein is not a full-length prominin-1.

19. A composition comprising a pharmaceutically acceptable carrier and an isolated prom-1 peptide of any one of paragraphs 1-18.

20. A method of promoting cell proliferation in a tissue in need thereof, the method comprising contacting the tissue with a composition of paragraph 19.

21. A method of promoting angiogenesis in a tissue in need thereof, the method comprising contacting the tissue with a composition of paragraph 19.

22. The method of paragraph 20 or 21, wherein the method is applied in the context of promoting wound healing, neuronal growth, protection or repair, tissue repair, fertility promotion, cardiac hypertrophy, treatment of erectile dysfunction, modulation of blood pressure, revascularization after disease or trauma, tissue grafts, or tissue engineered constructs.

23. A method of promoting wound healing, the method comprising contacting the wound with an isolated prom-1 peptide, cyclic peptide, or fusion protein of any one of paragraphs 1-19, whereby wound healing is enhanced relative to wound healing in the absence of the peptide or fusion protein.

24. A method of promoting neuroprotection or neural regeneration comprising contacting a neuronal cell with an isolated prom-1 peptide of a prominin-1.

25. The method of paragraph 22 wherein the prom-1 peptide of a prominin-1 comprises sequence found in an extracellular domain of the prominin-1.

26. The method of paragraph 22 or 23 wherein the prominin-1 is human prominin-1.

27. The method of paragraph 23 or paragraph 24, wherein the extracellular domain is one of SEQ. ID. No. 1, 2, or 3.

28. The method of any one of paragraphs 22-25, wherein the prom-1 peptide comprises at least 6 consecutive amino acid residues of the full-length prom-1, and wherein the peptide does not include a full-length prominin-1.

29. The method of any one of paragraphs 22-26 wherein the prom-1 peptide comprises a conservative amino acid substitution relative to the corresponding wild-type human prominin-1 sequence.

30. The method of any one of paragraphs 22-27 wherein the prom-1 peptide is a conservative amino acid substitution variant of a peptide of SEQ ID NO: 8.

31. The method of any one of paragraphs 22-28 wherein the prom-1 peptide is comprised by a cyclic peptide.

32. The method of any one of paragraphs 22-29 wherein the prom-1 peptide is comprised by a heterologous fusion polypeptide.

33. The method of any one of paragraphs 22-30 wherein the prom-1 peptide is conjugated to a polymer.

34. The method of any one of paragraphs 22-31 wherein the prom-1 peptide consists essentially of a peptide of SEQ ID NO: 8.

35. The method of any one of paragraphs 22-32 wherein the prom-1 peptide consists of SEQ ID NO: 8.

36. The method of any one of paragraphs 22-33 wherein the contacting comprises administering a pharmaceutical composition comprising the prom-1 peptide and a pharmaceutically acceptable carrier to an individual in need of neuroprotection.

37. The method of any one of paragraphs 22-34 wherein the contacting prevents or delays neuronal cell death relative to neuronal cell death occurring in the absence of the contacting.

38. The method of any one of paragraphs 22-35 wherein the contacting promotes nerve regeneration.

39. A cyclic peptide of prominin-1 comprising the formula of CX(DRVQRQTTTVVA)ZC (SEQ ID NO: 37) or ACX(DRVQRQTTTVVA)ZC (SEQ ID NO: 38), wherein X or Z are each independently 0-20 amino acids.

40. The cyclic peptide of paragraph 39 comprising a sequence selected from the group consisting of: ACGG(DRVQRQTTTVVA)GGC (SEQ ID NO: 15), ACGG(DRVQRQTTTVVA)GGGGGGC (SEQ ID NO: 16), and CGGGGGG(DRVQRQTTTVVA)GGCA (SEQ ID NO: 17).

41. The cyclic peptide of paragraph 37 or 38, wherein the peptide enhances VEGF binding to endothelial cells.

42. The cyclic peptide of any one of paragraphs 37-39, wherein the peptide enhances cell proliferation.

43. The cyclic peptide of any one of paragraphs 37-40, wherein the peptide enhances proliferation of endothelial cells.

44. The cyclic peptide of any one of paragraphs 37-41, wherein the peptide enhances angiogenesis in the presence of a pro-angiogenic factor.

45. The cyclic peptide of any one of paragraphs 37-42, wherein the peptide enhances cell migration in the presence of a pro-angiogenic factor.

46. The cyclic peptide of any one of paragraphs 37-43, wherein the peptide promotes wound healing.

47. The cyclic peptide of any one of paragraphs 37-43 wherein the prominin-1 is human prominin-1.

48. An isolated prom-1 peptide of any one of paragraphs 1-19 or 40-47, wherein said peptide stimulates neuronal growth.

49. An isolated prom-1 peptide of a prominin-1, said peptide having neuronal growth stimulatory activity.

50. A method for stimulating neuron growth, the method comprising contacting a neuron with a peptide of any one of paragraphs 1-19 or 40-49.

This invention is further illustrated by the following examples which should not be construed as limiting.

EXAMPLES

Example 1

Seven 12-Mer Peptides Derived from Prominin-1 Sequence Bind VEGF

Minimum epitope assignment was based on immunostaining of ABIMED spot peptide arrays prepared at the MIT Biopolymers Facility (FIG. 2). Each spot comprised a 12-mer contiguous peptide, and depending on the number of residues in the antigen of interest, 3-residue offset was used to cover the entire antigen sequence. For 3-residue offset, spot 1 contains sequence 1-12, spot 2 contains sequence 3-15, spot 3 contains sequence 6-18, etc. The Cellulose-bound peptide membrane was preincubated with T-TBS blocking buffer (TBS, pH 8.0/0.05% Tween 20 in the presence of blocking reagent; Roche Diagnostics chemiluminescence detection kit 1500694). Subsequently, the peptide array was incubated with hVEGF at a final concentration of 1.0 μg/ml for 2 h in T-TBS blocking buffer. After washing three times for 10 min with T-TBS the anti-hVEGF antibody (Quantum Biotechnologies, Montreal), was added to a final concentration of 11 g/ml in T-TBS blocking buffer for 1 h followed by washing three times for 10 min with T-TBS. Finally, the arrays were incubated with a second anti-mouse IgG peroxidase-labeled antibody (catalog no. A5906, Sigma), which was applied at a concentration of 11 g/ml in T-TBS blocking buffer for 1 h, followed by washing three times for 10 min with T-TBS. Analysis of peptide-bound VEGF-antibody complexes was done by using a chemiluminescence substrate. Binding of the detection antibody to the peptides was excluded by control incubations with anti-mouse IgG peroxidase-labeled antibody alone (data not shown). The seven highly reacted peptides were commercially synthesized (Genescript Co., NJ) (Table 1) and confirmed for binding to VEGF-A by ELISA and dot blot (data not shown).

Example 2

Figure 3A:
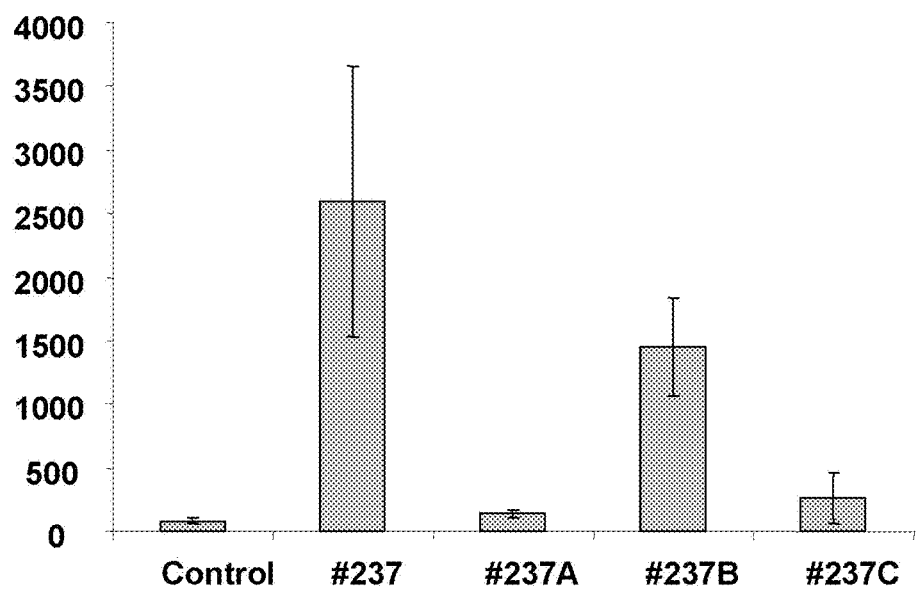
FIG. 3A shows that peptide #237 increased VEGF binding to endothelial cells.
Figure 3B:
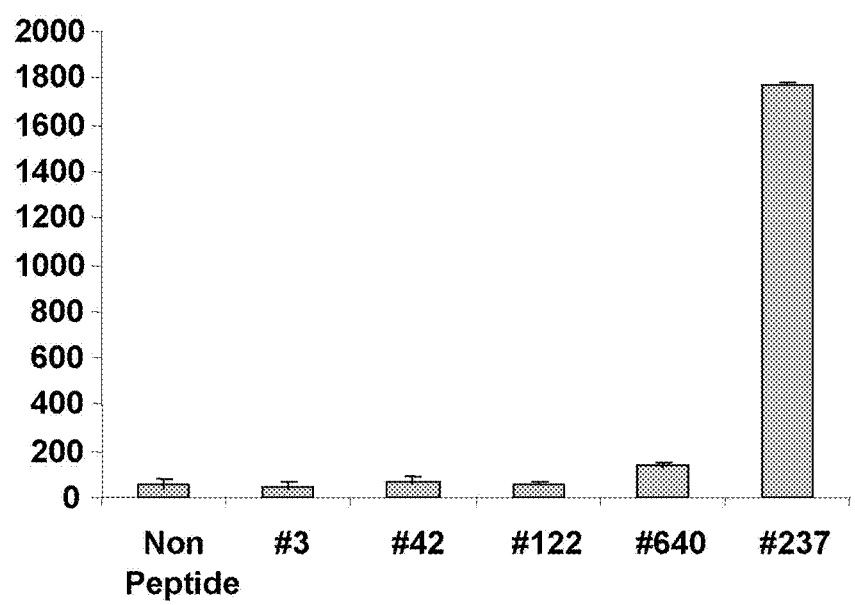
FIG. 3B shows that peptide #237 increased VEGF binding to melanoma cells.
Figure 4:
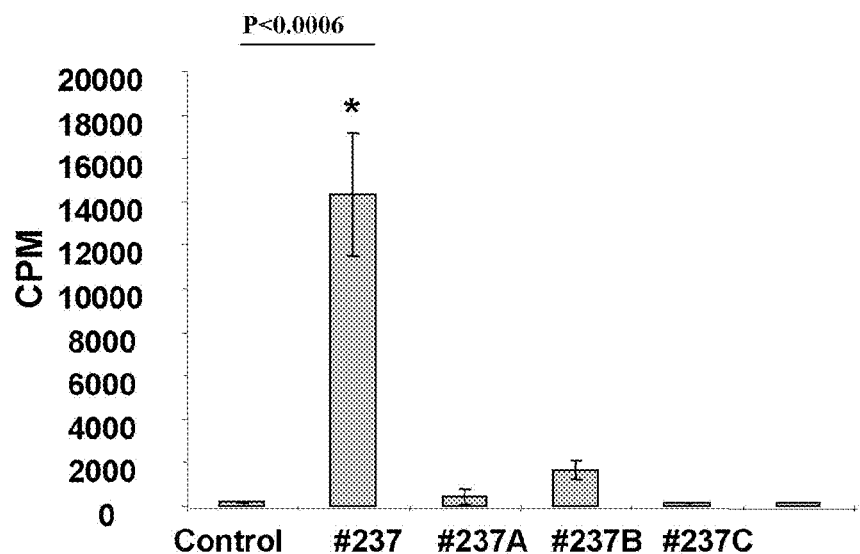
FIG. 4: Enhanced VEGF binding is abolished when #237 fragments, #237A and #237C were used. Prom-1 peptide #237B partially increases the VEGF binding as compared to the control.
Figure 4:
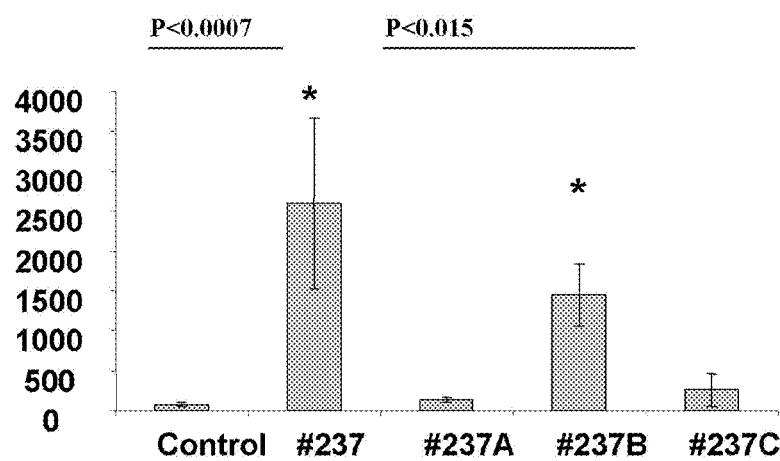

Peptide 237 Derived from the Extracellular Domain of Prominin Dramatically Increases VEGF Binding to Endothelial and B16-F10 Melanoma Cells In order to characterize the effect of the peptides on VEGF binding to endothelial and melanoma cells, the cells were incubated with various peptides (720 μg/ml) in the presence of h25-VEGF (12 ng/ml) (FIG. 3). Peptide #237 increased VEGF binding to endothelial as well to melanoma cells. 10000 cells were incubated in binding buffer containing 20 mM Hepes, 0.1% BSA and $I^{125}$-VEGF (12 ng/ml) for 3 h on ice. Following 3 washings, the radioactive levels were determined by gamma counter. An increase of more than 25 times in $I^{125}$-VEGF binding was observed when peptide #237 was added to both kinds of cells. All other peptides had no effect on VEGF binding.

Example 3

Determination of the Essential Amino Acids for VEGF Binding in Peptide #237

To characterize which are the essential amino acids within the #237 peptide that are crucial to accelerate VEGF binding to the cells, three shorter peptides were designed as presented at Table 2. The cells were treated with the smaller peptides in the same way as described in FIG. 3. 10000 cells were incubated in binding buffer containing 20 mM Hepes, 0.1% BSA, $I^{125}$-VEGF (12 ng/ml) and 100 μg/ml of each peptide, for 3 h on ice. Following 3 washings with binding buffer, the radioactive levels were determined using a gamma counter. It is concluded that the first 6-mer peptide (#237A) is not crucial to enhance VEGF binding to cells whereas the second 6-mer (#237B) shows a partial increase in VEGF binding to endothelial cells and better binding to melanoma cells. In addition, the amino acids valine and alanine, located in the C terminus of the peptide, were found to be crucial in the VEGF binding process. When these two amino acids were removed from the original peptide as presented by #237C, the VEGF binding was essentially eliminated.

TABLE 2

| #237 peptide fragments | | |
|---|---|---|
| #237 | DRVQRQTTTVVA | SEQ ID NO: 8 |
| A | DRVQRQ | SEQ ID NO: 13 |
| B | TTTVVA | SEQ ID NO: 12 |
| C | VQRQTTTV | SEQ ID NO: 14 |

Figure 9:
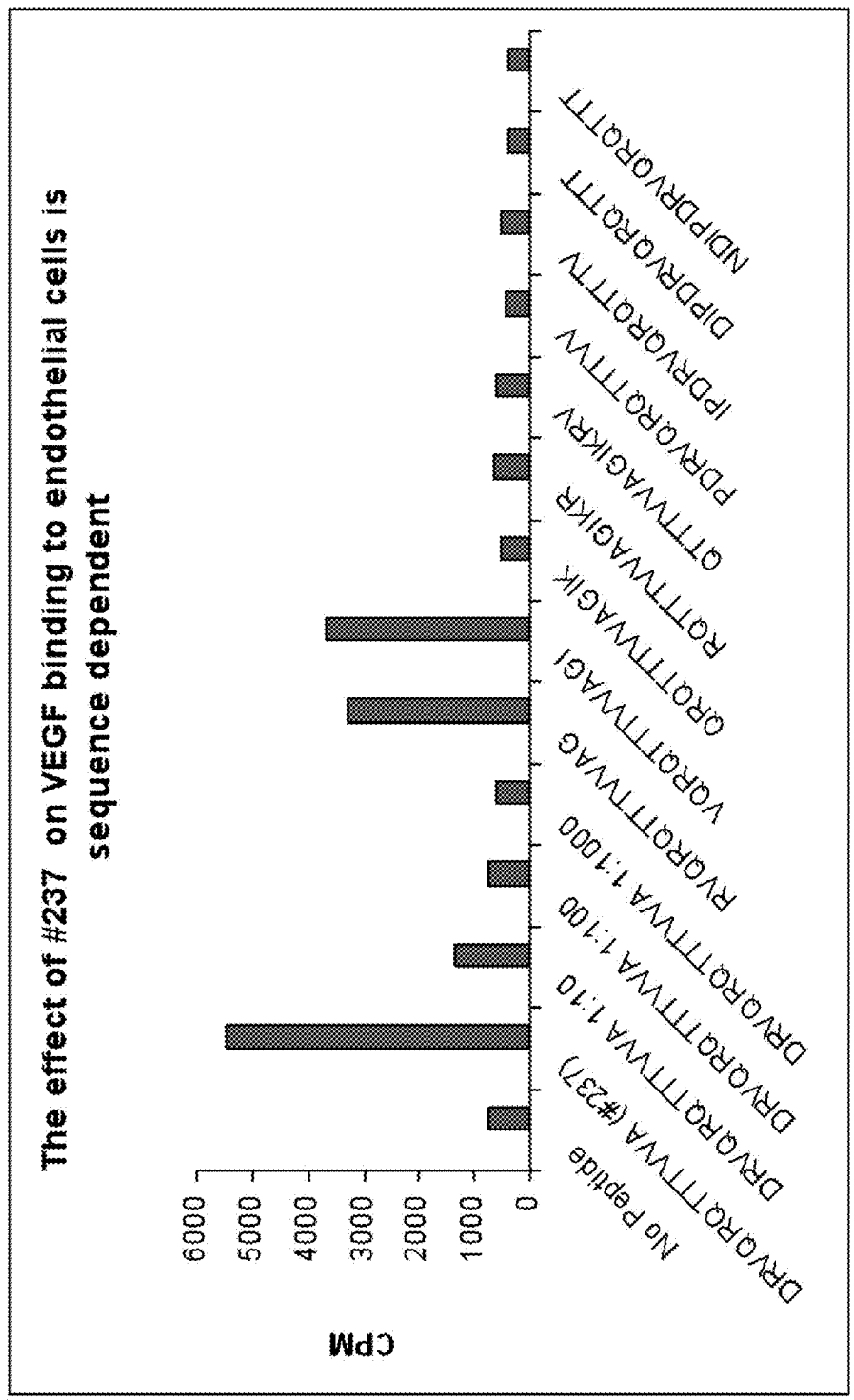
FIG. 9 is a bar graph showing the results of experiments indicating that the effect of peptides derived from peptide #237 on VEGF binding to endothelial cells is sequence dependent.

In addition, a series of peptides derived from peptide #237 were designed to test the sequence dependency of the peptide to enhance VEGF binding to endothelial cells. The peptides were synthesized by sequentially deleting an amino acid from either the N-terminus or C-terminus and adding to the opposite terminus the next amino acid in the prominin-1 sequence. Essentially, the peptide sequence is shifted in either direction by one amino acid in the promonin-1 sequence at a time. Each of these peptides were tested for VEGF binding to endothelial cells and compared to peptide #237 at varying dilutions. The results are indicated herein in FIG. 9.

Example 4

Figure 5A:
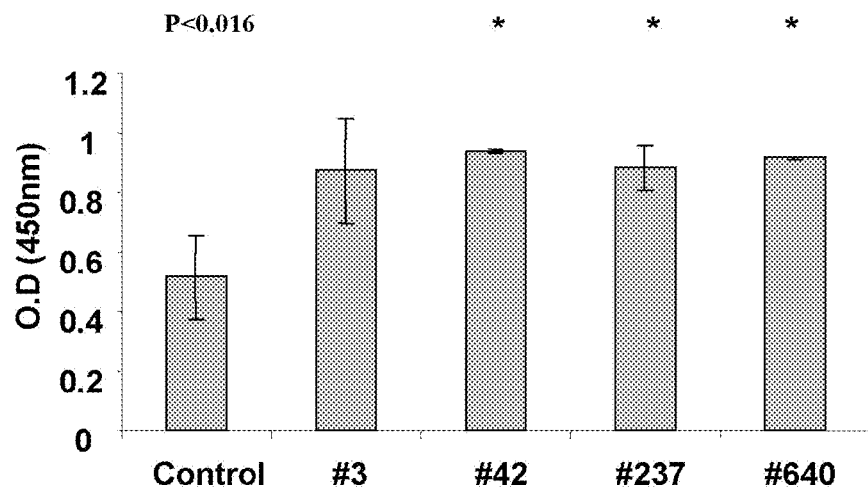
FIG. 5A shows that prominin-1 extracellular fragments increase human umbilical vein endothelial cell (HUVEC) proliferation.
Figure 5B:
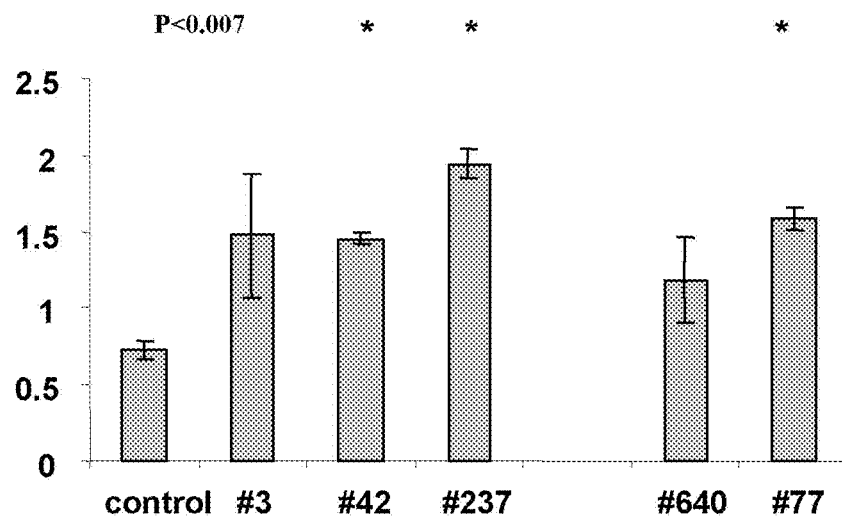
FIG. 5B shows that prominin-1 extracellular fragments increase human B16-F10 melanoma cell proliferation.

Extracellular Fragments of Prominin-1 Affect Endothelial and Melanoma Cell Proliferation Cell proliferation was assessed using an assay based on the cleavage of the tetrazolium salt WST-1 to formazan by cellular mitochondrial dehydrogenases. Aliquot of 50,000 microvessel endothelial cells (FIG. 5A) or F10-B16 melanoma cells (FIG. 5B) were added to each well of a 96-well plate in EGM medium containing 10% fetal bovine serum. After cells had attached to the 96-well tray, the cells were washed, and high serum medium was replaced with starvation medium overnight. All wells were rinsed with phosphate-buffered saline. Negative control wells received starvation medium, and positive control wells received full medium. The cells were treated with the different peptides (100 ug/ml) to determine their effect on cell proliferation. Cells were allowed to incubate for 24 h in the presence of the respective peptide. At this time, the WST-1 reagent, was applied for 4 h to measure cell proliferation. The plates were read on OD=450 nm, and data were presented as a percentage of negative control proliferation, with $p<0.05$ being significant. Expansion in the number of viable cells results in an increase in the overall activity of the mitochondrial dehydrogenases in the wells. As shown in FIG. 5, human umbilical vein endothelial cell (HU- VEC) and B16-F10 melanoma cell proliferation were significantly increased by incubation with cellular fragments of Prominin-1 ($p<0.05$).

Example 5

Figure 6:
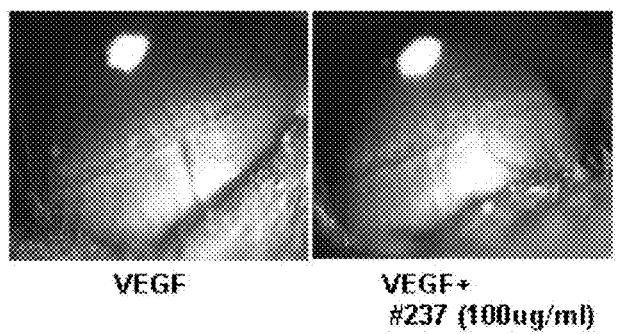
FIG. 6 shows the effect of Hydron pellets containing VEGF (160 ng/pellet) or VEGF+#237 (1.3 ug/pellet) implanted into mouse corneas. Vigorous vessel in-growth from the limbus at 5 days was recorded as a positive response.
Figure 6:
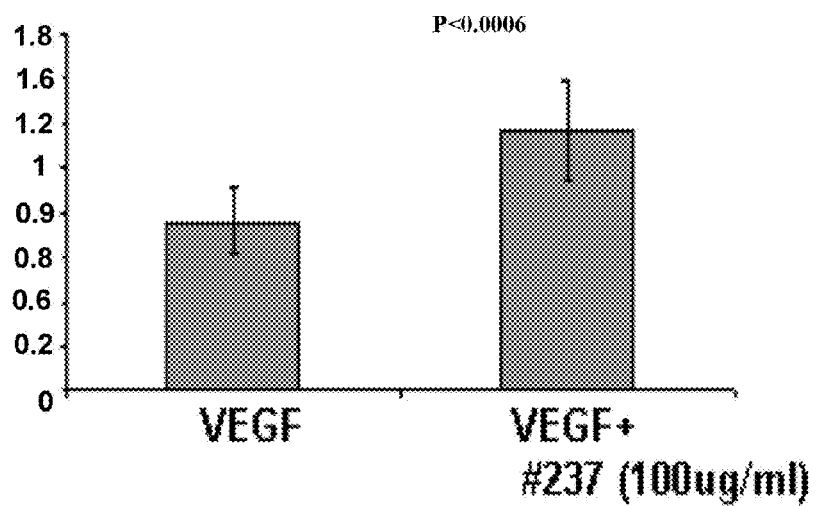

Prominin Fragment (#237) Dramatically Increases Angiogenesis In Vivo when Added to the VEGF Pellet During Corneal Micropocket Assay In order to evaluate the modulating effect of peptide #237 on the angiogenesis process, a corneal micropocket assay was performed. Two kinds of pellets were created, both containing 160 ng carrier-free recombinant human VEGF 165 (R&D Systems, Minneapolis, Minn.), one of which contains 1.3 ug of #237 peptide. The pellets were implanted into micropockets created in the cornea of two groups of anesthetized mice (n=4). Through the use of standardized slow-release pellets, a predictable angiogenic response is generated over the course of 5 days and then quantified. The area of neovascularization was calculated as vessel area, which is calculated as the product of vessel length measured from the limbus and clock hours around the cornea, using the following equation: vessel area (mm$^2$)=[clock hours×vessel length (mm)×0.2 mm]. An increase of 53% was observed in the vessel density in the treated eyes (pellet with peptide #237) versus the control (pellet without peptide #237) (FIG. 6). The in vivo experiment confirms that the peptide stimulates cell proliferation, and is therefore a good candidate to induce angiogenesis.

Example 6

Figure 7:
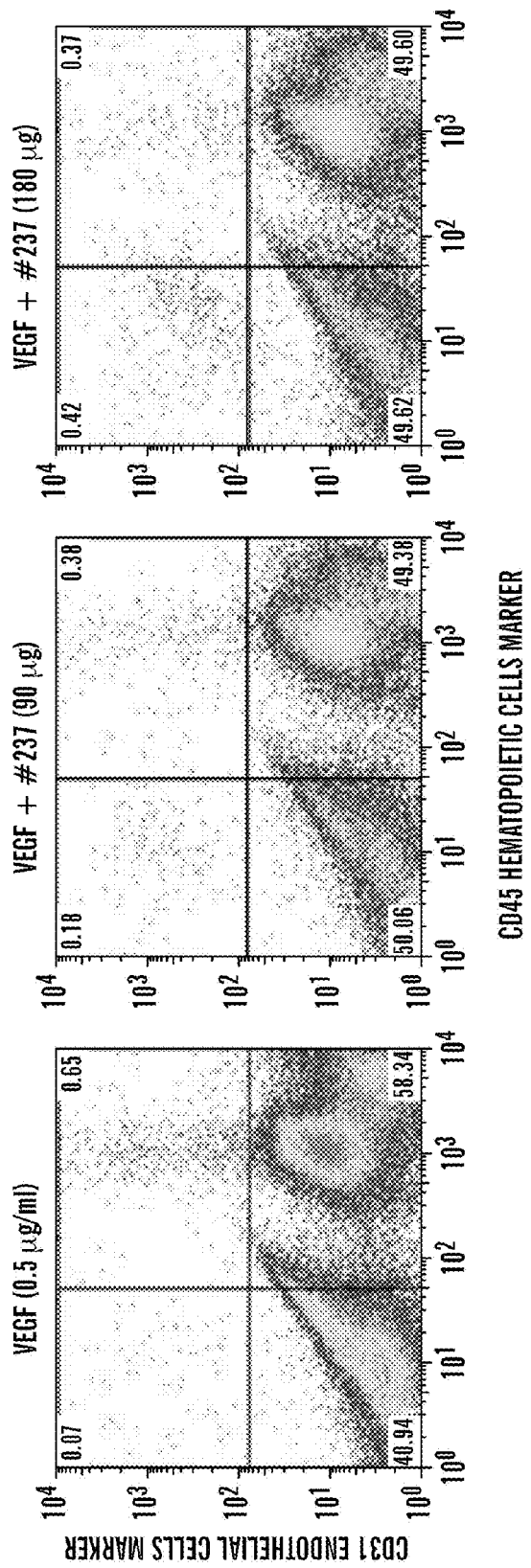
FIG. 7 shows that the Prom-1 peptide #237 dramatically increases endothelial cell migration. Shown are data from the FACS analyses of matrigel liberated cells from two groups of treated mice.

Prominin Fragment (#237) Increases Endothelial Cell Migration In Vivo when Combined with VEGF as Tested in the Matrigel Assay Two groups of 8-week-old C57bl mice were anaesthetized and injected subcutaneously with either 0.5 ml ice-cold Matrigel supplemented with 500 ng VEGF (0.5 µg/ml), or with Matrigel containing VEGF and Prominin fragment-#237 (180 µg). On day 6, animals were sacrificed and fluorescence-activated cell sorting (FACS) analysis was used for determination of the matrigel liberated cells. In order to distinguish the endothelial cells from hematopoietic cells, the cells were incubated with two antibodies CD31-PE and CD45-APC which are specific to endothelial cells and hematopoietic cells respectively. The left upper panel reflects the number of the endothelial cells which are the cells that builds vessels. As shown in FIG. 7, six times more endothelial cells (0.42% versus 0.07%) (upper left panel) were observed when the 180 ug of #237 peptide was added to the VEGF. This observation confirms that #237 is a potent angiogenic factor which has a synergistic effect on endothelial cell migration induced by VEGF.

Example 7

Prominin Fragment (#237) Increases Neovascularization in a Wound Healing Model

Figure 8A:
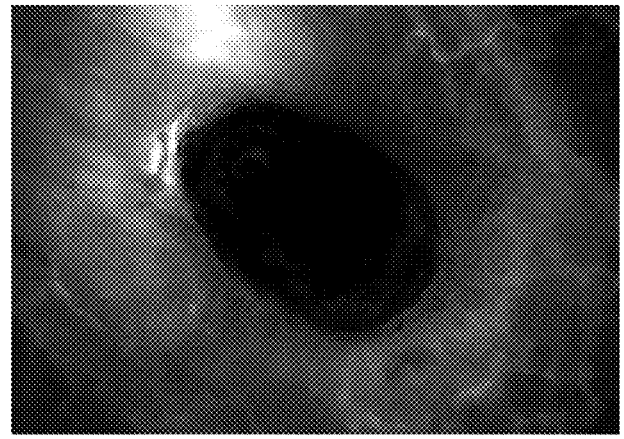
FIG. 8A shows the wound healing on a nude mouse ear wound (2.25 mm circular wound size) with plain MATRIGEL after 5 days. MATRIGEL solution had minimal effect on neovascularization.
Figure 8B:
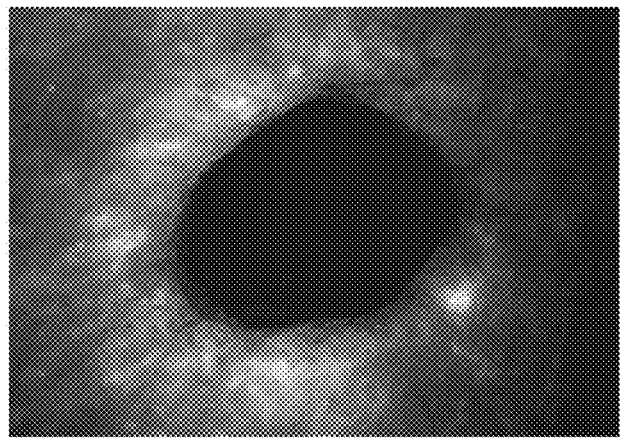
FIG. 8B shows the wound healing on a nude mouse ear wound (2.25 mm circular wound size) with MATRIGEL containing the Prom-1 peptide #237 (180 µg) after 5 days. The Prom-1 peptide #237 matrigel solution significantly increased the neovascularization around the ear wound site (×4).

Microvascular in-growth into damaged tissue is an essential component of the normal healing process. In fact, wound therapy is often aimed at promoting neovascularization. The model consists of wounding the dorsal aspect of the ear of a nude mouse. A circular punch was used to create a standardized wound on a nude mouse ear. Constant diameter of wound is given by the size of the punch (2.25 mm), and the ears were treated daily with plain matrigel (FIG. 8A) or matrigel containing peptide #237 (180 µg) (FIG. 8B) for 5 days. Matrigel solution had minimal effect on neovascularization, but in contrast, the matrigel containing peptide #237 significantly increased the neovascularization around the ear wound site (×4). In order to evaluate the wound neovascularization, the mice were inoculated by dextran-FITC which specifically labeled the endothelial cells, immediately after anesthetizing them. The ear/wound was observed and as shown in FIG. 8, the angiogenesis around the circular wound among the treated mice (the #237 peptide) was greater than among the untreated mice.

Example 8

Circularized Peptides of Prominin-1

Provided herein are exemplary circular peptides of prominin-1 that are contemplated for use with the methods and compositions described herein. The amino acids GG are added prior to the cysteine residue to permit disulfide bridge formation.

Exemplary sequences for circular peptides of peptide #237 include, but are not limited to, ACGGDRVQRQTTTV-VAGGC (SEQ ID NO: 15); ACGGDRVQRQTTTV-VAGGGGGGC (SEQ ID NO: 16); and CGGGGGGDRVQRQTTTVVAGGCA (SEQ ID NO: 17).

Further cyclic peptides for e.g., peptide #237 can be designed using the following exemplary formulas. These formulas permit a peptide to be converted into a cyclic peptide by the formation of a disulfide bond between the two cysteines. Exemplary formulas for designing cyclic peptides of peptide #237 are shown below:

```
CX(DRVQRQTTTVVA)ZC,      (SEQ ID NO: 37)

ACX(DRVQRQTTTVVA)ZC,     (SEQ ID NO: 38)
``` wherein X or Z are each independently 0-20 amino acids used as spacers. In the specific examples for peptide 237 shown above (SEQ ID NO: 15; SEQ ID NO: 16; SEQ ID NO: 17) these spacer amino acids are G.

For non-237 based sequences, examples of formulas based upon other active linear peptide sequences that can then be made into cyclic peptides by the formation of a disulfide bond between the two cysteines are below:
CX(active linear peptide sequence)ZC,
A CX(active linear peptide sequence)ZC,
CX(active linear peptide sequence)ZCA,
wherein X or Z are each independently 0-20 amino acids used as spacers.

Example 9

Peptide #237 Promotes Wound Healing

Figure 10A:
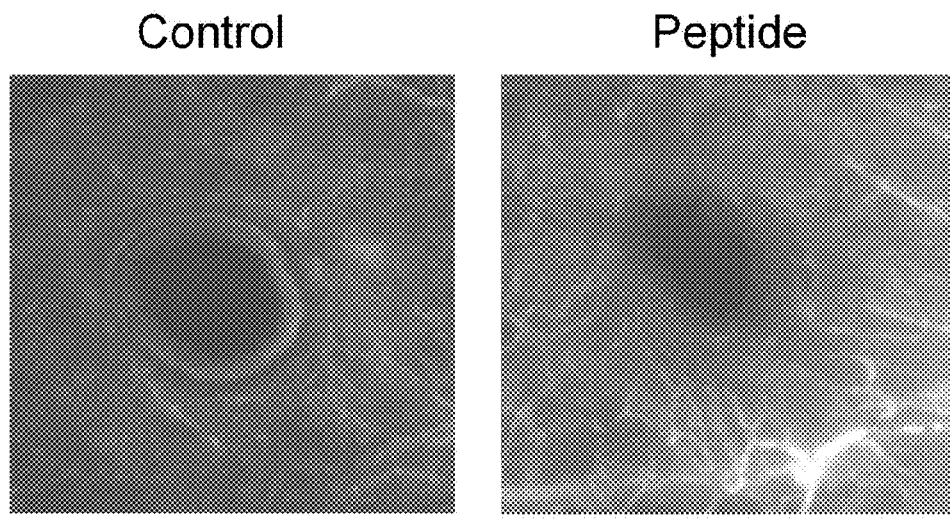
FIGS. 10A and 10B show that the peptide #237 promotes wound healing after 14 days in a mouse ear punch model.
Figure 10B:
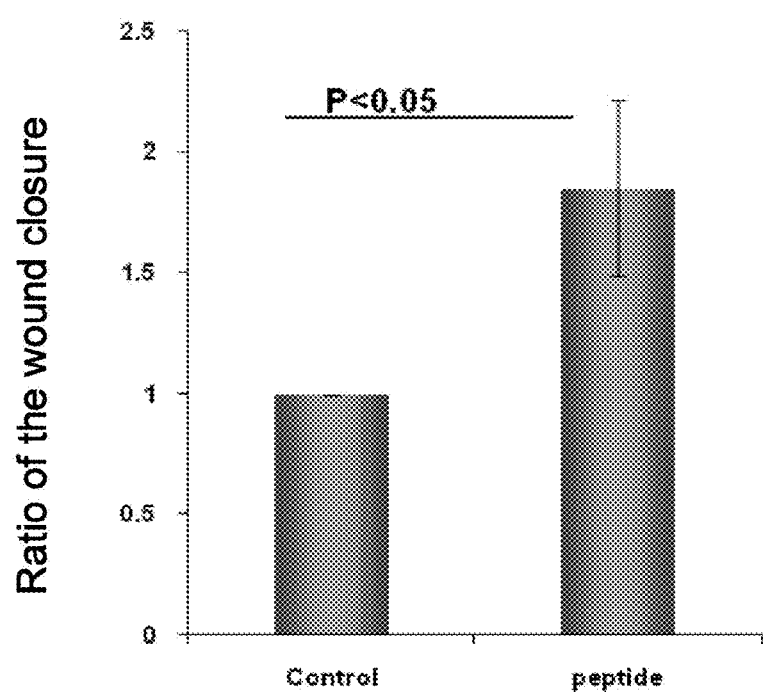

In addition to increasing angiogenesis, peptide #237 also accelerates wound healing. In order to evaluate the effect of the peptide on wound healing, ears of five mice were wounded using a circular punch, which creates a wound measuring 1 mm. The ears of wounded mice were treated daily with either MATRIGEL or MATRIGEL containing #237 peptide for 14 days. As shown in FIG. 10, the wound area of the treated mice was significantly smaller than among the untreated mice on day 14, indicating that #237 promotes wound healing in a mouse model.

Example 10

Peptide #237 Promotes Neurite Outgrowth

Primary cortical neuronal cells ($2 \times 10^4$ per well) were plated on poly-L-lysine coated 24 well dishes and treated with either scrambled #237 or peptide #237 (0.25 µg/µL). Cells were then cultured for 2 days.

Figure 11A:
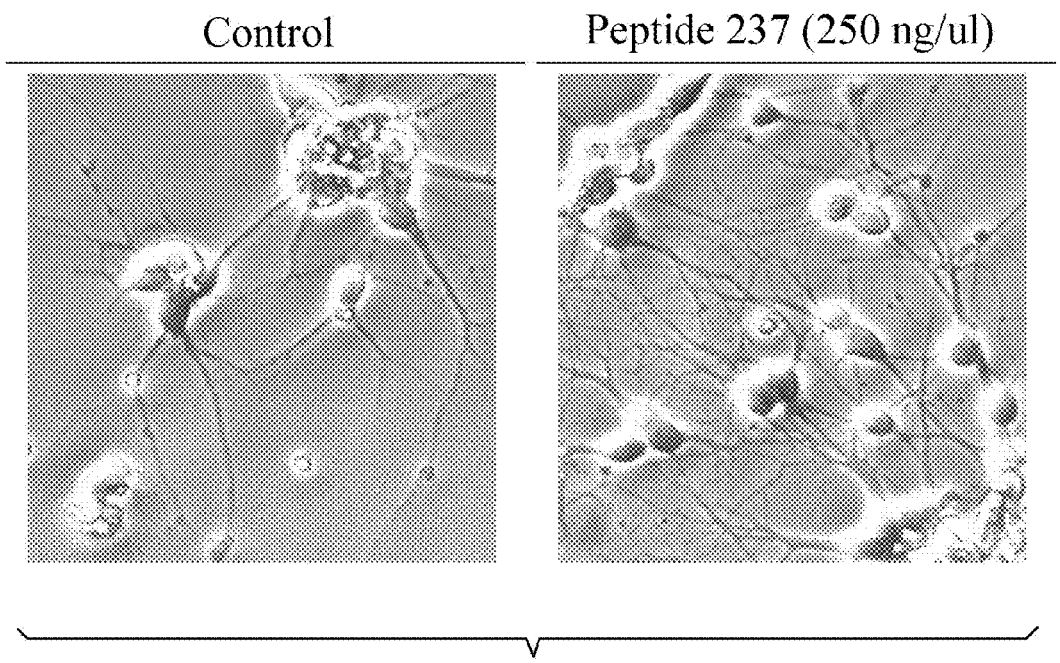
FIGS. 11A and 11B show that peptide #237 promotes neurite outgrowth in primary cortical neuronal cells.
Figure 11B:
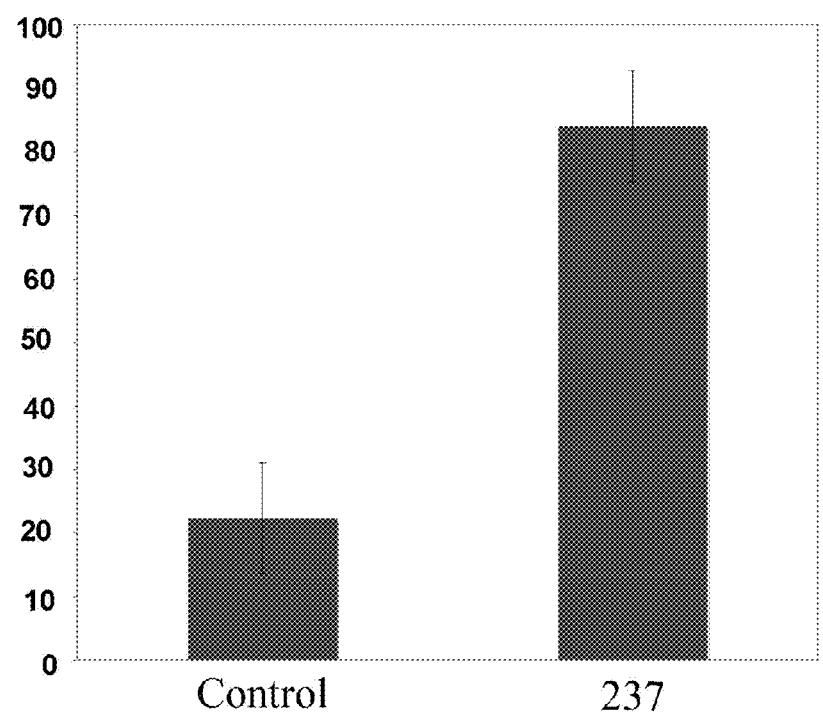

Neurite outgrowth was evaluated by counting the number of neurites extended from the same number of cells and at the same area. As shown in FIG. 11, peptide #237 dramatically induces branched and longer neurites compared to cells treated with a scrambled peptide. Without wishing to be bound by theory, these data indicate that peptide #237 stimulates neuronal growth and regeneration.

Peptide 237 increases neurite outgrowth in terminally differentiated cortical neurons. The number of neurite arborizations in these postmitotic cells was estimated using light microscopy by manually counting the number of projections in a given field containing approximately equivalent number of cells. Quantification of neurite outgrowth was also performed by fluorescent staining with a neuron-specific marker (i.e., neurofilament) followed by automated, computational analysis (data not shown).

Example 11

Peptide #237 Improves Blood Flow in Ischemic Limbs in a Mouse

The therapeutic activity on ischemic tissues in mice of peptide #237 (DRVQRQTTTVVA) (SEQ. ID. NO: 8) was demonstrated using a mouse hind limb ischemia model in which ischemia was induced by femoral artery ligation in one leg. Mice were ligated in one of their femoral arteries (the right limb) to simulate hind limb ischemia. The blood flow in mice was analyzed by machine for each mouse before and immediately after the procedure to evaluate if the femoral was ligated properly. Blood flow was compared with the non-operated leg by a laser Doppler imager. Peptide #237 was administered intraperitoneal immediately following femoral artery occlusion significantly improves limb perfusion, within three to six days. The ischemic limb is seen as the limb on left side in the laser Doppler images.

Figure 12:
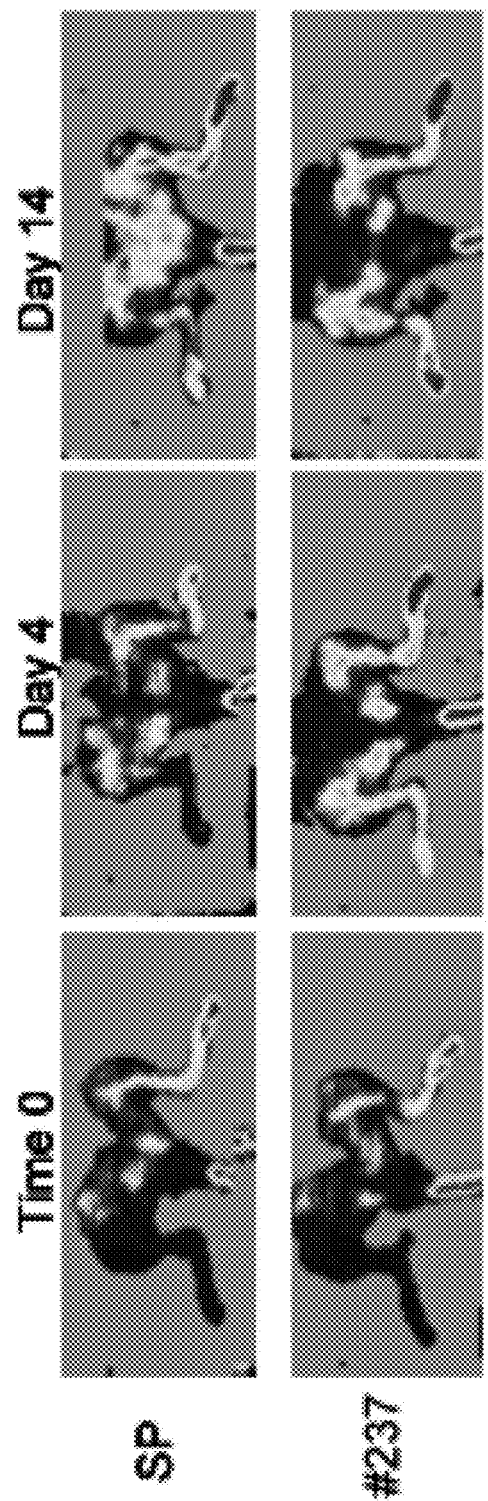
FIG. 12 shows the laser Doppler images of ischemic mouse tissue treated with peptide #237 (SEQ. ID. NO: 8). Animals were ligated in the right limb but the ischemic limb is on the left side of the laser Doppler images. Black areas indicate no blood flow. White areas indicate blood flow. Dark shades within the white area at the distal end of limbs indicate high blood flow. SP=scrambled peptide control.

FIG. 12 shows a representative evaluation of the ischemic (left side of each image) and non-ischemic (right side of each image) hind limbs, immediately after, and on days 4 and 14 after surgery. In FIG. 12, the white areas indicate normal perfusion with normal blood circulation and black areas indicate no blood flow in the ischemic left hind limb. Mice administered with peptide #237 showed increased blood flow recovery compared to saline-treated mice. Dark shaded areas within the white areas located at the distal ends of the limbs indicate extremely good blood flow.

Figure 13:
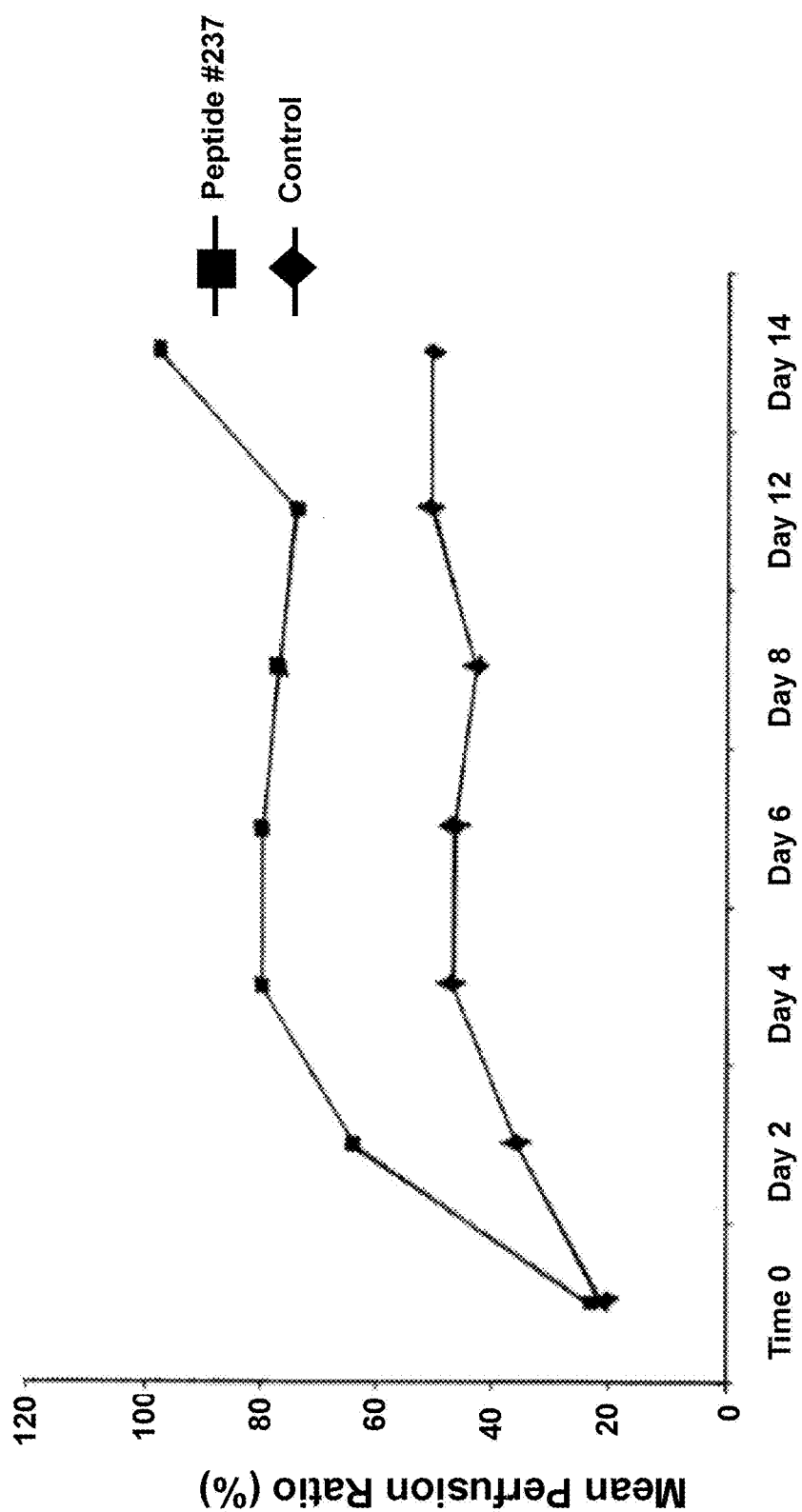
FIG. 13 is a graph showing the blood flow of the ischemic hind limb as the ratio between the perfusion of the ischemic limb and the uninjured limb.

The blood flow of the ischemic hind limb is expressed as the ratio between the perfusion of the ischemic limb and the uninjured limb in FIG. 13. On average, the peptide #237-treated mice showed about 30-40% increase perfusion compared to saline-treated mice.

Example 12

Peptide #237 Improves Bone Repair in Calvaria Critical Size Defect Experiment In this study, the inventors examined the ability of peptide #237 to enhance repair of a critical size defect in a rat calvaria critical size defect experiment. Critical size calvarial defects (5-mm diameter) were created in rats and locally treated with saline (control) or peptide #237 for 28 days (100 µg/mice/5 days). After 28 days, analysis of bone regeneration was determined by soft x-ray.

Figure 14:
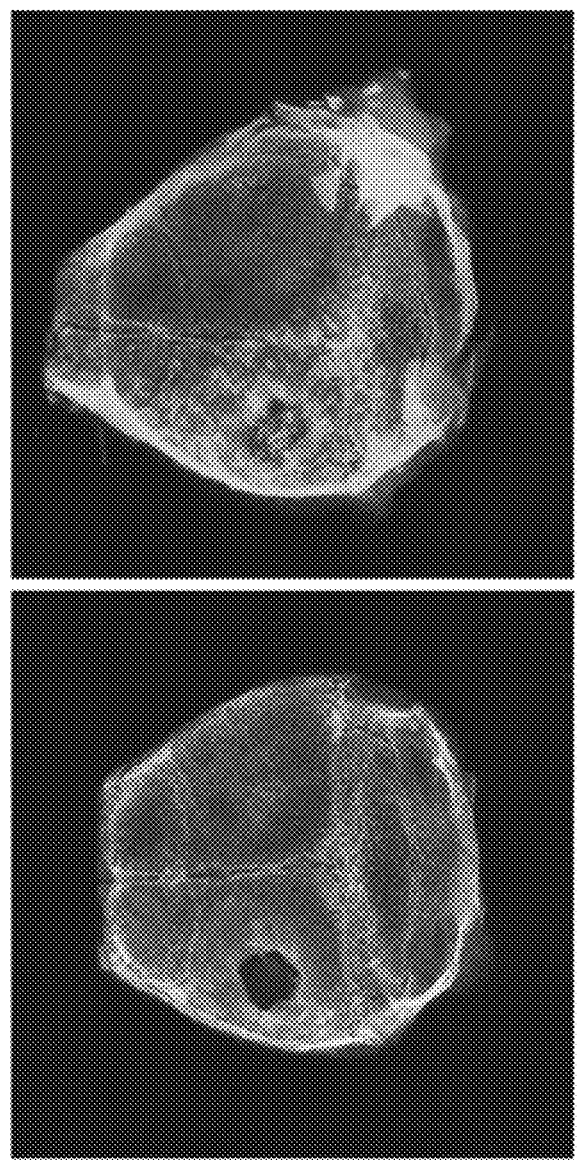
FIG. 14 shows that peptide #237 improves bone repair in a calvaria critical size defect experiment.

FIG. 14 shows the extent of bone regeneration in the mice administered with peptide #237 compared with control mice that were treated with saline only. The edges of the calvaria on the animal treated with peptide #237 have completely sealed and covered the aperture while those of the control animal treated with saline are still very distinct after 28 days.

Example 10

Alanine Substituted Peptide #237 at Position 5 (Ala 5) Enhanced VEGF Binding by Endothelial Cells The inventors also investigated which amino acid residues in peptide #237 are important for the various angiogenic and VEGF related binding activity described herein. To achieve this, the inventors singly changed each of the 12 amino acid residues in peptide #237 to alanine and performed experiments examining the effect of the alanine substitution at various positions on endothelial cell binding to VEGF. A total of 12 alanine substituted peptides were made and tested: Ala-1, Ala-2, Ala-3, Ala-4, Ala-5, Ala-6, Ala-7, Ala-8, Ala-9, Ala-10, Ala-11, Ala-12, (SEQ. ID. NOS. 39-50) wherein the number indicate the position where the alanine substitution occurred. (Note that the amino acid at position 12 of peptide #237 was changed to glycine in Ala-12). In addition, a "flip #237" peptide having the sequence AAVVTTTQRQVRD (SEQ. ID. NO. 53) was also made and studied.

Figures 15A, 15B, 15C:
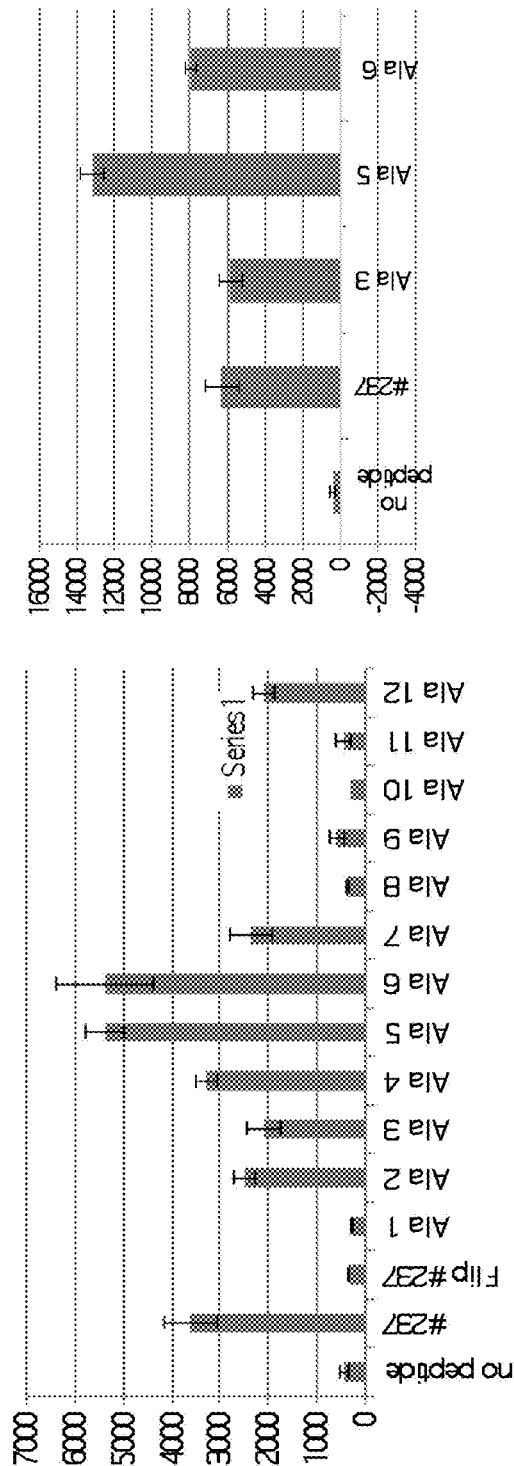
FIGS. 15A and 15B are representative histograms showing the effects of various alanine substitutions in the #237 peptides on endothelial cells binding to VEGF. Each of the 12 amino acid residues of the original #237 peptide was singly replaced by alanine. (Note that the amino acid at position 12 of original #237 peptide was replaced by glycine in Ala-12).
FIG. 15C discloses twelve alanine substitution #237 peptides, SEQ. ID. NOS. 39-50 respectively, in order of appearance.

FIGS. 15A and 15B show that alanine substitutions showed a marked increase in activity when the substitution was made at position 5. Ala-5 peptide has the arginine at position 5 replaced by alanine. The ability of endothelial cells to bind VEGF was increased by more than twice compared to the treatment with the original #237.

The references cited herein and throughout the specification are incorporated herein by reference.

TABLE 1

| Peptide Sequence Number | Amino acid Sequence of peptide | Seq. ID. No. | VEGF binding | Stimulate VEGF binding in other cells | Endothelial Cell growth | ↑angiogenesis in VEGF | ↑Endothelial cell migrate |
|---|---|---|---|---|---|---|---|
| #3 | LCGNSFSGGQPS | 4 | + | -(1) | +/+ | | |
| #42 | PNIIPVLDEIKS | 5 | + | -(1) | +/+ | | |
| #77 | LCGVCGYDRHAT | 6 | + | -(1) | +/ | | |

TABLE 1-continued

| Peptide Sequence Number | Amino acid Sequence of peptide | Seq. ID. No. | VEGF binding | Stimulate VEGF binding in other cells | Endo-thelial Cell growth | ↑angio-genesis in VEGF | ↑Endo-thelial cell migrate |
|---|---|---|---|---|---|---|---|
| #122 | ITNNTSSVIIEE | 7 | + | -(1) | | | |
| #237 | DRVQRQTTTVVA | 8 | + | +(2) | +/+ | + | + |
| #640 | CSFAYDLEAKANSLPPGNLRN | 9 | + | -(1) | +/+ | | |

What is claimed:

1. An isolated peptide comprising an amino acid sequence selected from the group consisting of:
   LCGNSFSGGQPS (SEQ ID NO: 4);
   PNIIPVLDEIKS (SEQ ID NO: 5);
   LCGVCGYDRHAT (SEQ ID NO: 6);
   DRVQRQTTTVVA (SEQ ID NO: 8);
   CSFAYDLEAKANSLPPGNLRN (SEQ ID NO: 9);
   and DRVQBQTTTVVA (SEQ ID NO: 54), wherein B is any one of the naturally occurring amino acids;
   and wherein the isolated peptide is no more than 50 amino acids in length.

2. The isolated peptide of claim 1, wherein said isolated peptide is constructed into a cyclic peptide.

3. The cyclic peptide of claim 2, wherein the cyclic peptide comprises a formula of CX(DRVQBQTTTVVA)ZC (SEQ ID NO: 51) or ACX(DRVQBQTTTVVA)ZC (SEQ ID NO: 52), wherein X or Z are each independently 0-20 amino acids, and wherein B is any one of the naturally occurring amino acids.

4. The cyclic peptide of claim 3, wherein the glutamine (Q) at position 6 of the core (DRVQBQTTTVVA) (SEQ ID NO: 54) of the cyclic peptide is substituted with any one of the known 20 amino acids other that glutamine.

5. The isolated peptide of claim 2, wherein the cyclic peptide is selected from the group consisting of: ACGG(DRVQRQTTTVVA)GGC (SEQ ID NO: 15), ACGG(DRVQRQTTTVVA)GGGGGC (SEQ ID NO: 16), and CGGGGGG(DRVQRQTTTVVA)GGCA (SEQ ID NO: 17).

6. The isolated peptide of claim 1, wherein the peptide is conjugated to a polymer.

7. A fusion protein comprising the isolated peptide of claim 1, fused to a heterologous peptide or polypeptide, wherein the fusion protein is not a full-length prominin-1.

8. A composition comprising a pharmaceutically acceptable carrier and an isolated peptide of claim 1 or fusion protein of claim 7.

9. A method of promoting angiogenesis in a tissue in need thereof, the method comprising contacting said tissue with a composition of claim 8.

10. The method of claim 9, wherein the method is applied in the context of promoting wound healing, neuronal growth, protection or repair, tissue repair, bone repair, fertility promotion, cardiac hypertrophy, treatment of erectile dysfunction, modulation of blood pressure, revascularization after disease or trauma, tissue grafts, or tissue engineered constructs.

11. The isolated peptide of claim 1, wherein the isolated peptide is no more than 30 amino acids in length.

12. An isolated peptide of claim 1 that comprises an amino acid substitution at one or more of positions 2, 3, 4, 5, 6, 7 or 12 of DRVQRTTTVVA (SEQ ID NO: 8) or one or more of positions 1, 3, 8, or 9 of LCGNSFSGGQPS (SEQ ID NO: 4).

13. An isolated peptide comprising an amino acid sequence consisting of:
   ITNNTSSVIIEE (SEQ ID NO: 7), wherein the isolated eptide is no more than 25 amino acids in length.

* * * * *

UNITED STATES PATENT AND TRADEMARK OFFICE
CERTIFICATE OF CORRECTION

PATENT NO. : 8,618,055 B2
APPLICATION NO. : 13/015376
DATED : December 31, 2013
INVENTOR(S) : Avner Adini et al.

Page 1 of 1

It is certified that error appears in the above-identified patent and that said Letters Patent is hereby corrected as shown below:

In the Claims

Column 124, lines 58-61 should read:

12. An isolated peptide of claim 1 that comprises an amino acid substitution at one or more of positions 2, 3, 4, 5, 6, 7 or 12 of DRVQRQTTTVVA (SEQ ID NO: 8) or one or more of positions 1, 3, 8, or 9 of LCGNSFSGGQPS (SEQ ID NO: 4).

Signed and Sealed this
First Day of April, 2014

Michelle K. Lee
*Deputy Director of the United States Patent and Trademark Office*